US010415095B2

(12) United States Patent
Wu et al.

(10) Patent No.: US 10,415,095 B2
(45) Date of Patent: Sep. 17, 2019

(54) LNCRNA SERVES AS A BIOMARKER AND THERAPEUTIC TARGET

(71) Applicant: UNIVERSITY OF FLORIDA RESEARCH FOUNDATION, INC., Gainesville, FL (US)

(72) Inventors: Lizi Wu, Gainesville, FL (US); Zirong Chen, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/564,740

(22) PCT Filed: Apr. 11, 2016

(86) PCT No.: PCT/US2016/026897
§ 371 (c)(1),
(2) Date: Oct. 6, 2017

(87) PCT Pub. No.: WO2016/164884
PCT Pub. Date: Oct. 13, 2016

(65) Prior Publication Data
US 2018/0112272 A1    Apr. 26, 2018

Related U.S. Application Data

(60) Provisional application No. 62/145,825, filed on Apr. 10, 2015, provisional application No. 62/320,510, filed on Apr. 9, 2016.

(51) Int. Cl.
| | |
|---|---|
| *C12Q 1/6886* | (2018.01) |
| *A61K 31/7088* | (2006.01) |
| *C12Q 1/68* | (2018.01) |
| *A61K 48/00* | (2006.01) |
| *C12N 15/113* | (2010.01) |
| *A61K 45/06* | (2006.01) |
| *A61P 35/00* | (2006.01) |
| *A61K 31/713* | (2006.01) |
| *C12N 15/115* | (2010.01) |

(52) U.S. Cl.
CPC ........ *C12Q 1/6886* (2013.01); *A61K 31/7088* (2013.01); *A61K 31/713* (2013.01); *A61K 45/06* (2013.01); *A61K 48/00* (2013.01); *A61P 35/00* (2018.01); *C12N 15/113* (2013.01); *C12N 15/115* (2013.01); *C12Q 1/68* (2013.01); *C12N 2310/113* (2013.01); *C12N 2310/16* (2013.01); *C12N 2320/31* (2013.01); *C12Q 2600/106* (2013.01); *C12Q 2600/156* (2013.01); *C12Q 2600/158* (2013.01); *C12Q 2600/178* (2013.01)

(58) Field of Classification Search
CPC ... C12Q 1/6886; A61P 35/00; A61K 31/7088; A61K 31/713; C12N 15/113
See application file for complete search history.

(56) References Cited

U.S. PATENT DOCUMENTS

| | | |
|---|---|---|
| 2013/0158023 A1 | 6/2013 | Ning et al. |
| 2013/0178428 A1 | 7/2013 | Hoon et al. |

FOREIGN PATENT DOCUMENTS

| | | | | |
|---|---|---|---|---|
| WO | WO-2011008956 A2 * | 1/2011 | ......... | A61K 31/5375 |
| WO | WO 2015/024986 | 2/2015 | | |

OTHER PUBLICATIONS

Liang, X- H. et al. "Non-coding RNA LINC00473 mediates decidualization of human endometrial stromal cells in response to cAMP signaling" *Scientific Reports*, Mar. 7, 2016, pp. 1-9, vol. 6, No. 22744.
Database NCBI [Online] Accession No. NR_026860.1, Mar. 15, 2015, pp. 1-2.
Reitmair, A. et al. "C6orf176: a novel possible regulator of cAMP-mediated gene expression" *Physiol Genomics*, 2012, pp. 152-161, vol. 44.
Written Opinion in International Application No. PCT/US2016/026897, dated Jul. 18, 2016, pp. 1-6.
Alessi, D. R. et al. "LKB1-Dependent Signaling Pathways" *Annual Review of Biochemistry*, Feb. 16, 2006, pp. 137-163, Supp pp. 1-3, vol. 75.
Batista, P. J. et al. "Long Noncoding RNAs: Cellular Address Codes in Development and Disease" *Cell*, Mar. 14, 2013, pp. 1298-1307, vol. 152.
Esteller, M. et al. "Epigenetic inactivation of LKB1 in primary tumors associated with the Peutz-Jeghers syndrome" *Oncogene*, 2000, pp. 164-168, vol. 19.
Geisler, S. et al. "RNA in unexpected places: long non-coding RNA functions in diverse cellular contexts" *Nature Reviews Molecular Cell Biology*, Nov. 2013, pp. 699-712, vol. 14.
Kaufman, J. M. et al. "LKB1 Loss Induces Characteristic Patterns of Gene Expression in Human Tumors Associated with NRF2 Activation and Attenuation of PI3K-AKT" *Journal of Thoracic Oncology*, Jun. 2014, pp. 794-804, vol. 9, No. 6.

(Continued)

*Primary Examiner* — Brian Whiteman
(74) *Attorney, Agent, or Firm* — Timothy H. Van Dyke; Beusse, Wolter, Sanks & Maire PLLC

(57) ABSTRACT

The invention pertains to increased LINC00473 as an indicator of a cancer involving loss or reduction in LKB1 function. LINC00473 is also provided as a therapeutic target for treating a cancer involving loss or reduction in LKB1 function. The invention provides a method of identifying a subject as having a cancer involving loss or reduction in LKB1 function based on the level of LINC00473 in the test sample obtained from the subject and administering an effective amount of a LINC00473 inhibitor to the subject to treat the cancer. The LINC00473 inhibitor can be a small-inhibitory RNA, short hairpin RNA, bifunctional RNA, antisense oligonucleotide, ribozyme, deoxyribozyme, aptamer or small molecule inhibitor. A pharmaceutical composition comprising a LINC00473 inhibitor is also provided for the treatment of a cancer involving loss or reduction in LKB1 function.

19 Claims, 36 Drawing Sheets
Specification includes a Sequence Listing.

(56) References Cited

OTHER PUBLICATIONS

Komiya, T. et al. "Enhanced activity of the CREB co-activator Crtc1 in LKB1 null lung cancer" *Oncogene*, 2010, pp. 1672-1680, vol. 29.

Li, C. H. et al. "Targeting long non-coding RNAs in cancers: Progress and prospects" *The International Journal of Biochemistry & Cell Biology*, 2013, pp. 1895-1910, vol. 45.

Ling, H. et al. "MicroRNAs and other non-coding RNAs as targets for anticancer drug development" *Nature Reviews Drug Discovery*, Nov. 2013, pp. 847-865, vol. 12.

Moran, V. A. et al. "Emerging functional and mechanistic paradigms of mammalian long non-coding RNAs" *Nucleic Acids Research*, Apr. 5, 2012, pp. 6391-6400, vol. 40, No. 14.

Nakada, Y. et al. "The LKB1 Tumor Suppressor as a Biomarker in Mouse and Human Tissues" *PLOS ONE*, Sep. 25, 2013, pp. 1-7, vol. 8, No. 9.

Sanchez-Cespedes, M. "The role of LKB1 in lung cancer" *Familial Cancer*, Apr. 23, 2011, pp. 447-453, vol. 10.

Shackelford, D. B. et al. "The LKB1-AMPK pathway: metabolism and growth control in tumour suppression" *Nature Reviews Cancer*, Aug. 2009, pp. 563-575, vol. 9.

Shackelford, D. B. et al. "LKB1 Inactivation Dictates Therapeutic Response of Non-Small Cell Lung Cancer to the Metabolism Drug Phenformin" *Cancer Cell*, Feb. 11, 2013, pp. 143-158, vol. 23.

Vaahtomeri, K. et al. "Molecular mechanisms of tumor suppression by LKB1" *FEBS Letters*, 2011, pp. 944-951, vol. 585.

Wapinski, O. et al. "Long noncoding RNAs and human disease" *Trends in Cell Biology*, Jun. 2011, pp. 354-361, vol. 21, No. 6.

Zheng, B. et al. "Oncogenic B-RAF Negatively Regulates the Tumor Suppressor LKB1 to Promote Melanoma Cell Proliferation" *Molecular Cell*, Jan. 30, 2009, pp. 237-247, vol. 33.

\* cited by examiner

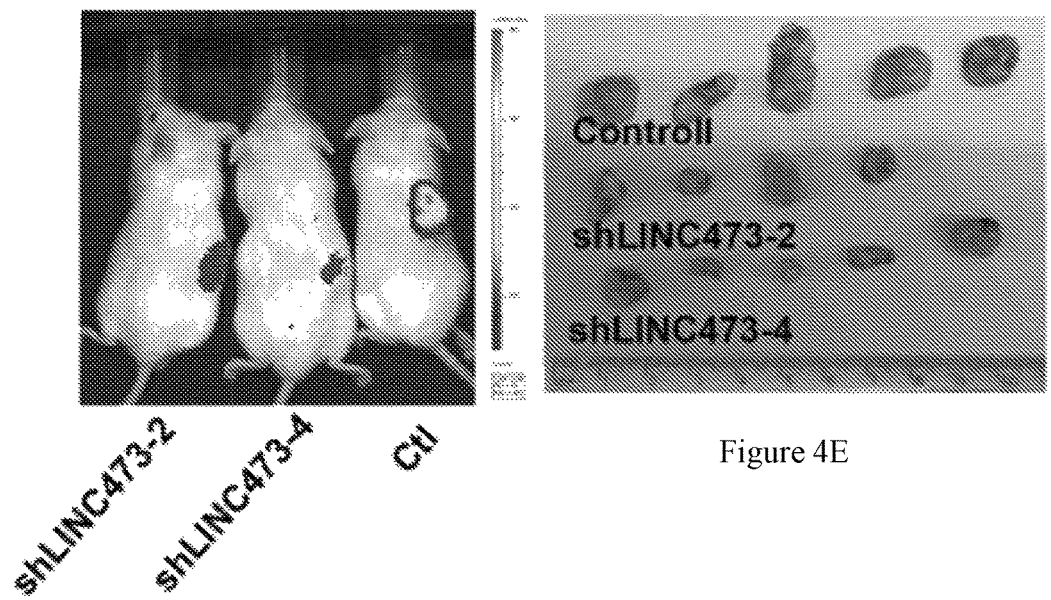
Figure 4D
Figure 4E
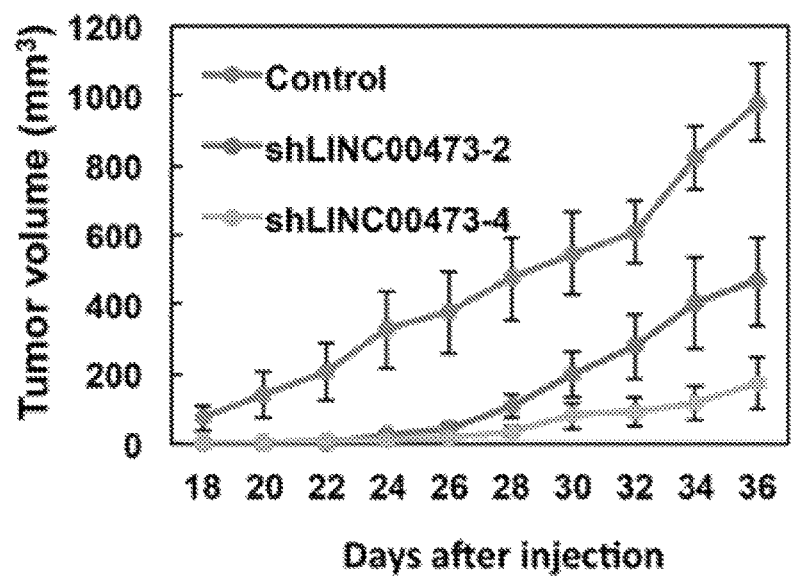
Figure 4F

Lung adenocarcinoma
(LKB1 wt, Lnc473 negative)

SEQUENCE LISTING

<160> NUMBER OF SEQ ID NOS: 62

<210> SEQ ID NO 1
<211> LENGTH: 1832
<212> TYPE: DNA
<213> ORGANISM: Homo sapiens

<400> SEQUENCE: 1

```
gttcctgaga gcacaagcac ccccaaatgt gaagtgcact cggacacaca cacacacaca      60
cacgcacgca cacacaagca ctcatgttct aaagagagag gtctgagtcc gaagttgctg     120
ctgctgggag cttgagctga gatggactgg tcttcatggg cgcccaaggc gctgggtgca     180
gctttccccg agaccccag atggaaagga gggaaggagg aaccccacac actcgccttt      240
tgcgagaaga tcggcgcgca ccccagagtg ccccaagcct ttggaatctg cctgctgagc     300
ggagcgcgcg agcgtggtgg acaggtcccg aacttggcca gcgggctttc ttggcaactt     360
gctttgcgca gttctccatg gaaccctgga cccactgtgc tcccggcgcc ttgccttttt     420
ttttcttttt ctttctctca ctgtctcttt ttaaatttat gaactcgaaa tgaagcggaa     480
agcagatatg cgcgtcagca tactttggcg gacctttaa aaatgaact gtcggctgcg       540
gctggaaggc gcaggcaggc gccctggaga gaattcacag ggaggcacag gacagaacgc     600
tcccaggaac gaggaagcac ccccagaaag gagcgctcta tgggctccag gcagccgagg    660
aaacgcgaac gtgagccccg tgactgcact cccacgtgca ccaacgctgc cagtgtgagc     720
agaagcggag cccgcagagc gccaggctgc gccgggagat gcatcacgat gaaaaactgc    780
gccagagcat ggcgggaact ttccgagagg gcgtgttgtt tccaggcggt tccaccttct    840
aatatgaaac agtcttggtt gatttccctt gatactactt tatgctcggc ctggttgttg    900
gcaagtagct gcccgcgtct gtacgcgccc ttgattagtt tccactgcat gtgttttaac    960
acagtcctcc ttttttccacg tttatttggg ccaaccctgt ctgcaaagat ccagtttaat   1020
acagatttga gtctacgtgc tatagcctgg aaatgtacta aagacactac aacatattgc   1080
tgaaagaata gaatctttat tctgaatgca aagcggacac ctagtaaaaa attctggaat   1140
aataaaacaa gcaaggctta tgtgctcagt tttggggacc tccaattta aaggcttagt    1200
cattgtcacg gtgtaaggtt tacccattgc ccccatcaca cagatgtggg attgttgaga    1260
gctgagtgtc ctatgacctc ttctgctgcc caagaacttg gggtgggtgg taactggaga    1320
aatcaaagtg atcagctgca aagaacgctt ccattgctgg agcttggttg tgcgggattc    1380
tccacggagg tcttaaggca gagacaaaaa caaggacttt gggaggctcc tgtgagcagc    1440
caaaagggtt tagagtcagg cagcctcagg ttacaaatcc agtcctgcag gctaggagtt    1500
gtgtaagctt aaaaagtga ctgcacttcc aggaacatca tttccctacc tgctcctcct    1560
tctgacgggt tttctgagga caatggaatc cacactctgt gtcgaacact tttctaatta    1620
gcgatgtgca gacactgttt attttacagg aataaaaatg ccagaagaac ccaagtcata    1680
ttcatttaaa gcagggtgac aagtacacca aaatctgaaa aatcatcact aaagaactta    1740
tccatgtaac caaaaccat tgaaataaaa gtaaactatg gaaacaaaat ttaaaagtaa    1800
taaaatttaa aagtccaaaa aaaaaaaaaa aa                                  1832
```

<210> SEQ ID NO 2

```
<211> LENGTH: 1123
<212> TYPE: DNA
<213> ORGANISM: Homo sapiens

<400> SEQUENCE: 2
gttcctgaga gcacaagcac ccccaaatgt gaagtgcact cggacacaca cacacacaca    60
cacgcacgca cacacaagca ctcatgttct aaagagagag gtctgagtcc gaagttgctg   120
ctgctgggag cttgagctga gatggactgg tcttcatggg cgcccaaggc gctgggtgca   180
gctttccccg agaccccag atggaaagga gggaaggagg aaccccacac actcgccttt    240
tgcgagaaga tcggcgcgca ccccagagtg ccccaagcct ttggaatctg cctgctgagc   300
ggagcgcgcg agcgtggtgg acaggtcccg aacttggcca gcgggctttc ttggcaactt   360
gctttgcgca gttctccatg gaaccctgga cccactgtgc tcccggcgcc ttgccttttt   420
ttttcttttt ctttctctca ctgtctcttt ttaaatttat gaactcgaaa tgaagcggaa   480
agcagatatg cgcgtcagca tactttggcg ggatgctggc ccaccactag tattctctgg   540
tgctcgttgt gctttgggag atcttctatg caacatggaa accatgaatt gtaccacaga   600
gggagatctt ctgtcccact aggaaactgc gaattgtacc acagagggag atcttctatg   660
caacatggag accatgaatg gtacacacag agagagatct tctatccaca tggacaccat   720
gaattgtacc acagaggcag atgttctatc caacatggaa accatgaact gtacacacag   780
agggggatat tccatccaac ataggaacca tgaactgtac acacagaggg agatcttcta   840
tccaacatgg agaccatgaa ttttaccaca aggaagatg ttctatccaa aatggaaacc    900
atgagttgta tgcctagagg gagatcttct atccaatatg taagccacga gttggacaca   960
cagagagaga tattttatcc aacttggaaa ccatgaattg tacacacaga gagatcttct  1020
atccaacacg gaaacaacga gttatacccca caggggagaa tcttctatcc aattcaggtg  1080
ttccttatgt gatagcatac tctgcatcta caactagcta aag                    1123

<210> SEQ ID NO 3
<211> LENGTH: 21
<212> TYPE: DNA
<213> ORGANISM: Artificial Sequence
<220> FEATURE:
<223> OTHER INFORMATION: sequences encoding shRNA

<400> SEQUENCE: 3
aactggatct ttgcagacag g                                              21

<210> SEQ ID NO 4
<211> LENGTH: 21
<212> TYPE: DNA
<213> ORGANISM: Artificial Sequence
<220> FEATURE:
<223> OTHER INFORMATION: sequences encoding shRNA

<400> SEQUENCE: 4
aaagatccag tttaatacag a                                              21

<210> SEQ ID NO 5
<211> LENGTH: 21
<212> TYPE: DNA
<213> ORGANISM: Artificial Sequence
<220> FEATURE:
<223> OTHER INFORMATION: sequences encoding shRNA

<400> SEQUENCE: 5
aagaacccaa gtcatattca t                                              21
```

<210> SEQ ID NO 6
<211> LENGTH: 20
<212> TYPE: DNA
<213> ORGANISM: Artificial Sequence
<220> FEATURE:
<223> OTHER INFORMATION: LINC00473 forward primer

<400> SEQUENCE: 6
aaacgcgaac gtgagccccg                                               20

<210> SEQ ID NO 7
<211> LENGTH: 20
<212> TYPE: DNA
<213> ORGANISM: Artificial Sequence
<220> FEATURE:
<223> OTHER INFORMATION: LINC00473 reverse primer

<400> SEQUENCE: 7
cgccatgctc tggcgcagtt                                               20

<210> SEQ ID NO 8
<211> LENGTH: 20
<212> TYPE: DNA
<213> ORGANISM: Artificial Sequence
<220> FEATURE:
<223> OTHER INFORMATION: CREB forward primer

<400> SEQUENCE: 8
agcagccact cagccgggta                                               20

<210> SEQ ID NO 9
<211> LENGTH: 22
<212> TYPE: DNA
<213> ORGANISM: Artificial Sequence
<220> FEATURE:
<223> OTHER INFORMATION: CREB reverse primer

<400> SEQUENCE: 9
acgtctccag aggcagcttg aa                                            22

<210> SEQ ID NO 10
<211> LENGTH: 20
<212> TYPE: DNA
<213> ORGANISM: Artificial Sequence
<220> FEATURE:
<223> OTHER INFORMATION: ASNS forward primer

<400> SEQUENCE: 10
tggctgcctt ttatcagggg                                               20

<210> SEQ ID NO 11
<211> LENGTH: 20
<212> TYPE: DNA
<213> ORGANISM: Artificial Sequence
<220> FEATURE:
<223> OTHER INFORMATION: ASNS reverse primer

<400> SEQUENCE: 11
tctgccacct ttctagcagc                                               20

<210> SEQ ID NO 12
<211> LENGTH: 20
<212> TYPE: DNA
<213> ORGANISM: Artificial Sequence
<220> FEATURE:

<223> OTHER INFORMATION: GAPDH forward primer

<400> SEQUENCE: 12
caatgacccc ttcattgacc                                          20

<210> SEQ ID NO 13
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 13
gacaagcttc ccgttctcag                                          20

<210> SEQ ID NO 14
<211> LENGTH: 25
<212> TYPE: DNA
<213> ORGANISM: Artificial Sequence
<220> FEATURE:
<223> OTHER INFORMATION: CPS1 forward primer

<400> SEQUENCE: 14
ggaaatgtag ttgctttctt aacct                                    25

<210> SEQ ID NO 15
<211> LENGTH: 21
<212> TYPE: DNA
<213> ORGANISM: Artificial Sequence
<220> FEATURE:
<223> OTHER INFORMATION: CPS1 reverse primer

<400> SEQUENCE: 15
ttgatgattt gtggcatggg c                                        21

<210> SEQ ID NO 16
<211> LENGTH: 23
<212> TYPE: DNA
<213> ORGANISM: Artificial Sequence
<220> FEATURE:
<223> OTHER INFORMATION: PDE4B forward primer

<400> SEQUENCE: 16
ccgatcgcat tcaggtcctt cgc                                      23

<210> SEQ ID NO 17
<211> LENGTH: 20
<212> TYPE: DNA
<213> ORGANISM: Artificial Sequence
<220> FEATURE:
<223> OTHER INFORMATION: PDE4B reverse primer

<400> SEQUENCE: 17
tgcggtctgt ccattgccga                                          20

<210> SEQ ID NO 18
<211> LENGTH: 20
<212> TYPE: DNA
<213> ORGANISM: Artificial Sequence
<220> FEATURE:
<223> OTHER INFORMATION: PTGS2 forward primer

<400> SEQUENCE: 18
gttcccaccc atgtcaaaac                                          20

```
<210> SEQ ID NO 19
<211> LENGTH: 20
<212> TYPE: DNA
<213> ORGANISM: Artificial Sequence
<220> FEATURE:
<223> OTHER INFORMATION: PTGS2 reverse primer

<400> SEQUENCE: 19
ccggtgttga gcagttttct                                               20

<210> SEQ ID NO 20
<211> LENGTH: 19
<212> TYPE: DNA
<213> ORGANISM: Artificial Sequence
<220> FEATURE:
<223> OTHER INFORMATION: PDE4D forward primer

<400> SEQUENCE: 20
ctcctacgcg gtggagacc                                                19

<210> SEQ ID NO 21
<211> LENGTH: 20
<212> TYPE: DNA
<213> ORGANISM: Artificial Sequence
<220> FEATURE:
<223> OTHER INFORMATION: PDE4D reverse primer

<400> SEQUENCE: 21
catcaaaacg cctgagtccc                                               20

<210> SEQ ID NO 22
<211> LENGTH: 19
<212> TYPE: DNA
<213> ORGANISM: Artificial Sequence
<220> FEATURE:
<223> OTHER INFORMATION: SLC7A2 forward primer

<400> SEQUENCE: 22
cagttgctgc cacgttgac                                                19

<210> SEQ ID NO 23
<211> LENGTH: 20
<212> TYPE: DNA
<213> ORGANISM: Artificial Sequence
<220> FEATURE:
<223> OTHER INFORMATION: SLC7A2 reverse primer

<400> SEQUENCE: 23
ggctggtacc tgaggatgag                                               20

<210> SEQ ID NO 24
<211> LENGTH: 25
<212> TYPE: DNA
<213> ORGANISM: Artificial Sequence
<220> FEATURE:
<223> OTHER INFORMATION: NEDD9 forwrad primer

<400> SEQUENCE: 24
gctgccgaaa tgaagtataa gaatc                                         25

<210> SEQ ID NO 25
<211> LENGTH: 20
<212> TYPE: DNA
<213> ORGANISM: Artificial Sequence
<220> FEATURE:
<223> OTHER INFORMATION: NEDD9 reverse primer
```

```
<400> SEQUENCE: 25
cttccagtcc ccctgtgttc                                               20

<210> SEQ ID NO 26
<211> LENGTH: 19
<212> TYPE: DNA
<213> ORGANISM: Artificial Sequence
<220> FEATURE:
<223> OTHER INFORMATION: LINC00473 forward primer

<400> SEQUENCE: 26
agcagccttg ccaaaggtc                                                19

<210> SEQ ID NO 27
<211> LENGTH: 20
<212> TYPE: DNA
<213> ORGANISM: Artificial Sequence
<220> FEATURE:
<223> OTHER INFORMATION: LINC00473 reverse primer

<400> SEQUENCE: 27
tttcccttta agccggagat                                               20

<210> SEQ ID NO 28
<211> LENGTH: 20
<212> TYPE: DNA
<213> ORGANISM: Artificial Sequence
<220> FEATURE:
<223> OTHER INFORMATION: LINC00473 R387 primer

<400> SEQUENCE: 28
ccatggagaa ctgcgcaaag                                               20

<210> SEQ ID NO 29
<211> LENGTH: 20
<212> TYPE: DNA
<213> ORGANISM: Artificial Sequence
<220> FEATURE:
<223> OTHER INFORMATION: LINC00473 R249 primer

<400> SEQUENCE: 29
cttctcgcaa aaggcgagtg                                               20

<210> SEQ ID NO 30
<211> LENGTH: 20
<212> TYPE: DNA
<213> ORGANISM: Artificial Sequence
<220> FEATURE:
<223> OTHER INFORMATION: LINC00473.v1 F1382 primer

<400> SEQUENCE: 30
ccacggaggt cttaaggcag                                               20

<210> SEQ ID NO 31
<211> LENGTH: 20
<212> TYPE: DNA
<213> ORGANISM: Artificial Sequence
<220> FEATURE:
<223> OTHER INFORMATION: LINC00473.v1 F1553

<400> SEQUENCE: 31
ctcctccttc tgacgggttt                                               20

<210> SEQ ID NO 32
<211> LENGTH: 21
```

<210> SEQ ID NO 32
<211> LENGTH: 21
<212> TYPE: DNA
<213> ORGANISM: Artificial Sequence
<220> FEATURE:
<223> OTHER INFORMATION: LINC00473.v2 F613 primer

<400> SEQUENCE: 32
gtcccactag gaaactgcga a                                        21

<210> SEQ ID NO 33
<211> LENGTH: 20
<212> TYPE: DNA
<213> ORGANISM: Artificial Sequence
<220> FEATURE:
<223> OTHER INFORMATION: LINC00473.v2 F939 primer

<400> SEQUENCE: 33
tgtaagccac gagttggaca                                          20

<210> SEQ ID NO 34
<211> LENGTH: 29
<212> TYPE: DNA
<213> ORGANISM: Artificial Sequence
<220> FEATURE:
<223> OTHER INFORMATION: tRNA-Glu probe

<400> SEQUENCE: 34
ccgaatccta accactagac caccaggga                                29

<210> SEQ ID NO 35
<211> LENGTH: 30
<212> TYPE: DNA
<213> ORGANISM: Artificial Sequence
<220> FEATURE:
<223> OTHER INFORMATION: snRNA U6 probe

<400> SEQUENCE: 35
gcaggggcca tgctaatctt ctctgtatcg                               30

<210> SEQ ID NO 36
<211> LENGTH: 20
<212> TYPE: DNA
<213> ORGANISM: Artificial Sequence
<220> FEATURE:
<223> OTHER INFORMATION: Lnc473_1 probe

<400> SEQUENCE: 36
tgtgaattct ctccagggcg                                          20

<210> SEQ ID NO 37
<211> LENGTH: 20
<212> TYPE: DNA
<213> ORGANISM: Artificial Sequence
<220> FEATURE:
<223> OTHER INFORMATION: Lnc473_2 probe

<400> SEQUENCE: 37
cgcagttttt catcgtgatg                                          20

<210> SEQ ID NO 38
<211> LENGTH: 20
<212> TYPE: DNA
<213> ORGANISM: Artificial Sequence
<220> FEATURE:
<223> OTHER INFORMATION: Lnc473_3 probe

<400> SEQUENCE: 38
caacacgccc tctcggaaag         20

<210> SEQ ID NO 39
<211> LENGTH: 20
<212> TYPE: DNA
<213> ORGANISM: Artificial Sequence
<220> FEATURE:
<223> OTHER INFORMATION: Lnc473_4 probe

<400> SEQUENCE: 39
ttagaaggtg gaaccgcctg         20

<210> SEQ ID NO 40
<211> LENGTH: 20
<212> TYPE: DNA
<213> ORGANISM: Artificial Sequence
<220> FEATURE:
<223> OTHER INFORMATION: Lnc473_5 probe

<400> SEQUENCE: 40
aatcaaccaa gactgtttca         20

<210> SEQ ID NO 41
<211> LENGTH: 20
<212> TYPE: DNA
<213> ORGANISM: Artificial Sequence
<220> FEATURE:
<223> OTHER INFORMATION: Lnc473_6 probe

<400> SEQUENCE: 41
ggccgagcat aaagtagtat         20

<210> SEQ ID NO 42
<211> LENGTH: 20
<212> TYPE: DNA
<213> ORGANISM: Artificial Sequence
<220> FEATURE:
<223> OTHER INFORMATION: Lnc473_7 probe

<400> SEQUENCE: 42
ggcagctact tgccaacaac         20

<210> SEQ ID NO 43
<211> LENGTH: 20
<212> TYPE: DNA
<213> ORGANISM: Artificial Sequence
<220> FEATURE:
<223> OTHER INFORMATION: Lnc473_8 probe

<400> SEQUENCE: 43
taatcaaggg cgcgtacaga         20

<210> SEQ ID NO 44
<211> LENGTH: 20
<212> TYPE: DNA
<213> ORGANISM: Artificial Sequence
<220> FEATURE:
<223> OTHER INFORMATION: Lnc473_9

<400> SEQUENCE: 44
gttaaaacac atgcagtgga         20

<210> SEQ ID NO 45
<211> LENGTH: 20
<212> TYPE: DNA
<213> ORGANISM: Artificial Sequence -continued

```
<220> FEATURE:
<223> OTHER INFORMATION: Lnc473_10 probe

<400> SEQUENCE: 45
tggcccaaat aaacgtggaa                                              20

<210> SEQ ID NO 46
<211> LENGTH: 20
<212> TYPE: DNA
<213> ORGANISM: Artificial Sequence
<220> FEATURE:
<223> OTHER INFORMATION: Lnc473_11 probe

<400> SEQUENCE: 46
actggatctt tgcagacagg                                              20

<210> SEQ ID NO 47
<211> LENGTH: 20
<212> TYPE: DNA
<213> ORGANISM: Artificial Sequence
<220> FEATURE:
<223> OTHER INFORMATION: Lnc473_12 probe

<400> SEQUENCE: 47
gcacgtagac tcaaatctgt                                              20

<210> SEQ ID NO 48
<211> LENGTH: 20
<212> TYPE: DNA
<213> ORGANISM: Artificial Sequence
<220> FEATURE:
<223> OTHER INFORMATION: Lnc473_13 probe

<400> SEQUENCE: 48
gtctttagta catttccagg                                              20

<210> SEQ ID NO 49
<211> LENGTH: 20
<212> TYPE: DNA
<213> ORGANISM: Artificial Sequence
<220> FEATURE:
<223> OTHER INFORMATION: Lnc473_14 probe

<400> SEQUENCE: 49
ttctttcagc aatatgttgt                                              20

<210> SEQ ID NO 50
<211> LENGTH: 20
<212> TYPE: DNA
<213> ORGANISM: Artificial Sequence
<220> FEATURE:
<223> OTHER INFORMATION: Lnc473_15 probe

<400> SEQUENCE: 50
tccgctttgc attcagaata                                              20

<210> SEQ ID NO 51
<211> LENGTH: 20
<212> TYPE: DNA
<213> ORGANISM: Artificial Sequence
<220> FEATURE:
<223> OTHER INFORMATION: Lnc473_16 probe

<400> SEQUENCE: 51
ccccaaaact gagcacataa                                              20
```

<210> SEQ ID NO 52
<211> LENGTH: 20
<212> TYPE: DNA
<213> ORGANISM: Artificial Sequence
<220> FEATURE:
<223> OTHER INFORMATION: Lnc473_17

<400> SEQUENCE: 52
cgtgacaatg actaagcctt                                               20

<210> SEQ ID NO 53
<211> LENGTH: 20
<212> TYPE: DNA
<213> ORGANISM: Artificial Sequence
<220> FEATURE:
<223> OTHER INFORMATION: Lnc473_18 probe

<400> SEQUENCE: 53
gggcaatggg taaaccttac                                               20

<210> SEQ ID NO 54
<211> LENGTH: 20
<212> TYPE: DNA
<213> ORGANISM: Artificial Sequence
<220> FEATURE:
<223> OTHER INFORMATION: Lnc473_19 probe

<400> SEQUENCE: 54
ataggacact cagctctcaa                                               20

<210> SEQ ID NO 55
<211> LENGTH: 20
<212> TYPE: DNA
<213> ORGANISM: Artificial Sequence
<220> FEATURE:
<223> OTHER INFORMATION: Lnc473_20 probe

<400> SEQUENCE: 55
aagttcttgg gcagcagaag                                               20

<210> SEQ ID NO 56
<211> LENGTH: 20
<212> TYPE: DNA
<213> ORGANISM: Artificial Sequence
<220> FEATURE:
<223> OTHER INFORMATION: Lnc473_21 probe

<400> SEQUENCE: 56
tgatttctcc agttaccacc                                               20

<210> SEQ ID NO 57
<211> LENGTH: 20
<212> TYPE: DNA
<213> ORGANISM: Artificial Sequence
<220> FEATURE:
<223> OTHER INFORMATION: Lnc473_22 probe

<400> SEQUENCE: 57
gagaatcccg cacaaccaag                                               20

<210> SEQ ID NO 58
<211> LENGTH: 20
<212> TYPE: DNA
<213> ORGANISM: Artificial Sequence
<220> FEATURE:
<223> OTHER INFORMATION: Lnc473_23 probe

```
<400> SEQUENCE: 58
gaaaacccgt cagaaggagg                                               20

<210> SEQ ID NO 59
<211> LENGTH: 20
<212> TYPE: DNA
<213> ORGANISM: Artificial Sequence
<220> FEATURE:
<223> OTHER INFORMATION: Lnc473_24 probe

<400> SEQUENCE: 59
agtgttcgac acagagtgtg                                               20

<210> SEQ ID NO 60
<211> LENGTH: 20
<212> TYPE: DNA
<213> ORGANISM: Artificial Sequence
<220> FEATURE:
<223> OTHER INFORMATION: Lnc473_25 probe

<400> SEQUENCE: 60
tgtctgcaca tcgctaatta                                               20

<210> SEQ ID NO 61
<211> LENGTH: 20
<212> TYPE: DNA
<213> ORGANISM: Artificial Sequence
<220> FEATURE:
<223> OTHER INFORMATION: Lnc473_26 probe

<400> SEQUENCE: 61
tggcattttt attcctgtaa                                               20

<210> SEQ ID NO 62
<211> LENGTH: 20
<212> TYPE: DNA
<213> ORGANISM: Artificial Sequence
<220> FEATURE:
<223> OTHER INFORMATION: Lnc473_27 probe

<400> SEQUENCE: 62
atgaatatga cttgggttct                                               20
```

LNCRNA SERVES AS A BIOMARKER AND THERAPEUTIC TARGET

CROSS-REFERENCE TO RELATED APPLICATIONS

This application is the U.S. national stage application of International Patent Application No. PCT/US2016/026897, filed Apr. 11, 2016, which claims the benefit of U.S. Provisional Application Ser. No. 62/145,825, filed Apr. 10, 2015, and U.S. Provisional Application Ser. No. 62/320,510, filed Apr. 9, 2016, the disclosures of which are hereby incorporated by reference in their entirety, including all figures, tables and amino acid or nucleic acid sequences.

The Sequence Listing for this application is labeled "Seq-List.txt" which was created on Apr. 9, 2016 and is 16 KB. The entire content of the sequence listing is incorporated herein by reference in its entirety.

The invention was made with government support under Grant No. CA187730 awarded by the National Institutes of Health. The government has certain rights in the invention.

BACKGROUND OF THE INVENTION

Lung cancer is the leading cause of cancer deaths in the United States and worldwide. The tumor suppressor gene Liver Kinase B1 (LKB1), also known as Serine/Threonine Kinase 11 (STK11), encodes a serine/threonine kinase that is critical for cellular metabolism, polarity and growth control. LKB1 gene is somatically inactivated in approximately 30% of non-small cell lung cancer (NSCLC) cases and third most frequently mutated gene in NSCLC. The loss of LKB1 in the context of Kirsten rat sarcoma viral oncogene (KRAS) mutations promotes lung cancer metastasis in mouse models and is associated with poor prognosis. The LKB1 status is linked with cancer responsiveness to several targeted agents and chemotherapy in mouse tumor models. LKB1 is thus implicated as diagnostic, prognostic and predictive biomarkers in human lung cancer. Moreover, LKB1 mutations have been observed in other tumor types such as ovarian cancers and cervical cancers, and are important for tumor progression. However, clinical benefits that exploit LKB1 deficiency cannot be achieved without studying the tumors produced by LKB1 loss of function.

BRIEF SUMMARY OF THE INVENTION

The invention provides a long intergenic non-coding RNA (lincRNA), namely, LINC00473, as a gene regulator of oncogenesis. Increased LINC00473 expression was observed in cells with downregulation of LKB1 protein expression/function and shown to have a critical role in carcinogenesis in the cells. Accordingly, an embodiment of the invention provides a method of diagnosing and treating a subject having a cancer involving loss or reduction in LKB1 function, the method comprising:
(a) determining the level of LINC00473 in:
  i) a test sample obtained from the subject, and
  ii) optionally a control sample;
(b) optionally obtaining a reference value corresponding to a level of LINC00473,
wherein the level of LINC00473 in the test sample relative to the control sample or the reference value indicates the presence or absence of the cancer involving loss or reduction in LKB1 function in the subject; and
(c) identifying the subject as having the cancer involving loss or reduction in LKB1 function based on the level of LINC00473 in the test sample and administering an effective amount of a LINC00473 inhibitor to the subject to treat the cancer, or
(d) identifying the subject as having the cancer not involving loss or reduction in LKB1 function based on the level of LINC00473 in the test sample and withholding the administration of the LINC00473 inhibitor to the subject, and optionally, administering a cancer therapy other than the LINC00473 inhibitor to the subject to treat the cancer.

The LINC00473 inhibitor can be an inhibitor of LINC00473 expression and/or activity, for example, a small-inhibitory RNA (siRNA), a short hairpin RNA, a bifunctional RNA, an antisense oligonucleotide, a ribozyme, a deoxyribozyme, an aptamer or a small molecule inhibitor. Accordingly, an embodiment of the invention provides a pharmaceutical composition comprising a LINC00473 for the treatment of a cancer, for example, a cancer involving loss or reduced LKB1 function or a cancer with high LINC00473 expression.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 4A-4F. shRNA-mediated LINC00473 knockdown in A549 lung cancer cells resulted in reduced cell proliferation and survival. Three independent lentiviral pLKO.1-based shLINC00473 were generated, including shLIN473-2: (AACTGGATCTTTGCAGACAGG, SEQ ID NO: 3); shLINC473-3 (AAAGATCCAGTTTAATACAGA, SEQ ID NO: 4); shLINC473-4 (AAGAACCCAAGTCATATTCAT, SEQ ID NO: 5). A549 (LKB1-null) cells were transduced with these lentiviruses and control viruses expressing scramble shRNA for 96 hours and harvested for evaluating LINC00473 expression by qRT-PCR (A), viable cell number counting by Trypan Blue assays (B), and apoptotic cells by Annexin V-PI staining (C). (D-F) A total of $2\times10^6$ A549-luc cells transduced with control shRNA or shLINC00473 (-2 & -4) were injected to NOD.SCID mice and the tumor growth was monitored via bioluminescence imaging (BLI) and direct tumor measurement. The tumors were photographed at day 36.

BRIEF DESCRIPTION OF THE SEQUENCES

Figure 1A:
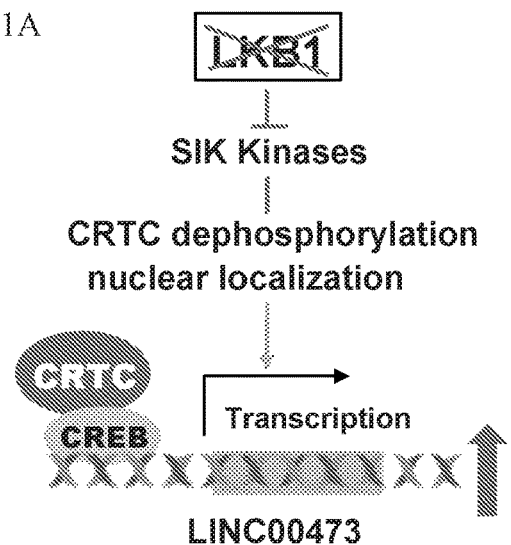
FIGS. 1A-1C. LINC00473 up-regulation is correlated with LKB1 loss in NSCLC cells. (A) LKB1 loss induces LINC00473 transcription through CRTC activation. (B, C) A panel of LKB1-null (red) and wild-type (wt) NSCLC cell lines were assayed for LKB1 protein levels via Western blotting (B) and LINC00473 expression via qRT-PCR (C).

SEQ ID NOs: 1-2: LINC00473 sequences.

SEQ ID NO: 3: Sequence of shLINC00473-2.

SEQ ID NO: 4: Sequence of shLINC00473-3.

SEQ ID NO: 5: Sequence of shLINC00473-4.

SEQ ID NOs: 6-62 for the sequences of primers and probes. Sequences are presented in the 5' to 3' direction.

| | Forward primer | Reverse primer | Amplicon (bp) |
|---|---|---|---|
| RT-PCR primers: Gene | | | |
| LINC00473 | AAACGCGAACGTGAGCCCCG (SEQ ID NO: 6) | CGCCATGCTCTGGCGCAGTT (SEQ ID NO: 7) | 134 |
| CREB | AGCAGCCACTCAGCCGGGTA (SEQ ID NO: 8) | ACGTCTCCAGAGGCAGCTTGAA (SEQ ID NO: 9) | 111 |
| ASNS | TGGCTGCCTTTTATCAGGGG (SEQ ID NO: 10) | TCTGCCACCTTTCTAGCAGC (SEQ ID NO: 11) | 153 |
| GAPDH | CAATGACCCCTTCATTGACC (SEQ ID NO: 12) | GACAAGCTTCCCGTTCTCAG (SEQ ID NO: 13) | 106 |
| CPS1 | GGAAATGTAGTTGCTTTCTTAACCTTTGATGATTTGTGGCATGGGC (SEQ ID NO: 14) | (SEQ ID NO: 15) | 73 |
| PDE4B | CCGATCGCATTCAGGTCCTTCGC (SEQ ID NO: 16) | TGCGGTCTGTCCATTGCCGA (SEQ ID NO: 17) | 96 |
| PTGS2 | GTTCCCACCCATGTCAAAAC (SEQ ID NO: 18) | CCGGTGTTGAGCAGTTTTCT (SEQ ID NO: 19) | 108 |
| PDE4D | CTCCTACGCGGTGGAGACC (SEQ ID NO: 20) | CATCAAAACGCCTGAGTCCC (SEQ ID NO: 21) | 92 |
| SLC7A2 | CAGTTGCTGCCACGTTGAC (SEQ ID NO: 22) | GGCTGGTACCTGAGGATGAG (SEQ ID NO: 23) | 148 |
| NEDD9 | GCTGCCGAAATGAAGTATAAGAATC (SEQ ID NO: 24) | CTTCCAGTCCCCCTGTGTTC (SEQ ID NO: 25) | 133 |
| CHIP-PCR primers: | | | |
| LINC00473 | AGCAGCCTTGCCAAAGGTC (SEQ ID NO: 26) | TTTCCCTTTAAGCCGGAGAT (SEQ ID NO: 27) | 163 |
| Primers for 5' RACE: | | | |
| LINC00473 R387 | | CCATGGAGAACTGCGCAAAG (SEQ ID NO: 28) | |
| LINC00473 R249 | | CTTCTCGCAAAAGGCGAGTG (SEQ ID NO: 29) | |
| Primers for 3' RACE: | | | |
| LINC00473.v1 F1382 | | CCACGGAGGTCTTAAGGCAG (SEQ ID NO: 30) | |
| LINC00473.v1 F1553 | | CTCCTCCTTCTGACGGGTTT (SEQ ID NO: 31) | |
| LINC00473.v2 F613 | | GTCCCACTAGGAAACTGCGAA (SEQ ID NO: 32) | |
| LINC00473.v2 F939 | | TGTAAGCCACGAGTTGGACA (SEQ ID NO: 33) | |
| Probes for Northern blotting analysis: | | | |
| tRNA-Glu | | CCGAATCCTAACCACTAGACCACCAGGGA (SEQ ID NO: 34) | |
| snRNA U6 | | GCAGGGGCCATGCTAATCTTCTCTGTATCG (SEQ ID NO: 35) | |
| Stellaris probes for RNA-FISH: | | | |
| Lnc473_1 | | TGTGAATTCTCTCCAGGGCG (SEQ ID NO: 36) | |
| Lnc473_2 | | CGCAGTTTTTCATCGTGATG (SEQ ID NO: 37) | |

-continued

| | |
|---|---|
| Lnc473_3 | CAACACGCCCTCTCGGAAAG (SEQ ID NO: 38) |
| Lnc473_4 | TTAGAAGGTGGAACCGCCTG (SEQ ID NO: 39) |
| Lnc473_5 | AATCAACCAAGACTGTTTCA (SEQ ID NO: 40) |
| Lnc473_6 | GGCCGAGCATAAAGTAGTAT (SEQ ID NO: 41) |
| Lnc473_7 | GGCAGCTACTTGCCAACAAC (SEQ ID NO: 42) |
| Lnc473_8 | TAATCAAGGGCGCGTACAGA (SEQ ID NO: 43) |
| Lnc473_9 | GTTAAAACACATGCAGTGGA (SEQ ID NO: 44) |
| Lnc473_10 | TGGCCCAAATAAACGTGGAA (SEQ ID NO: 45) |
| Lnc473_11 | ACTGGATCTTTGCAGACAGG (SEQ ID NO: 46) |
| Lnc473_12 | GCACGTAGACTCAAATCTGT (SEQ ID NO: 47) |
| Lnc473_13 | GTCTTTAGTACATTTCCAGG (SEQ ID NO: 48) |
| Lnc473_14 | TTCTTTCAGCAATATGTTGT (SEQ ID NO: 49) |
| Lnc473_15 | TCCGCTTTGCATTCAGAATA (SEQ ID NO: 50) |
| Lnc473_16 | CCCCAAAACTGAGCACATAA (SEQ ID NO: 51) |
| Lnc473_17 | CGTGACAATGACTAAGCCTT (SEQ ID NO: 52) |
| Lnc473_18 | GGGCAATGGGTAAACCTTAC (SEQ ID NO: 53) |
| Lnc473_19 | ATAGGACACTCAGCTCTCAA (SEQ ID NO: 54) |
| Lnc473_20 | AAGTTCTTGGGCAGCAGAAG (SEQ ID NO: 55) |
| Lnc473_21 | TGATTTCTCCAGTTACCACC (SEQ ID NO: 56) |
| Lnc473_22 | GAGAATCCCGCACAACCAAG (SEQ ID NO: 57) |
| Lnc473_23 | GAAACCCGTCAGAAGGAGG (SEQ ID NO: 58) |
| Lnc473_24 | AGTGTTCGACACAGAGTGTG (SEQ ID NO: 59) |
| Lnc473_25 | TGTCTGCACATCGCTAATTA (SEQ ID NO: 60) |
| Lnc473_26 | TGGCATTTTTATTCCTGTAA (SEQ ID NO: 61) |
| Lnc473_27 | ATGAATATGACTTGGGTTCT (SEQ ID NO: 62) |

DETAILED DISCLOSURE OF THE INVENTION

LKB1 is mutated and inactivated in a significant subset of lung cancer; however, accurate diagnostics and effective targeted therapeutics are not available for tumors involving inactivated LKB1. LncRNAs have emerged as a novel class of gene regulators and are implicated in tumorigenesis and progression. Reliable tests are needed to accurately identify tumors with loss of LKB1 function for patient stratification, to evaluate therapeutic responses and to assign individualized treatments.

LncRNAs are non-protein coding transcripts longer than 200 nucleotides and represent a novel class of gene regulators. The human genome encodes more than 10,000 lncRNAs and currently only a handful of lncRNAs have been characterized. LncRNA expression is frequently de-regulated in cancer, and shows cell or tissue specificity. They participate in cancer cell proliferation, survival, migration, and invasion, likely through exerting multiple regulatory functions at the transcriptional, post-transcriptional, and epigenetic levels. Targeting cancer-associated lncRNAs, such as HOX transcript antisense RNA (HOTAIR) and metastasis-associated lung adenocarcinoma transcript 1 (MALAT1), results in inhibitory effects on cancer cell growth and survival in vitro and tumor growth and metastasis in mouse models. Therefore, lncRNAs are critical for various stages of cancer development and progression, indicating that lncRNAs are novel therapeutic targets.

Figure 1B:
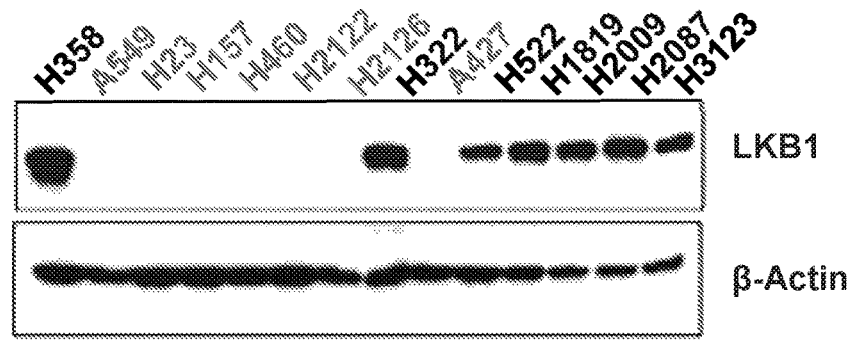
Figure 1C:
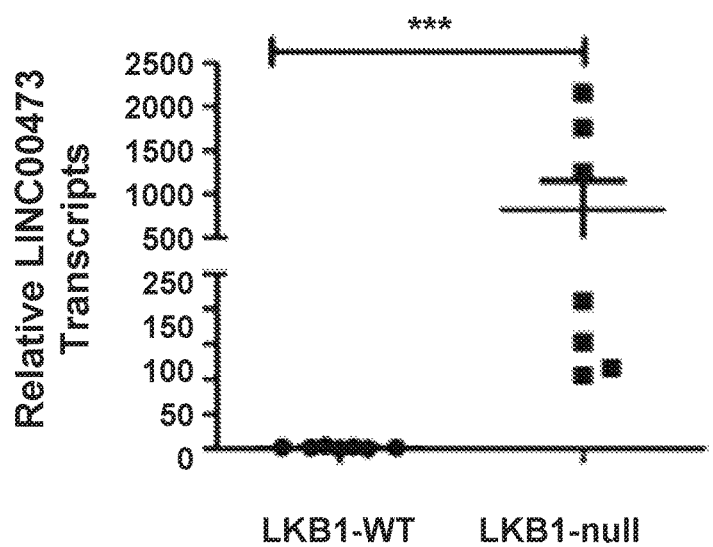
Figure 2A:
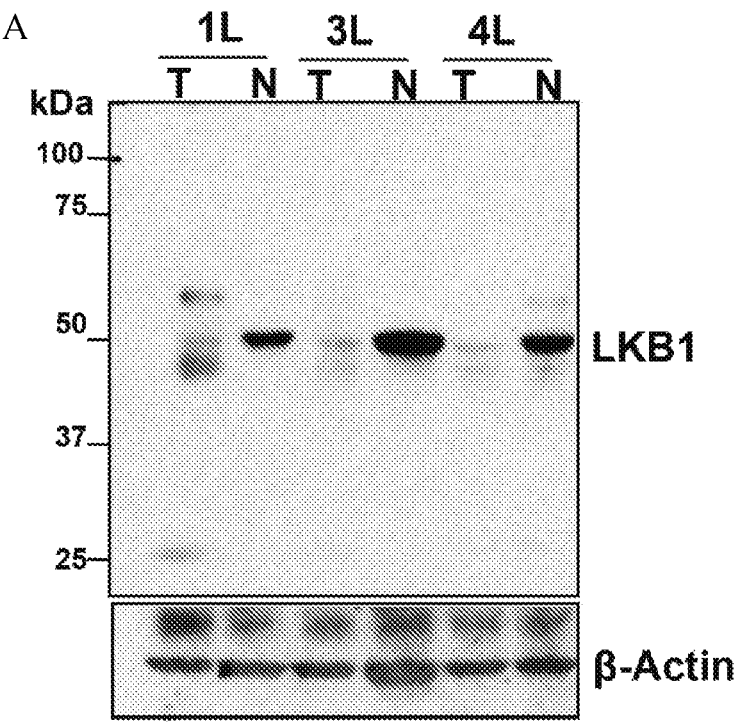
FIGS. 2A-2B. Human primary lung tumors and their matching normal tissues were analyzed for LKB1 protein expression via Western blotting and LINC00473 expression via real-time RT-PCR. Three human primary lung adenocarcinoma cases (1L, 3L and 4L) and their matching normal controls were assayed for LKB1 expression by Western blotting (A) and for LINC00473 expression by qRT-PCR (B). Tumors (T) and normal tissues (N) were indicated. For qRT-PCR, human LKB1-WT NSCLC H3123 cells served as a control with its LINC00473 expression value considered as 1, and fold change of LINC00473 expression normalized against that of H3123 was shown.
Figure 2B:
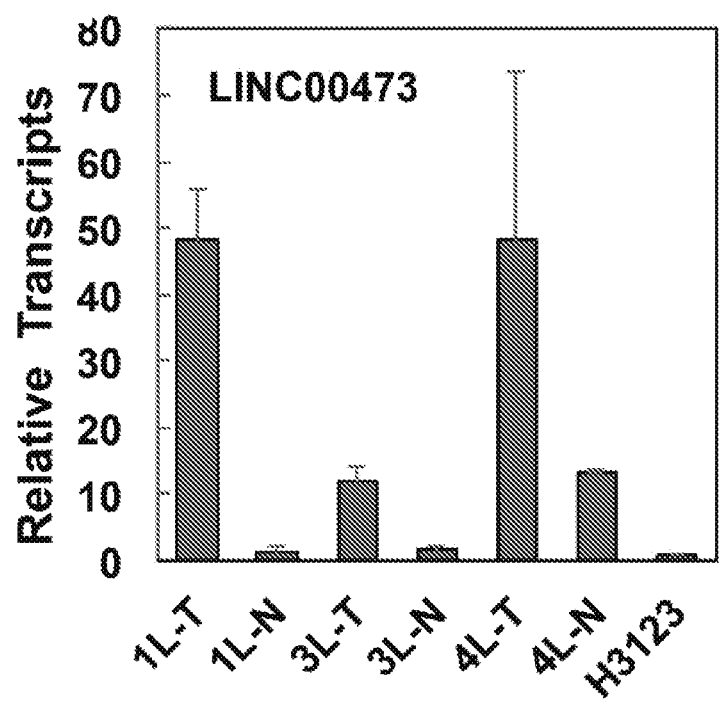
Figures 3A, 3B:
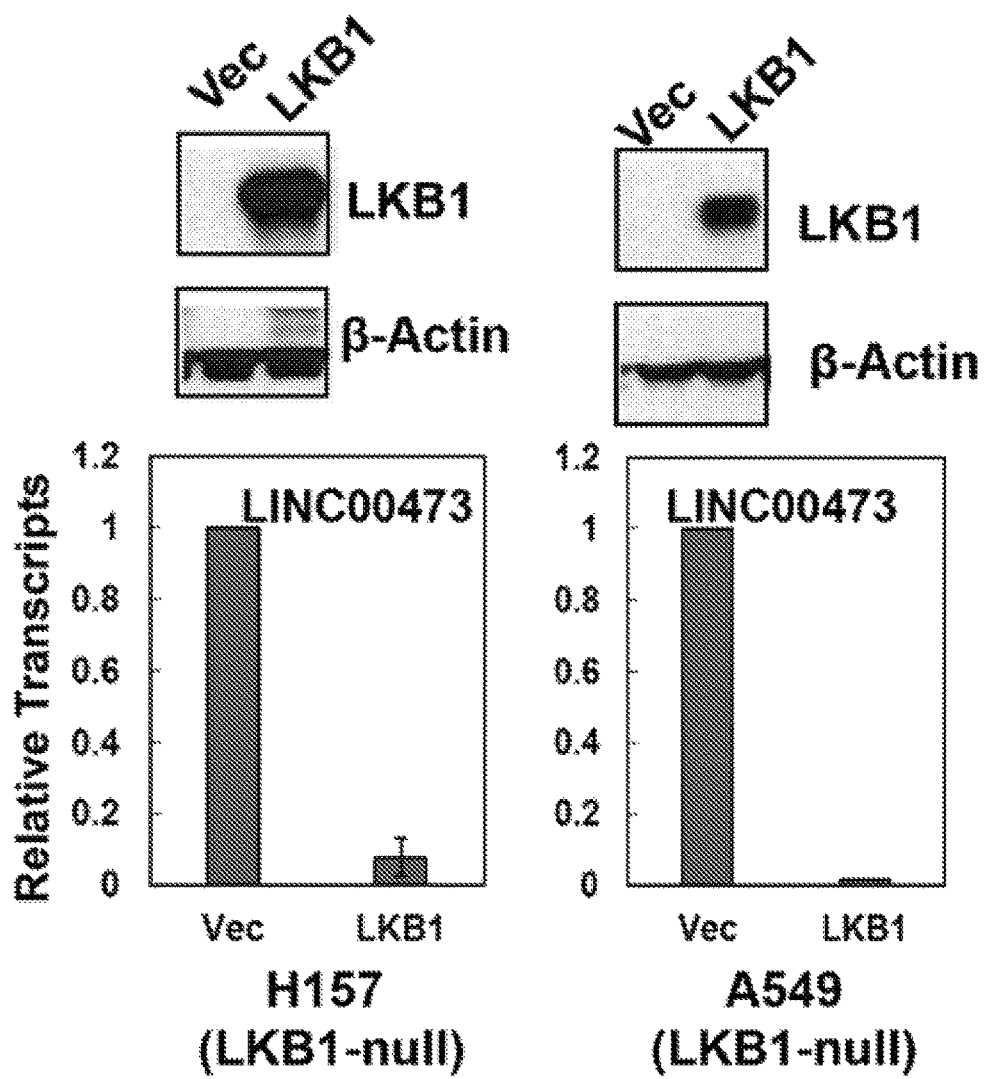
FIGS. 3A-3D. LINC00473 expression levels are negatively regulated by LKB1. (A, B) Retroviral-mediated LKB1 expression in LKB1-null NSCLC cells (H157 and A549) caused reduced LINC00473 expression. (C, D) Lentiviral-mediated LKB1 depletion in LKB1-wt NSCLC cells (H3123 and H322) resulted in enhanced LINC00473 expression. A similar effect was observed using an independent shRNA targeting LKB1. The upper panels present western blot analysis of LKB1 levels in either over-expressed or depleted cells, and the lower panels show the relative LINC00473 transcript levels, with the control defined as 1.
Figures 3C, 3D:
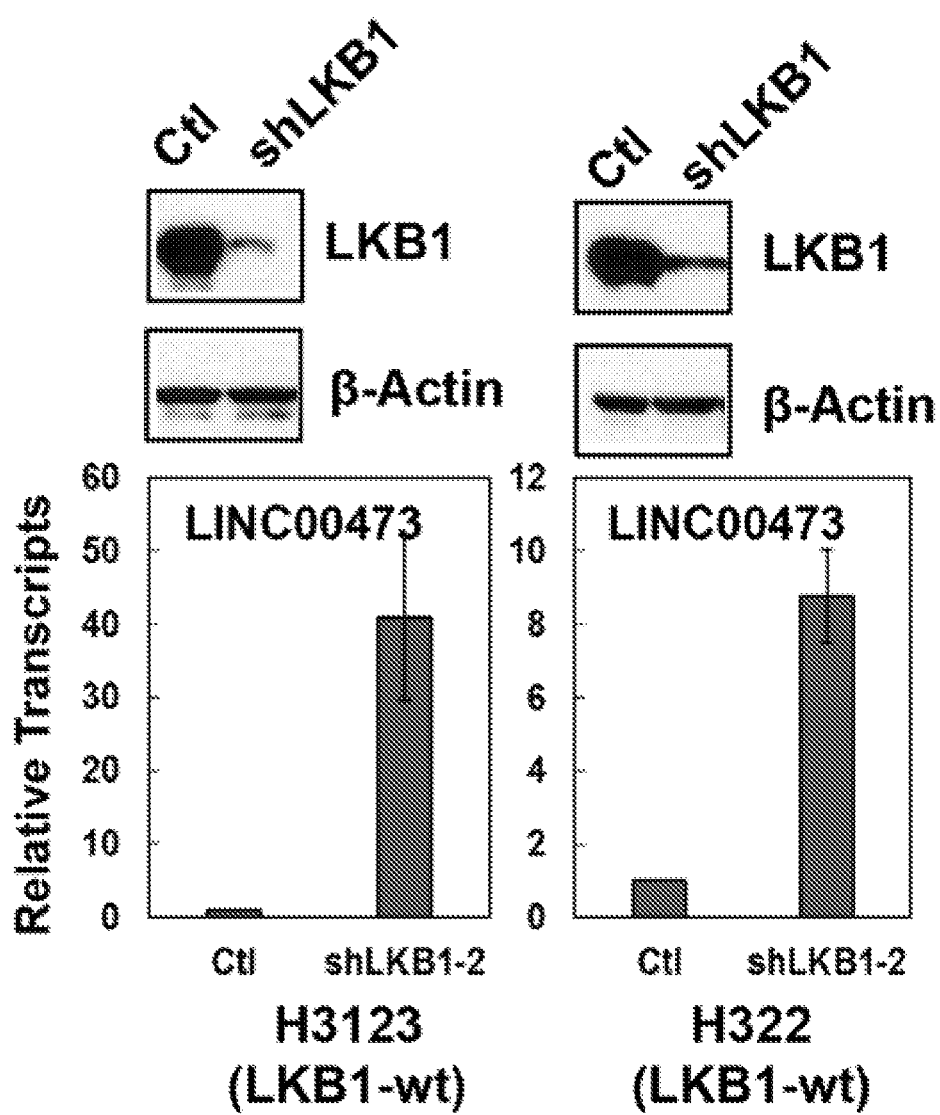
Figure 4A:
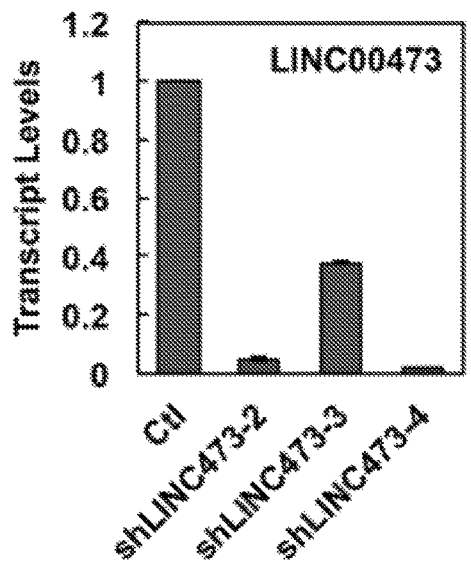
Figure 4B:
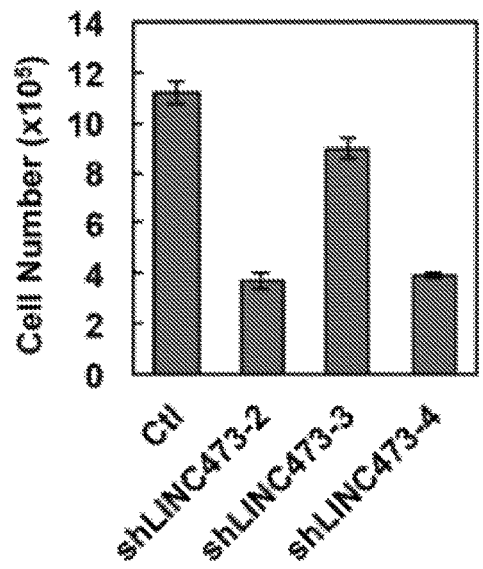
Figure 4C:
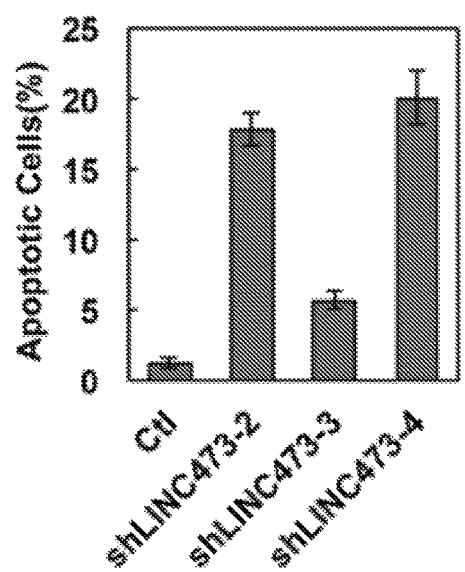

The mechanisms responsible for deregulated lncRNA levels in cancers are largely unknown. Enhanced transcription of LINC00473 (identified by SEQ ID NO: 1) was observed in human NSCLC cells with loss of LKB1 function (FIGS. 1-2). An inverse relationship was observed between LKB1 and LINC00473 expression in NSCLC cells, e.g., overexpression of LKB1 decreased LINC00473 expression, while LKB1 depletion enhanced LINC00473 expression (FIG. 3). LKB1 has multiple downstream targets and LKB1 negatively regulates the family of three CREB-regulated transcriptional co-activators (CRTC). LINC00473 is a CRTC/CREB target gene and its expression is up-regulated by loss of LKB1 signaling: (1) LINC00473 is transiently up-regulated in response to cAMP signaling in normal cells; (2) microarray analysis revealed LINC00473 as the top target for the CRTC1-MAML2 fusion oncogene that functionally mimics the activation of CRTC co-activators for the cAMP/CREB pathway; and (3) loss of LKB1 results in CRTC/CREB transcriptional activation in cancer cells. Therefore, LINC00473 can be transcriptionally up-regulated by CRTC activation upon LKB1 inactivation (FIG. 1A).

Accordingly, an embodiment of the invention provides assays to identify tumors with loss or reduction in LKB1 function and to further understand the molecular basis for LKB1 tumor suppressor and its clinical implications. The invention provides LINC00473 as a gene regulator of oncogenesis, a biomarker for LKB1-deficient tumors and an important mediator for LKB1-loss in lung cancer development and progression. Accordingly, an embodiment of the invention provides a method of treating a subject having a cancer involving loss or reduction in LKB1 function, the method comprising:

(a) determining the level of LINC00473 in:
  i) a test sample obtained from the subject, and
  ii) optionally, a control sample;
(b) optionally obtaining a reference value corresponding to a level of LINC00473, wherein the level of LINC00473 in the test sample relative to the control sample or the reference value indicates the presence or absence of the cancer involving loss or reduction in LKB1 function in the subject; and
(c) identifying the subject as having the cancer involving loss or reduction in LKB1 function based on the level of LINC00473 in the test sample and administering an effective amount of a LINC00473 inhibitor to the subject to treat the cancer, or
(d) identifying the subject as having the cancer not involving loss or reduction in LKB1 function based on the level of LINC00473 in the test sample and withholding the administration of the LINC00473 inhibitor to the subject, and optionally, administering a cancer therapy other than the LINC00473 inhibitor to the subject to treat the cancer.

Another embodiment provides assays to identify tumors with loss or reduction in LKB1 function. The invention provides LINC00473 as a gene regulator of oncogenesis, a biomarker for LKB1-deficient tumors and an important mediator for LKB1-loss in lung cancer development and progression. Accordingly, an embodiment of the invention provides a method of diagnosing a subject having a cancer involving loss or reduction in LKB1 function, the method comprising:

(a) determining the level of LINC00473 in:
  i) a test sample obtained from the subject, and
  ii) optionally, a control sample;
(b) optionally obtaining a reference value corresponding to a level of LINC00473, wherein the level of LINC00473 in the test sample relative to the control sample or the reference value indicates the presence or absence of the cancer involving loss or reduction in LKB1 function in the subject; and
(c) identifying the subject as having the cancer involving loss or reduction in LKB1 function based on the level of LINC00473 in the test sample and guide cancer treatment.
(d) identifying the subject as having the cancer not involving loss or reduction in LKB1 function based on the level of LINC00473 in the test sample and guide cancer treatment and, optionally,
(e) identifying the subject with enhanced level of LINC00473 in the test sample and administering an effective amount of a LINC00473 inhibitor to the subject to treat the cancer. With respect to steps (c) and (d), increased levels of LINC00473 are associated with a loss or reduction in LINC00473 function. Additionally, this method can be performed by measuring LINC00473 levels of SEQ ID NO: 1, SEQ ID NO: 2 or both SEQ ID NO:1 and SEQ ID NO: 2 in test samples and/or control samples.

As used herein, the terms "treat," "treating," or "treatment" and synonyms thereof refer to both therapeutic treatment measures, wherein the object is to slow down cancer development and/or spread of a cancer. For purposes of this invention, beneficial or desired clinical results include, but are not limited to, alleviation of symptoms in whole or in part, diminishment of extent of disease, stabilized (i.e., not worsening) state of disease, delay or slowing of disease progression, amelioration or palliation of the disease state, and remission (whether partial or total), whether detectable or undetectable. Complete absence of the cancer is not required for effective treatment.

For the purposes of the invention, the phrase "a cancer involving loss or reduction in LKB1 function" refers to a cancer in which the cancer cells exhibit loss or reduction in the activity of LKB1 protein. Loss or reduction in LKB1 protein activity can arise from, for example, loss or reduction in LKB1 gene expression, loss or reduction in LKB1 mRNA translation, increased degradation of LKB1 mRNA, reduced stability of LKB1 mRNA, loss or reduction in LKB1 protein activity, increased degradation of LKB1 protein, reduced stability of LKB1 protein or mutation in LKB1 protein. Additional examples of molecular mechanism which can lead to loss or reduction in LKB1 protein activity are well known to a person of ordinary skill in the art and such embodiments are within the purview of the invention.

For the purposes of the invention, the phrase "a cancer not involving loss or reduction in LKB1 function" refers to a cancer in which the cancer cells exhibit LKB1 protein activity which is not different than non-cancerous cells from the same tissue. In such cancers, the cancer arises from other mechanisms of carcinogenesis.

In certain embodiments, the control sample and the test sample are obtained from the same type of an organ or tissue. Non-limiting examples of the organ or tissue which can be used as samples are brain, eyes, pineal gland, pituitary gland, thyroid gland, parathyroid glands, thorax, heart, lung, esophagus, thymus gland, pleura, adrenal glands, appendix, gall bladder, urinary bladder, large intestine, small intestine, kidneys, liver, pancreas, spleen, stoma, ovaries, prostate, testis, uterus, skin, or blood. Additional examples of organs and tissues are well known to a person of ordinary skill in the art and such embodiments are within the purview of the invention. In one embodiment, a lung sample is obtained.

In certain other embodiments, the control sample and the test sample are obtained from the same type of a body fluid. Non-limiting examples of the body fluids which can be used as samples include amniotic fluid, aqueous humor, vitreous humor, bile, blood, cerebrospinal fluid, chyle, endolymph, perilymph, female ejaculate, lymph, mucus (including nasal drainage and phlegm), pericardial fluid, peritoneal fluid, pleural fluid, pus, rheum, saliva, sputum, synovial fluid, vaginal secretion, blood, serum or plasma. Additional examples of body fluids are well known to a person of ordinary skill in the art and such embodiments are within the purview of the invention. In one embodiment, pleural fluid is obtained.

For the purposes of this application, the subject is a mammal. Non-limiting examples include human, ape, canine, pig, bovine, rodent, or feline subjects. In one embodiment, the methods described herein are used to identify a human as having a cancer involving loss or reduction in LKB1 function.

To practice the methods described herein for identifying a subject as having a cancer involving loss or reduction in LKB1 function, control samples can be obtained from one or more of the following:

a) an individual belonging to the same species as the subject and not having cancer, b) an individual belonging to the same species as the subject and known to have a cancer not involving loss or reduction in LKB1 function, c) the subject prior to having a cancer, or d) an individual belonging to the same species as the subject and known to have a cancer involving loss or reduction in LKB1 function. Additional examples of control samples appropriate for use in the methods described herein are well known to a person of ordinary skill in the art and such embodiments are within the purview of the current invention.

The term "the presence of LINC00473 relative to that of the control sample" indicates that the level of LINC00473 when compared to that of the control sample is used to identify a subject as having or not having a cancer involving loss or reduction in LKB1 function. In one embodiment, a subject is identified as having a cancer involving loss or reduction in LKB1 function if the level of LINC00473 in a test sample is higher than the level of LINC00473 in a control sample obtained from an individual belonging to the same species as the subject and not having cancer, an individual belonging to the same species as the subject and known to have a cancer not involving loss or reduction in LKB1 function or the subject prior to having a cancer.

In certain embodiments, a subject is identified as having a cancer involving loss or reduction in LKB1 function if the level of LINC00473 in the test sample is about 1 to 100 times, about 5 to 80 times, or about 10 to 50 times higher than the level of LINC00473 in the control sample obtained from an individual belonging to the same species as the subject and not having cancer, an individual belonging to the same species as the subject and known to have a cancer not involving loss or reduction in LKB1 function, or the subject prior to having a cancer.

In further embodiments, a subject is identified as having a cancer involving loss or reduction in LKB1 function if the level of LINC00473 in the test sample is about 1.5, 2, 3, 4, 5, 6, 7, 8, 9, 10, 15, 20, 25, 30, 35, 40, 45, 50, 55, 60, 65, 70, 75, 80, 85, 90, 95 or 100 times higher than the level of LINC00473 in the control sample obtained from an individual belonging to the same species as the subject and not having cancer, an individual belonging to the same species as the subject and known to have a cancer not involving loss or reduction in LKB1 function, or the subject prior to having a cancer.

In another embodiment, a subject is identified as having a cancer involving loss or reduction in LKB1 function if the level of LINC00473 in a test sample is not different than the level of LINC00473 in a control sample obtained from an individual belonging to the same species as the subject and known to have a cancer involving loss or reduction in LKB1 function.

The term "the presence of LINC00473 relative to the reference value" indicates that the level of LINC00473 when compared to the reference value is used to identify a subject as having a cancer involving loss or reduction in LKB1 function. The reference value corresponding to the level of LINC00473 can indicate the level of LINC00473 associated with the absence of a cancer, the presence of a cancer not involving loss or reduction in LKB1 function or the presence of a cancer involving loss or reduction in LKB1 function. As such, the reference values corresponding to the level of LINC00473 may be indicative of the absence of a cancer, the presence of a cancer not involving loss or reduction in LKB1 function or the presence of a cancer involving loss or reduction in LKB1 function.

A reference value associated with absence of a cancer may be obtained based on the level of LINC00473 in the samples obtained from individuals known to have the absence of cancer. A reference value associated a cancer not involving loss or reduction in LKB1 function may be obtained based on the level of LINC00473 in the individuals known to have a cancer not involving loss or reduction in LKB1 function. A reference value associated with a cancer involving loss or reduction in LKB1 function may be obtained based on the level of LINC00473 in the samples obtained from individuals known to a cancer involving loss or reduction in LKB1 function.

For example, tissues from a group of healthy individuals can be obtained and LINC00473 level can be determined which indicates a reference value associated with the absence of a cancer. Similarly, tissues from individuals known to have a cancer not involving loss or reduction in LKB1 function can be obtained and LINC00473 level can be determined which indicates a reference value associated with the presence of a cancer not involving loss or reduction in LKB1 function. Further, tissues from individuals known to have a cancer involving loss or reduction in LKB1 function can be obtained and LINC00473 level can be determined which indicates a reference value associated with the presence of a cancer involving loss or reduction in LKB1 function. Additional examples of determining references values associated with the absence of cancer, presence of a cancer not involving loss or reduction in LKB1 function or presence of a cancer involving loss or reduction in LKB1 function are well known to a person of ordinary skill in the art and such embodiments are within the purview of the invention.

Based on the reference value used and the level of LINC00473 in a test sample, a subject can be identified as having a cancer involving a loss or reduction in LKB1 function. For example, a subject is identified as having a cancer involving loss or reduction in LKB1 function if the level of LINC00473 in the test sample is higher than the reference value corresponding to a cancer not involving loss or reduction in LKB1 function. Alternately, a subject is identified as having a cancer involving loss or reduction in LKB1 function if the level of LINC00473 in the test sample is not different than the reference value corresponding to a cancer involving loss or reduction in LKB1 function.

The step of determining the level of LINC00473 can be performed by a variety of techniques well-known to a person of ordinary skill in the art. In an embodiment, the step of determining the level of LINC00473 comprises contacting the sample with selective reagents such as probes, primers or ligands, and thereby detecting the presence, or measuring the amount, of nucleic acids of interest originally in the sample. Contacting may be performed in any suitable device, such as a plate, microtiter dish, test tube, well, glass, column, and so forth.

In one embodiment, the contacting is performed on a substrate coated with the reagent, such as a nucleic acid array or chip or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or proteins of the sample.

In a preferred embodiment, the expression level may be determined by determining the quantity of mRNA. Methods for quantifying mRNA are well known in the art. The test sample and optionally, the control sample, can be appropriately treated for producing of a RNA preparation used in the contacting step. For example, a sample can be homogenized and proteins and DNA can be removed from the sample, for example, through degradation or precipitation, to purify RNA from the sample. Various techniques of isolating RNA from a sample are well known to a person of ordinary skill in the art and such embodiments are within the purview of the current invention.

LINC00473 contained in the samples (e.g., cell or tissue prepared from the patient) can be detected by hybridization (e. g., Northern blot analysis, RNA in situ hybridization) and/or amplification (e.g., reverse transcriptase-polymerase chain reaction (RT-PCR)). Preferably quantitative or semi-quantitative RT-PCR and RNA hybridization are preferred since they are particularly advantageous. Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to LINC00473 find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, and enzymatic or other labels (e.g., avidin/biotin).

Probes typically comprise single-stranded nucleic acids of between 10 to 200 nucleotides in length, for instance of between 10 and 100, more preferably of between 15 and 80, typically of between 20 and 25. Primers typically are shorter single-stranded nucleic acids, of between 10 to 25 nucleotides in length, designed to perfectly or almost perfectly match a nucleic acid of interest, to be amplified, i.e., LINC00473. The probes and primers are "specific" to the nucleic acids to which they hybridize, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used herein may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the level of LINC00473, a sample from a test subject, optionally first subjected to a reverse transcription, is labelled and contacted with the microarray under hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see, for example, the review by Hoheisel, 2006).

If a subject is identified as having a cancer involving loss or reduction in LKB function or having a cancer with high LINC00473 expression, a LINC00473 inhibitor is administered to the subject to treat the cancer. For the purposes of this invention, the terms "LINC00473 inhibitor" or "inhibitor of LINC00473" refers to an agent capable of inhibiting the expression and/or activity of LINC00473. The LINC00473 inhibitor can be an siRNA, shRNA, bifunctional RNA, antisense oligonucleotide, ribozyme, deoxyribozyme, aptamer or small molecule inhibitor.

The sequence of siRNA, shRNA, a bifunctional RNA, antisense oligonucleotide, ribozyme, deoxyribozyme or aptamer as the LINC00473 inhibitor can be designed based on the sequence of LINC00473 provided in SEQ ID NO: 1. Certain examples of computer programs which can be used to design LINC00473 inhibitor based on the sequence of LINC00473 are provided in Naito et al. The Naito et al. reference is incorporated herein in its entirety. Additional examples of computer programs which can be used to design LINC00473 inhibitor based on the sequence of LINC00473 are well known to a person of ordinary skill in the art and such embodiments are within the purview of the invention.

Certain examples of inhibitors of non-coding RNAs (ncRNAs), for example, inhibitors of lincRNAs, are provided in Ling et al. and Li et al. The Ling et al. reference is incorporated herein by reference in its entirety, particularly, page 859, under "lncRNAs in cancer and therapeutic implications" to the end of page 862. The Li et al. reference is also incorporated herein by reference in its entirety, particularly, page 1902, right column, under "Prospective strategies for targeting lncRNAs" to the end of page 1907.

In one embodiment, the inhibitor of LINC00473, for example, an siRNA, shRNA, bifunctional RNA, antisense oligonucleotide, ribozyme, deoxyribozyme or aptamer is encoded by a nucleic acid vector. Accordingly, an embodiment of the invention provides a vector comprising a LINC00473 inhibitor.

In another embodiment, the LINC00473 inhibitor encoded by a nucleic acid is introduced to a subject via gene therapy. For example, the vector encoding the LINC00473 inhibitor encoded by a nucleic acid vector can be introduced specifically in to the cancer cells of a subject.

Examples of viral vectors and procedures for gene therapy using the viral vectors are described in Waehler et al. The Waehler et al. reference is incorporated herein in its entirety. Examples of non-viral vectors and procedures for gene therapy using the non-viral vectors are described in Yin et al. The Yin et al. reference is incorporated herein in its entirety. Certain examples of introducing nucleic acid inhibitors of a target nucleotide are provided in Ling et al., particularly, page 855, under "Restoring miRNA levels with oligonucleotide-based approaches" to the end of page 857. Additional examples of techniques used to introduce a nucleic acid inhibitor of LINC00473 in to cancer cells via gene therapy are provided in Amer and such embodiments are within the purview of the invention. The Amer reference is also incorporated herein in its entirety, particularly, page 2, under Method of Gene Therapy to page 6, right column, first paragraph.

A small molecule LINC00473 inhibitor can be obtained based on a screening of a compound library to identify specific compounds as LINC00473 inhibitor. Description of small molecule inhibitors of specific target oligonucleotides are provided in in Ling et al., for example, page 858, under Small molecules targeting miRNAs and Li et al., page 1905, under small molecules continuing on to page 1906.

A further an embodiment of the invention provides a pharmaceutical composition comprising a LINC00473 inhibitor. The pharmaceutical composition can be used for the treatment of a cancer, for example, a cancer involving loss or reduced LKB1 function.

Pharmaceutical compositions, as disclosed herein, can be formulated in accordance with standard pharmaceutical practice known by a person skilled in the art (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Compositions for parenteral administration are generally physiologically compatible sterile solutions or suspensions which can optionally be prepared immediately before use from solid or lyophilized form. Adjuvants such as a local anesthetic, preservative and buffering agents can be dissolved in the vehicle and a surfactant or wetting agent can be included in the composition to facilitate uniform distribution of the active ingredient.

For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered material, may also be necessary. For example, starch, gelatin, sugars such as lactose or dextrose, and natural or synthetic gums can be used as binders.

Disintegrants may also be necessary in the tablets to facilitate break-up of the tablet. Disintegrants include starches, clays, celluloses, aligns, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The LINC00473 inhibitor can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. In a particular embodiment, the method of treating lung cancer comprises administering to a subject in need thereof, a composition comprising LINC00473 inhibitor via inhalation.

Compositions of the invention appropriate for administration via inhalation can be a solution, suspension, or powder. These formulations are typically administered via an aerosol or a dry powder inhaler. Aerosol is a colloidal suspension of particles dispersed in air or gas. In aerosols, liquid or suspension droplets are the internal phase and a gas is the external phase.

In one embodiment, an aerosol delivery device is used to administer the compositions of the invention. An aerosol delivery device is used to produce aerosols, for example, for delivery to a subject via inhalation. Metered dose inhalers (MDI) are aerosol delivery devices that deliver a fixed dose in a spray with each actuation of the device.

In certain embodiments, atomizers, nebulizers, or vaporizers are used as aerosol delivery devices. Additional examples of aerosol delivery devices are well known to a person of ordinary skill in the art and such embodiments are within the purview of the current invention.

Atomizers break up a liquid into an aerosol. Typically, an atomizer comprises a squeeze bulb which is used to blow air into the device causing the drug solution to rise in a small dip tube and vaporizing in the air stream. The air stream is directed into a baffle or bead which breaks the droplets in to even smaller droplets as they collide with the device. The mixture of air and liquid then exits the atomizer in the form of an aerosol.

A nebulizer contains an atomizing unit within a chamber. When the rubber bulb is depressed, the medication solutions is drawn up a dip tube and aerosolized by the passing air stream. Baffles or beads may also be present in the chamber. The fine droplets exit the nebulizer. The larger droplets collect on the chamber and fall back into the reservoir where they can be used again. Vaporizers produce a fine mist of steam. Volatile medication is added to the water in the vaporizer or to a special medication cup present in some models. The medication volatilizes and is inhaled by a patient as he/she breathes.

In one embodiment, the composition is a dry powder and the inhalers contain the dry powders in cartridges or disks. When a patient administers a dose, the device is first activated by some mechanical motion and the dry powder becomes ready for inspiration. The patient then inhales through the device mouthpiece and the powder is drawn into the pulmonary tract along with the inspired air. These devices have overcome a major problem of inhalation therapy, synchronizing deep inspiration with the administration of the drug. Some of the commercially available devices are Diskhaler®, Turbuhaler®, Diskus®, and Rotahaler®.

In a further embodiment, a powdered composition is administered with insufflators or puffers. Squeezing the rubber bulb of an insufflator causes turbulence within the powder reservoir which forces some of the powder into the air stream and out of the device. A puffer is a plastic accordion-shaped container with a spout on one end. The powder is placed inside the container and the puffer is actuated by squeezing the device. A portion of the powder is ejected from the spout.

Additional devices appropriate for administration of the composition of the claimed invention via inhalation are well known to a person of ordinary skill in the art and such embodiments are within the purview of the invention. For example, Advanced Drug Delivery Reviews (2014), Volume 75, Pages 1-148 contains several articles directed to "Improving the efficacy of inhaled drugs for severe lung diseases: emerging pulmonary delivery strategies." The contents of these articles are herein incorporated by reference in their entirety, particularly, Angelo et al., "Improving the efficacy of inhaled drugs in CF: Challenges and emerging drug delivery strategies." Certain devices and methods for delivery of therapeutic substances via inhalation are also described "A Guide to Aerosol Delivery Devices for Respiratory Therapists, 3rd Edition (2013)" published by American Association for Respiratory Care, the contents of which are incorporated herein by reference in their entirety.

In one embodiment, the LINC00473 inhibitor is formulated in a composition wherein the LINC00473 inhibitor is specifically delivered to the cancer cells in the subject. Examples of specifically delivering an agent to target cells, for example, target cancer cells are described in the Erkki Ruoslahti et al. (2010) reference which is incorporated herein by reference in its entirety.

The LINC00473 inhibitor according to the present invention may be administered in effective amount to a subject in one or more "unit doses." Unit dose is defined as containing a predetermined-quantity of the therapeutic composition calculated to produce the desired responses upon administration to a subject, i.e., the appropriate route and treatment regimen. A quantity to be administered and a route of administration can be determined by a person of ordinary skill in the art depending upon the LINC00473 inhibitor to be administered and the status of cancer in a subject. For example, the subject to be treated may be evaluated, in particular, for the state of the subject's cancer, subjects overall health, age and desired aggressiveness of the therapy. Unit dose of the LINC00473 inhibitors may be described in terms of mg LINC00473 inhibitor per Kg of body weight, which can be about 0.05, 0.10, 0.15, 0.20, 0.25, 0.5, 1, 10, 50, 100, 1,000, or more.

A unit dose may be administered as a single dose or may be provided via multiple administrations over a predetermined period of time, for example, about one month to about six months, about two months to about five months, or about three to four months.

The term "effective amount" in connection with the LINC00473 inhibitor means an amount capable of alleviating symptoms of a cancer in whole or in parts, diminishment of extent of cancer, stabilized (i.e., not worsening) state of cancer, delaying or slowing of cancer progression, amelioration or palliation of the cancer state, and remission (whether partial or total), whether detectable or undetectable. Complete absence of the cancer may not be achieved by an effective amount of LINC00473 inhibitor.

LINC00473 inhibitor can be administered via different routes of administration. Non-limiting examples of routes of administration include oral, subcutaneous, intradermal, intravenous, intra-arterial, intratumoral, intraperitoneal, inhalation and intramuscular.

In a further embodiment of the invention, the LINC00473 inhibitor is administered to a subject identified as having a cancer involving loss or reduction in LKB1 function in combination with one or more additional cancer therapies. The additional cancer therapy can be selected from radiotherapy, chemotherapy, surgery, immunotherapy, kinase inhibition, monoclonal antibody therapy (e.g., bevacizumab or cetuximab) or a combination thereof. A cancer therapy in addition to the LINC00473 inhibitor to be administered can be determined by a person of ordinary skill in the art depending upon the status of cancer in a subject, for example, the subject to be treated may be evaluated, in particular, for the state of the subject's cancer, subjects overall health, age and desired aggressiveness of the therapy.

Non-limiting examples of the additional cancer therapy or the cancer treatments other than a LINC00473 inhibitor include, but are not limited to, administering one or more of: Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Adriamycin (Doxorubicin Hydrochloride), Adrucil (Fluorouracil), Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bleomycin, Bortezomib, Bosulif (Bosutinib), Bosutinib, Brentuximab Vedotin, Cabazitaxel, Cabozantinib-S-Malate, CAF, Campath (Alemtuzumab), Camptosar (Irinotecan, ydrochloride), Capecitabine, CAPDX, Carboplatin, CARBOPLATIN-TAXOL, Carfilzomib, CeeNU (Lomustine), Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, Cosmegen (Dactinomycin), Crizotinib, CVP (COP), Cyclophosphamide, Cyfos (Ifosfamide), Cytarabine, Cytarabine, Liposomal, Cytosar-U (Cytarabine), Cytoxan (Cyclophosphamide), Dacarbazine, Dacogen, (Decitabine), Dactinomycin, Dasatinib, Daunorubicin Hydrochloride, Decitabine, Degarelix, Denileukin, diftitox, Denosumab, DepoCyt (Liposomal Cytarabine), DepoFoam (Liposomal Cytarabine), Dexrazoxane hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRINOX, FOLFOX, Folotyn (Pralatrexate), FU-LV, Fulvestrant, Gardasil (Recombinant HPV Quadrivalent Vaccine), Gefitinib, Gemcitabine Hydrochloride, GEMCITABINE-CISPLATIN, Gemtuzumab Ozogamicin, Gemzar (Gemcitabine, ydrochloride), Gleevec (Imatinib Mesylate), Glucarpidase, Halaven (Eribulin Mesylate), Herceptin (Trastuzumab), HPV Bivalent Vaccine, Recombinant, HPV Quadrivalent Vaccine (Recombinant), Hycamtin (Topotecan Hydrochloride), Ibritumomab Tiuxetan, ICE, Iclusig (Ponatinib Hydrochloride), Ifex (Ifosfamide), Ifosfamide, Ifosfamidum (Ifosfamide), Imatinib Mesylate, Imiquimod, Inlyta (Axitinib), Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic (Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine hydrochloride), Mutamycin (Mitomycin C), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Ofatumumab, Omacetaxine, Mepesuccinate, Oncaspar (Pegaspargase), Ontak (Denileukin Diftitox), Oxaliplatin, Paclitaxel, Paclitaxel Albumin-stabilized Nanoparticle Formulation, Palifermin, Palonosetron Hydrochloride, Panitumumab, Paraplat (Carboplatin), Paraplatin (Carboplatin), Pazopanib Hydrochloride, Pegaspargase, Pemetrexed Disodium, Perjeta (Pertuzumab), Pertuzumab, Platinol (Cisplatin), Platinol-AQ (Cisplatin), Plerixafor, Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Raloxifene hydrochloride, Rasburicase, R-CHOP, R-CVP, Recombinant HPV Bivalent Vaccine, Recombinant HPV, Quadrivalent Vaccine, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Synovir (Thalidomide), Synribo (Omacetaxine Mepesuccinate), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and I 131 Iodine Tositumomab, Totect (Dexrazoxane Hydrochloride), Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELOX, Xgeva (Denosumab), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoledronic Acid, Zolinza (Vorinostat), Zometa (Zoledronic Acid), and Zytiga (Abiraterone Acetate).

The methods of current invention can be practiced to identify subjects having a cancer involving loss or reduction in LKB1 function, and optionally, for treating cancer, wherein the cancer is selected from acute lymphoblastic leukemia, acute myeloid leukemia, adrenocortical carcinoma, AIDS-related cancers, AIDS-related lymphoma, anal cancer, appendix cancer, astrocytoma, cerebellar astrocytoma, basal cell carcinoma, bile duct cancer, extrahepatic bladder cancer, bladder cancer, bone cancer, osteosarcoma and malignant fibrous histiocytoma, brain stem glioma, brain tumor, central nervous system embryonal tumors, cerebral astrocytoma/malignant glioma, ependymoblastoma, medulloblastoma, medulloepithelioma, pineal parenchymal tumors of intermediate differentiation, supratentorial primitive neuroectodermal tumors and pineoblastoma, visual pathway and hypothalamic glioma, brain and spinal cord tumors, breast cancer, bronchial tumors, Burkitt lymphoma, carcinoid tumor, gastrointestinal cancer, carcinoma of head and neck, central nervous system embryonal tumors, central nervous system lymphoma, cervical cancer, chordoma, chronic lymphocytic leukemia, chronic myelogenous leukemia, chronic myeloproliferative disorders, colorectal cancer, cutaneous T-cell lymphoma, embryonal tumors, endometrial cancer, ependymoblastoma, ependymoma, esophageal cancer, ewing family of tumors, extracranial germ cell tumor, extrahepatic bile duct cancer, eye Cancer, intraocular melanoma, retinoblastoma, gallbladder cancer, gastric (stomach) cancer, gastrointestinal carcinoid tumor, gastrointestinal stromal tumor (GIST), extracranial germ cell tumor, germ cell tumor, extragonadal germ cell tumor, ovarian, gestational trophoblastic tumor, glioma, brain stem glioma, hairy cell leukemia, head and neck cancer, hepatocellular (liver) cancer, hepatocellular (liver) cancer, Hodgkin lymphoma, hypopharyngeal cancer, hypothalamic and visual pathway glioma, intraocular melanoma, islet cell tumors (endocrine pancreas), Kaposi sarcoma, kidney (renal cell) cancer, kidney cancer, laryngeal cancer, chronic lymphocytic leukemia, chronic leukemia, myelogenous leukemia, lip and oral cavity cancer, lung cancer, non-small cell lung cancer, small cell lymphoma, AIDS-related lymphoma, Burkitt lymphoma, cutaneous T-cell lymphoma, non-Hodgkin lymphoma, macroglobulinemia, Waldenström macroglobulinemia, malignant fibrous histiocytoma of bone and osteosarcoma, medulloblastoma, medulloepithelioma, melanoma, intraocular Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia, multiple myeloproliferative disorders, nasal cavity and paranasal sinus cancer, nasopharyngeal cancer, neuroblastoma, non-Small cell lung cancer, oral cancer, oral cavity cancer, lip and oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, pancreatic cancer, islet cell tumors, papillomatosis, paranasal sinus and nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, breast cancer, primary central nervous system lymphoma, prostate cancer, rectal cancer, renal pelvis and ureter cancer, transitional cell cancer, respiratory tract carcinoma involving the NUT gene on chromosome 15, retinoblastoma, rhabdomyosarcoma, salivary gland cancer, sarcoma, Ewing family of tumors sarcoma, Kaposi Sarcoma, soft tissue sarcoma, uterine Sézary syndrome, skin cancer (nonmelanoma), skin carcinoma, Merkel cell, small cell lung cancer, small intestine cancer, squamous cell carcinoma, squamous neck cancer with occult primary cancer, supratentorial primitive neuroectodermal tumors, T-cell lymphoma, testicular cancer, throat cancer, thymoma and thymic carcinoma, thyroid cancer, transitional cell cancer of the renal pelvis and ureter, gestational trophoblastic tumor, carcinoma of unknown primary site, urethral cancer, uterine cancer, endometrial uterine sarcoma, vaginal cancer, visual pathway and hypothalamic glioma, vulvar cancer, and Wilms tumor.

In certain embodiments, the methods of current invention can be practiced to identify subjects having a cancer involving loss or reduction in LKB1 function, and optionally, for treating cancer, wherein the cancer is non-small cell carcinoma, squamous cell carcinoma, large cell carcinoma, mucoepidermoid carcinoma, bronchioloalveolar adenocarcinoma, mixed adenosquamous carcinoma or undifferentiated carcinoma. In a specific embodiment, the methods of current invention are practiced to identify subjects having a cancer involving reduction or loss of LKB1 function and optionally, for treating a lung cancer, for example, NSCLC.

In one embodiment, a subject is identified as having a cancer not involving loss or reduction in LKB1 function. In one embodiment, a subject is identified as having a cancer not involving loss or reduction in LKB1 function if the level of LINC00473 in a test sample is not different than the level of LINC00473 in a control sample obtained from an individual belonging to the same species as the subject and not having cancer, an individual belonging to the same species as the subject and known to have a cancer not involving loss or reduction in LKB1 function or the subject prior to having a cancer.

In another embodiment, a subject is identified as having a cancer not involving loss or reduction in LKB1 function if the level of LINC00473 in a test sample is lower than the level of LINC00473 in a control sample obtained from an individual belonging to the same species as the subject and known to have a cancer involving loss or reduction in LKB1 function.

A subject can also be identified as having a cancer not involving a loss or reduction in LKB1 function based on the reference value used and the level of LINC00473 in a test sample. For example, a subject is identified as having a cancer not involving loss or reduction in LKB1 function if the level of LINC00473 in the test sample is not different than the reference value corresponding to a cancer not involving loss or reduction in LKB1 function. Alternately, a subject is identified as having a cancer not involving loss or reduction in LKB1 function if the level of LINC00473 in the test sample is lower than the reference value corresponding to a cancer involving loss or reduction in LKB1 function.

In a further embodiment of the invention, if a person is identified as having a cancer not involving a loss or reduction in LKB1 function, a cancer therapy other than the LINC00473 inhibitor is administered to the subject to treat the cancer. The additional cancer therapies discussed above in connection with cancer therapies in combination with the LINC00473 inhibitor can be administered without the LINC00473 inhibitor to a person is identified as having a cancer not involving a loss or reduction in LKB1 function. An appropriate cancer therapy to be administered to a subject can be determined by a person of ordinary skill in the art depending upon the status of cancer in the subject, for example, the subject to be treated may be evaluated, in particular, for the state of the subject's cancer, subjects overall health, age and desired aggressiveness of the therapy.

Materials and Methods

LncRNA Microarray Analysis

Total RNA was extracted from A549 cells after the transduction of wildtype LKB1, LKB1 K78I mutant, or control retroviruses for 96 hours and two biological replicates were set up. Total RNA was subjected to human lncRNA expression microarray (V3.0) analyses (ArrayStar, Rockville, Mass.). The microarray data were deposited in NCBI Gene Expression Omnibus (GEO: GSE73414). Genes with an absolute fold change of ≥2 and p-value<0.05 were considered as significantly differentially expressed.

Nanostring nCounter Gene Expression Analysis

Nanostring gene expression assay analyses were performed according to the manufacture's protocols (Nanostring Technologies, Seattle, Wash.) using customized nCounter GX CodeSet. Total RNA from cultured cells (100 ng) or RNA from FFPE tissues (150-200 ng) was hybridized with the specific capture probes and barcoded reporter probes at 65° C. for 18 hours and then loaded into the nCounter Pre-station for purifying the hybridized probes. Data collection was performed on the nCounter Digital Analyzer that counted and tabulated the individual fluorescent barcodes for target RNA molecules in each samples following the manufacturer's instructions. The raw data were analyzed with nSolver™ Analysis Software for gene expression analysis. The heatmap was generated with Heatmap.2 R package using the normalized Nanostring expression data.

RNAscope In Situ Hybridization (RNA ISH)

RNA ISH was performed on FFPE xenograft tumors and tissue microarrays (TMAs) using RNAscope® 2.0 HD Reagent Kit [BROWN 310033 or RED 310034, Advanced Cell Diagnostics (ACD), Hayward, Calif.]. Briefly, tissue sections were deparaffinized with xylene and 100% ethanol and incubated with pretreat-1 solution for 10 minutes, pretreat-2 for 15 minutes, and pretreat-3 for 30 minutes (Pretreatment kit 310020, ACD). The slides were then hybridized with a custom probe Hs-LINC00473-tv1 (targeting 781-1755 of NR_026860.1) in the HybEZ oven (ACD) at 40° C. for 2 hours. The Hs-PPIB probe for human housekeeping gene PPM was used as a control to ensure RNA quality. After hybridizations, slides were subjected to signal amplification using HD 2.0 detection Kit, and hybridization signal was detected using a mixture of solutions A and B (1:60). After counterstaining with hematoxylin, slides were dried in a 60° C. dry oven for 15 minutes and mounted with Ecomount (BioCare Medical, EM897L). The stained sections were scanned and digitized with Aperio Imagescope (Leica, Bannockburn, Ill.).

RNA-Fluorescence In Situ Hybridization (RNA-FISH)

RNA-FISH was performed using LINC00473 Stellaris® FISH probes labeled with Quasar 570 (Biosearch Technologies, Petaluma, Calif.) following the manufacturer's protocol. Imaging was performed immediately using Leica DM6000B fluorescence microscope (Bannockburn, Ill.).

Proteomic Analysis of the LINC00473-Associated Protein Complex

LncRNA was first transcribed in vitro using the MEGAscript® T7 Transcription Kit (AM1333, Life Technologies) according to the manufacturer's instructions. Identification of lncRNA interacting protein complexes was performed as previously described with modifications (55, 55). Briefly, RNAs were covalently linked to adipic acid dihydrazide agarose beads by periodate oxidation of RNA 3'-OH terminus. The beads bound with RNAs were incubated with nuclear extracts of A549 cells to pull down the lncRNA-interacting proteins. After extensive washing, beads were boiled with a loading buffer to elute the lncRNA-interacting proteins, which were further separated by SDS-PAGE and subjected to mass spectrometric analysis.

Mouse Xenograft Studies

Luciferase-expressing A549 cells or H157 cells infected with control shRNA or shLINC00473 lentiviruses were subcutaneously injected to NOD/SCID mice (Jackson Laboratory, Bar Harbor, Me.). Tumors were measured and bioluminescence imaging was performed as previously described.

Analysis of RNA Sequencing and Clinical Data

RNA sequencing data from the lung adenocarcinoma (LUAD) dataset of The Cancer Genome Atlas (TCGA) sequencing project and the accompanying clinical data were used for analysis. Normalized read counts (RSEM) for each LUAD sample aligned to LINC00473 were obtained and used for the survival curve analysis. All LUAD samples with ≥90th percentile of LINC00473 expression and those with <90th percentile were considered as high and low groups, respectively. The overall survival was analyzed by Kaplan-Meier curves and log-rank test for all LUAD patients. p-values of <0.05 were considered statistically significant.

Statistical Analyses

Data from real-time PCR, reporter assay, cell proliferation, apoptosis and in vivo xenograft experiments were analyzed using Student's t-test. Results were expressed as mean and standard deviation (±s.d.) and a p<0.05 was considered statistically significant. The biological replicates for each experiment were indicated in the figure legends.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1—A NANOSTRING ASSAY TO ASSESS LINC00473 AS A BIOMARKER FOR LKB1 STATUS

Nanostring assay is based on direct digital detection of mRNA molecules of interest using target-specific, color-coded probe pairs. Because Nanostring probes recognize small target regions (~100 bp) and no enzymes are involved, nanostring assays have been successfully used in gene expression quantification in formalin-fixed paraffin embedded (FFPE) tumor samples in which RNA is frequently degraded, in contrast with RT-PCR or microarray analysis that requires good quality RNA. Such assays are valuable because of a large collection of FFPE tumors in Biobanks is available and because these assays are rapid, reproducible and cost-effective. The first Nanostring-based Breast Cancer Assay for assessing a patient's risk of distant recurrence of disease was approved by the FDA in 2014. Moreover, FDA-approved lncRNA PCA3 assay indicates clinical potential of lncRNA. A Nanostring-based lncRNA test for assessing LINC00473 expression as a surrogate marker for the LKB1 status is provided. This assay offers several advantages:

(1) LINC00473 expression is a functional readout of the LKB1 status and will be superior to testing LKB1 gene mutation or protein level. LKB1 inactivation can result from mutations across the entire LKB1 gene, or epigenetic silencing, or post-translational inactivation, posing a challenge to detect LKB1 mutations through direct genomic sequencing and to predict their functional consequences.

(2) A significant number of LKB1-wt stromal cells within tumors can obscure detection of LKB1-null tumor cells in LKB1 Western blotting and immunohistochemistry (IHC)

studies. Since LINC00473 normally expresses at a low level but shows a significant high expression in LKB1-null cells, the measurement is not affected by the presence of stromal cells.

(3) The assay requires minimal hands-on time and runs on NanoString nCounter System, which is rapid and reproducible in clinical laboratories. It provides quantitative expression scores, likely reflecting the degree of LKB1 functional impairment. In contrast, tumor IHC requires manual scoring due to variable levels of IHC staining. Therefore, nanostring assay provides a useful test for scoring LKB1-inactivated tumors.

EXAMPLE 2—A NANOSTRING ASSAY TO IDENTIFY LKB1-INACTIVATED TUMORS BASED ON LINC00473 UPREGULATION

A nanostring-based assay for classifying LKB1-inactivacted tumors is provided. Nanostring technology allows simultaneous detection of multiple genes and a Codeset have been designed and synthesized. This Codeset includes a library of probes targeting 40 LKB1-regulated genes, including, for example, LINC00473, AGR2, SMOC1, NR4A1-3, CPS1, PPARGC1A, PDE10A, TFF1, etc., LKB1 and one or more internal control genes, for example, GAPDH, GUSB, PGK1, TUBB. The selection of the LKB1-regulated coding genes was based on a published dataset (GSE51266) that used Affymetrix human gene 1.1 ST Array (which does not include probes for LINC00473). Though their expressions seem only partially correlated with LKB1 mutational status in a panel of NSCLC cell lines, the data from the Nanostring assays can help establish a correlation of LKB1-inactivated lung cancer cells with one or more LKB1-regulated genes. Each target gene can be detected using a pair of reporter and capture probes carrying 50-base target-specific sequences and each barcode specifically represents a single target molecule. The assay involves the steps of: hybridization, purification, immobilization, and digital data acquisition by Nanostring nCounter. 100 ng of RNA per sample can be tested initially. Gene expression is measured by counting the number of times the color-coded barcode for that gene is detected, and the barcode counts are then tabulated and analyzed.

Initial validation using human lung tumor specimens is performed. Based on a power analysis of the pilot experiment, a sample size of 9 matched tumor/normal pairs can have 95% power to reach the similar observed difference as that of the pilot study. Therefore, 10 LKB1-wt and 10 LKB1-null human lung adenocarcinoma samples and their matching tumor-adjacent normal tissues (both frozen and FFPE samples) can be analyzed. An initial cutoff score and assay sensitivity and specificity can be determined using the described approaches.

LKB1-null cell lines express highly increased, yet variable LINC00473 expression levels that might be due to co-existing mutations or other mechanisms and hence, the cutoff score are carefully evaluated. The data can provide the predictive value of LINC00473 as a surrogate marker for LKB1 inactivation, as well as guiding subsequent validation studies. A large cohort of human lung tumors can be used to perform validation of LKB1 mutational status based on LINC473 expression.

EXAMPLE 3—GENOME-WIDE LNCRNA PROFILING IDENTIFIED LINC00473 AS A TOP LKB1 SIGNALING-REGULATED LNCRNA IN NSCLC CELLS

Figure 5A:
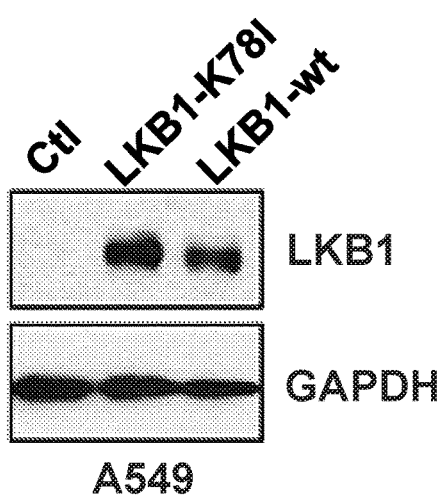
FIGS. 5A-5I. LINC00473 is induced by LKB1 loss in NSCLC cells. (A) Western blotting analysis of expression of LKB1 wild-type (wt) or kinase-dead K78I mutant in transduced LKB1-null lung adenocarcinoma A549 cells. A549 cells infected with pBabe vector retroviruses were used as controls (Ctl). (B, C) Volcano plots show differentially expressed lncRNAs after expression of LKB1 wt (B) or LKB1 K78I mutant (C) in A549 cells by LncRNA microarray (V3.0) analysis. The cutoff criteria were fold-change of ≥2 and $p<0.05$. (D) A volcano plot shows differentially expressed lncRNAs in two LKB1-null cell lines (A549 and H460) compared with two LKB1-wt cell lines (H322 and H3123). (E) A heatmap shows expression levels of several LKB1-regulated protein-coding and non-coding genes measured in Nanostring assays. (F, G) Two LINC00473 transcript variants (tv1: NR_026860 and tv2: NR_026861) show significantly elevated expression in LKB1-mutant groups as compared to LKB1-wt groups based on the Nanostring assays. (H) CCLE data analysis identified NSCLC cell lines (n=130) with outlier LINC00473 expression levels. (I) Enhanced LINC00473 expression was significantly associated with LKB1 mutations in CCLE NSCLC cell lines. See also Tables 1-3.
Figure 5B:
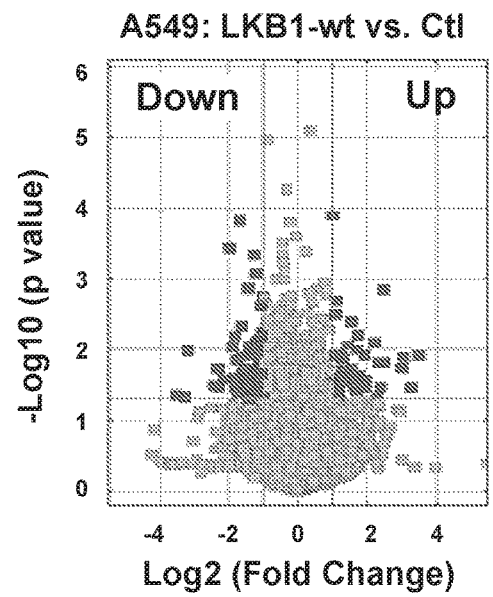

LncRNA involvement in altered LKB1 signaling in lung cancer is currently unknown. To investigate whether lncRNAs contribute to loss of LKB1 tumor suppression in lung tumorigenesis and maintenance, genome-wide lncRNA transcriptional profiling was performed to identify lncRNAs associated with aberrant LKB1 signaling. Three groups of cells were generated by transducing LKB1-null A549 NSCLC cells with retroviruses harboring wild-type (wt) LKB1, LKB1 kinase-dead mutant (K78I), or vector control (Ctl). Western blotting analysis confirmed the expression and kinase activity of LKB1-wt and -K78I proteins in an AMPK activation assay under glucose-free culture conditions (FIG. 5A). Arraystar Human LncRNA Expression Microarrays were used to profile changes in the expression of ~30,000 lncRNAs in three experimental conditions. Using an absolute fold change≥2.0 and a p-value<0.05, 164 differentially expressed lncRNAs were identified (64 up-regulated and 100 down-regulated) in A549 cells upon LKB1-wt expression compared to control (FIG. 5B, Table 1).

TABLE 1

Differentially expressed lncRNAs in LKB1-null A549 cells after expression of wild-type LKB1 in comparison with vector control.

| Probe Name | Seq. name | Gene Symbol | Fold Change (LKB1/Ctl) | p value LKB1 vs Ctl |
|---|---|---|---|---|
| ASHGA5P033002 | ENST00000584258 | RP11-338L22.2 | −17.89 | 0.00475 |
| ASHGA5P026349 | ENST00000528480 | RP11-702F3.1 | −11.67 | 0.00164 |
| ASHGA5P032197 | ENST00000582225 | RP11-726O12.3 | −9.83 | 0.01415 |
| ASHGA5P003696 | NR_036641 | PDGFC | −9.37 | 0.00366 |
| ASHGA5P029200 | ENST00000556301 | CTD-2325P2.4 | −8.36 | 0.01070 |
| ASHGA5P045844 | NR_033937 | LOC100132077 | −7.59 | 0.00764 |
| ASHGA5P028099 | ENST00000550290 | RP11-631N16.2 | −7.25 | 0.02418 |
| ASHGA5P048509 | BG953017 |  | −5.90 | 0.01294 |
| ASHGA5P035735 | uc002rcs.1 | AX748233 | −5.42 | 0.00212 |
| ASHGA5P036250 | uc001bsm.3 | PRO0611 | −5.17 | 0.02095 |
| ASHGA5P026274 | NR_033313 | BDNF-AS | −5.05 | 0.00409 |
| ASHGA5P037302 | uc002ywn.1 | AL109792 | −5.01 | 0.00021 |
| ASHGA5P052263 | ENST00000512882 | CTD-2170G1.2 | −4.65 | 0.02812 |
| ASHGA5P046913 | ENST00000417210 | RP11-444I9.4 | −4.61 | 0.00143 |
| ASHGA5P046410 | TCONS_00001387 | XLOC_000701 | −4.15 | 0.00590 |
| ASHGA5P030630 | ENST00000558429 | RP11-138H8.2 | −4.02 | 0.01611 |
| ASHGA5P047713 | TCONS_00014218 | XLOC_006259 | −4.01 | 0.00673 |
| ASHGA5P021304 | ENST00000529804 | RP11-820L6.1 | −3.91 | 0.04321 |
| ASHGA5P052912 | ENST00000584911 | LINC00473 | −3.77 | 0.00033 |

TABLE 1-continued

Differentially expressed lncRNAs in LKB1-null A549 cells after expression of wild-type LKB1 in comparison with vector control.

| Probe Name | Seq. name | Gene Symbol | Fold Change (LKB1/Ctl) | p value LKB1 vs Ctl |
|---|---|---|---|---|
| ASHGA5P058795 | uc.431+ | uc.431 | −3.69 | 0.00841 |
| ASHGA5P034600 | AY665172R |  | −3.69 | 0.00806 |
| ASHGA5P014758 | ENST00000413066 | RP11-29B9.1 | −3.68 | 0.00415 |
| ASHGA5P057014 | TCONS_00011960 | XLOC_005473 | −3.66 | 0.01210 |
| ASHGA5P031386 | ENST00000561567 | RP4-536B24.3 | −3.66 | 0.03473 |
| ASHGA5P032753 | ENST00000425277 | AC099684.1 | −3.55 | 0.03629 |
| ASHGA5P052156 | uc001fcp.3 | DKFZp564E1082 | −3.49 | 0.00788 |
| ASHGA5P035942 | uc002sla.3 | DQ588163 | −3.46 | 0.01331 |
| ASHGA5P032632 | ENST00000446002 | RP11-412H9.2 | −3.37 | 0.00164 |
| ASHGA5P040453 | ENST00000504240 | RP11-479O16.1 | −3.26 | 0.04384 |
| ASHGA5P027538 | ENST00000552065 | RP11-642P15.1 | −3.25 | 0.00415 |
| ASHGA5P042172 | NR_026860 | LINC00473 | −3.24 | 0.00034 |
| ASHGA5P040812 | uc021ygc.1 | LOC729421 | −3.16 | 0.03323 |
| ASHGA5P032475 | ENST00000458392 | FAM215B | −3.16 | 0.00767 |
| ASHGA5P034845 | ENST00000453806 | TRAPPC12-AS1 | −3.15 | 0.00441 |
| ASHGA5P048909 | ENST00000568297 | RP11-386M24.6 | −3.12 | 0.00997 |
| ASHGA5P038205 | NR_033947 | LIMD1-AS1 | −3.12 | 0.03420 |
| ASHGA5P043207 | TCONS_00018388 | XLOC_008668 | −3.11 | 0.02634 |
| ASHGA5P045599 | TCONS_00002581 | XLOC_001195 | −3.09 | 0.02916 |
| ASHGA5P032042 | ENST00000568947 | AC137934.1 | −3.05 | 0.04090 |
| ASHGA5P047720 | ENST00000433085 | RP11-383C6.2 | −3.04 | 0.03970 |
| ASHGA5P021076 | ENST00000524512 | RP11-60I3.4 | −3.03 | 0.03021 |
| ASHGA5P042171 | NR_026861 | LINC00473 | −2.93 | 0.02140 |
| ASHGA5P049614 | ENST00000582184 | RP11-640N20.1 | −2.93 | 0.04547 |
| ASHGA5P027993 | uc001dzn.1 | BC069739 | −2.84 | 0.00828 |
| ASHGA5P036158 | uc002tte.3 | BX648270 | −2.81 | 0.04173 |
| ASHGA5P032729 | ENST00000575085 | RP13-638C3.3 | −2.79 | 0.02690 |
| ASHGA5P053420 | ENST00000443799 | GAS5 | −2.77 | 0.04272 |
| ASHGA5P057723 | TCONS_00021137 | XLOC_009763 | −2.76 | 0.01660 |
| ASHGA5P034881 | ENST00000340444 | AC010969.1 | −2.67 | 0.02171 |
| ASHGA5P032021 | ENST00000565150 | RP11-566K11.5 | −2.66 | 0.01226 |
| ASHGA5P041101 | ENST00000576302 | CTD-2031P19.5 | −2.65 | 0.00780 |
| ASHGA5P029364 | uc001ynv.1 | AX746968 | −2.61 | 0.04128 |
| ASHGA5P022710 | ENST00000561275 | OIP5-AS1 | −2.61 | 0.01084 |
| ASHGA5P036254 | ENST00000444196 | AC010894.3 | −2.60 | 0.03453 |
| ASHGA5P049639 | ENST00000581922 | AC124789.1 | −2.60 | 0.03681 |
| ASHGA5P049296 | ENST00000566217 | RP11-296I10.6 | −2.58 | 0.00650 |
| ASHGA5P036712 | ENST00000453921 | RP4-564O4.1 | −2.55 | 0.02081 |
| ASHGA5P027910 | ENST00000537346 | DENND5B-AS1 | −2.51 | 0.04699 |
| ASHGA5P016018 | uc001eho.1 | BC063600 | −2.51 | 0.01200 |
| ASHGA5P023498 | ENST00000582261 | AC015818.3 | −2.51 | 0.04689 |
| ASHGA5P028123 | ENST00000421943 | RP11-426L16.3 | −2.48 | 0.03215 |
| ASHGA5P020949 | ENST00000522416 | KB-1639H6.2 | −2.45 | 0.02119 |
| ASHGA5P014957 | ENST00000415154 | LINC00226 | −2.44 | 0.03633 |
| ASHGA5P047777 | ENST00000440388 | RP11-500G10.5 | −2.44 | 0.02796 |
| ASHGA5P033095 | ENST00000577557 | RP5-1028K7.2 | −2.43 | 0.03239 |
| ASHGA5P047324 | ENST00000438202 | RP11-534G20.3 | −2.41 | 0.01113 |
| ASHGA5P040455 | uc003jsd.1 | BX641110 | −2.40 | 0.00593 |
| ASHGA5P031595 | ENST00000444326 | CRYM-AS1 | −2.40 | 0.03788 |
| ASHGA5P030942 | ENST00000565648 | RP11-473I1.5 | −2.39 | 0.03802 |
| ASHGA5P030140 | ENST00000560337 | RP11-272D12.2 | −2.39 | 0.00377 |
| ASHGA5P031271 | uc002ezq.3 | BC033164 | −2.36 | 0.01131 |
| ASHGA5P028900 | NR_027350 | MIR17HG | −2.35 | 0.02070 |
| ASHGA5P031092 | ENST00000563777 | FBXL19-AS1 | −2.35 | 0.03054 |
| ASHGA5P043735 | ENST00000452986 | AC004878.2 | −2.33 | 0.01133 |
| ASHGA5P033372 | NR_028439 | C17orf109 | −2.31 | 0.00300 |
| ASHGA5P050764 | ENST00000457387 | RP4-717I23.3 | −2.30 | 0.03935 |
| ASHGA5P051192 | ENST00000540720 | DGCR5 | −2.26 | 0.01158 |
| ASHGA5P026001 | uc010ady.1 | THSD1P1 | −2.25 | 0.01503 |
| ASHGA5P047405 | TCONS_00014981 | XLOC_007062 | −2.23 | 0.00342 |
| ASHGA5P054980 | ENST00000430109 | RP4-758J18.10 | −2.22 | 0.03927 |
| ASHGA5P015132 | NR_045768 | ATF2 | −2.19 | 0.00759 |
| ASHGA5P037609 | ENST00000417194 | GUSBP11 | −2.18 | 0.04156 |
| ASHGA5P027688 | ENST00000541797 | RP11-749H20.1 | −2.18 | 0.00278 |
| ASHGA5P030904 | ENST00000576943 | RP11-473M20.15 | −2.17 | 0.03074 |
| ASHGA5P055197 | ENST00000532315 | RP11-166D19.1 | −2.17 | 0.04056 |
| ASHGA5P019723 | ENST00000501954 | RP11-847H18.2 | −2.17 | 0.02701 |
| ASHGA5P043181 | ENST00000471553 | RP5-1121E10.2 | −2.17 | 0.02604 |
| ASHGA5P043280 | ENST00000451832 | IMMP2L-IT1 | −2.15 | 0.01517 |
| ASHGA5P023124 | ENST00000570454 | RP11-669E14.6 | −2.14 | 0.01135 |
| ASHGA5P027657 | ENST00000542427 | RP11-282O18.3 | −2.13 | 0.02031 |
| ASHGA5P051337 | uc003azm.3 | BC040700 | −2.12 | 0.02353 |
| ASHGA5P057321 | TCONS_00016063 | XLOC_007452 | −2.11 | 0.01685 |

TABLE 1-continued

Differentially expressed lncRNAs in LKB1-null A549 cells after expression of wild-type LKB1 in comparison with vector control.

| Probe Name | Seq. name | Gene Symbol | Fold Change (LKB1/Ctl) | p value LKB1 vs Ctl |
|---|---|---|---|---|
| ASHGA5P019895 | ENST00000504833 | CTD-2001C12.1 | −2.11 | 0.01846 |
| ASHGA5P042232 | uc003mwn.1 | AK094934 | −2.10 | 0.03267 |
| ASHGA5P041222 | ENST00000504769 | TMEM161B-AS1 | −2.09 | 0.01682 |
| ASHGA5P043145 | uc003ucm.3 | PMS2L14 | −2.07 | 0.03668 |
| ASHGA5P056937 | TCONS_00010747 | XLOC_004478 | −2.07 | 0.02858 |
| ASHGA5P042300 | NR_026790 | HCG11 | −2.05 | 0.01810 |
| ASHGA5P030798 | ENST00000559400 | CTD-3076O17.2 | −2.01 | 0.02744 |
| ASHGA5P039775 | AA151944 | | −2.01 | 0.04605 |
| ASHGA5P049116 | uc002dkc.2 | AF086126 | −2.00 | 0.01360 |
| ASHGA5P052552 | ENST00000505870 | RP1-80B9.2 | −2.00 | 0.02029 |
| ASHGA5P028659 | TCONS_00009877 | XLOC_004299 | 2.00 | 0.03789 |
| ASHGA5P041590 | ENST00000519491 | RP11-281O15.4 | 2.06 | 0.04277 |
| ASHGA5P056387 | TCONS_00003845 | XLOC_001650 | 2.09 | 0.03754 |
| ASHGA5P019979 | NR_038989 | LOC100507584 | 2.10 | 0.04541 |
| ASHGA5P023807 | HMlincRNA507- | HMlincRNA507 | 2.12 | 0.03666 |
| ASHGA5P018130 | ENST00000449772 | AC068535.3 | 2.15 | 0.00524 |
| ASHGA5P027701 | ENST00000539532 | RP11-117L5.4 | 2.16 | 0.03470 |
| ASHGA5P054017 | uc010pqo.1 | LINC00303 | 2.31 | 0.01077 |
| ASHGA5P034879 | ENST00000474667 | RP11-521D12.5 | 2.32 | 0.03665 |
| ASHGA5P047002 | uc001kjn.4 | BC035380 | 2.33 | 0.02899 |
| ASHGA5P026246 | ENST00000528204 | NAV2-IT1 | 2.34 | 0.01867 |
| ASHGA5P032309 | ENST00000582320 | MIR451B | 2.39 | 0.04210 |
| ASHGA5P026754 | ENST00000434606 | RP13-221M14.3 | 2.40 | 0.03211 |
| ASHGA5P022400 | ENST00000556120 | DIO3OS | 2.40 | 0.04745 |
| ASHGA5P019377 | NR_023345 | CNKSR1 | 2.42 | 0.03385 |
| ASHGA5P030322 | uc021sxp.1 | AK093600 | 2.45 | 0.04415 |
| ASHGA5P034153 | ENST00000561778 | CTC-523E23.1 | 2.46 | 0.03038 |
| ASHGA5P019066 | ENST00000466730 | ABCA17P | 2.47 | 0.02535 |
| ASHGA5P058606 | uc010vzg.1 | AK295707 | 2.54 | 0.02267 |
| ASHGA5P033292 | ENST00000412483 | RP4-799P18.2 | 2.60 | 0.03655 |
| ASHGA5P019188 | ENST00000472193 | PLCL1 | 2.65 | 0.02660 |
| ASHGA5P032925 | ENST00000577087 | RP11-311F12.1 | 2.73 | 0.02057 |
| ASHGA5P025683 | NR_026782 | HEATR8 | 2.77 | 0.04836 |
| ASHGA5P045689 | ENST00000439960 | RP11-296L22.8 | 2.86 | 0.03930 |
| ASHGA5P027787 | TCONS_00010156 | XLOC_004622 | 2.90 | 0.02240 |
| ASHGA5P025958 | NR_047601 | UTY | 2.91 | 0.03915 |
| ASHGA5P000386 | chr3: 120042175-120054600+ | chr3: 120042175-120054600 | 2.92 | 0.04485 |
| ASHGA5P050152 | TCONS_00019041 | XLOC_008978 | 3.00 | 0.04731 |
| ASHGA5P041516 | ENST00000519327 | CTC-340A15.2 | 3.00 | 0.04236 |
| ASHGA5P040581 | TCONS_00021912 | XLOC_010505 | 3.13 | 0.03295 |
| ASHGA5P031889 | ENST00000567721 | CTD-2520I13.1 | 3.15 | 0.03209 |
| ASHGA5P035710 | ENST00000566840 | RP11-254F7.1 | 3.18 | 0.03356 |
| ASHGA5P029582 | TCONS_00008273 | XLOC_003714 | 3.23 | 0.03527 |
| ASHGA5P053840 | ENST00000536815 | RP11-395P17.3 | 3.24 | 0.00405 |
| ASHGA5P043886 | ENST00000418215 | AC000123.4 | 3.25 | 0.03529 |
| ASHGA5P058314 | TCONS_00029913 | XLOC_014386 | 3.30 | 0.03561 |
| ASHGA5P037514 | ENST00000400362 | BX322557.10 | 3.31 | 0.01866 |
| ASHGA5P000480 | chr6: 63131625-63144250+ | chr6: 63131625-63144250 | 3.37 | 0.00885 |
| ASHGA5P027762 | ENST00000537192 | RP11-1038A11.3 | 3.43 | 0.03621 |
| ASHGA5P057099 | TCONS_00013289 | XLOC_005957 | 3.78 | 0.02449 |
| ASHGA5P000112 | BF986711 | | 3.79 | 0.04501 |
| ASHGA5P054466 | ENST00000448017 | RP11-556E13.1 | 3.81 | 0.00705 |
| ASHGA5P038359 | ENST00000486726 | RP11-231E6.1 | 3.82 | 0.01401 |
| ASHGA5P026072 | BF869766 | | 3.85 | 0.03082 |
| ASHGA5P041947 | ENST00000434493 | RP1-177I10.1 | 3.91 | 0.02967 |
| ASHGA5P031972 | ENST00000567093 | CTD-2542L18.1 | 3.99 | 0.03710 |
| ASHGA5P054842 | ENST00000530412 | TRIM51HP | 4.08 | 0.04952 |
| ASHGA5P056805 | TCONS_00008798 | XLOC_003555 | 4.12 | 0.00758 |
| ASHGA5P022501 | ENST00000558097 | RP11-798K3.2 | 4.25 | 0.02854 |
| ASHGA5P050918 | NR_040710 | LOC100131208 | 4.64 | 0.00356 |
| ASHGA5P030689 | TCONS_00006338 | XLOC_002953 | 4.71 | 0.04584 |
| ASHGA5P000374 | chr2: 90959050-90986900+ | chr2: 90959050-90986900 | 4.93 | 0.01312 |
| ASHGA5P041498 | ENST00000522975 | CTC-436K13.1 | 4.93 | 0.00571 |
| ASHGA5P058850 | uc.468+ | uc.468 | 5.01 | 0.03627 |
| ASHGA5P031046 | ENST00000564381 | RP11-673P17.4 | 5.06 | 0.02052 |
| ASHGA5P044241 | ENST00000527318 | RP11-412B14.1 | 5.19 | 0.04234 |
| ASHGA5P042137 | ENST00000415477 | RP1-292B18.4 | 5.20 | 0.04016 |
| ASHGA5P054514 | NR_038986 | GRID1-AS1 | 5.24 | 0.00955 |
| ASHGA5P050022 | ENST00000563752 | SLC25A3P1 | 5.55 | 0.01846 |
| ASHGA5P023783 | HMlincRNA407- | HMlincRNA407 | 5.68 | 0.01251 |
| ASHGA5P029035 | AF083119R | | 8.05 | 0.00593 |
| ASHGA5P029153 | ENST00000554160 | RP11-108M12.3 | 8.35 | 0.00206 |

TABLE 1-continued

Differentially expressed lncRNAs in LKB1-null A549 cells after expression of wild-type LKB1 in comparison with vector control.

| Probe Name | Seq. name | Gene Symbol | Fold Change (LKB1/Ctl) | p value LKB1 vs Ctl |
|---|---|---|---|---|
| ASHGA5P019501 | uc011kur.2 | LOC401431 | 9.70 | 0.00594 |
| ASHGA5P042997 | AA810436 | | 11.31 | 0.01310 |

Figure 5C:
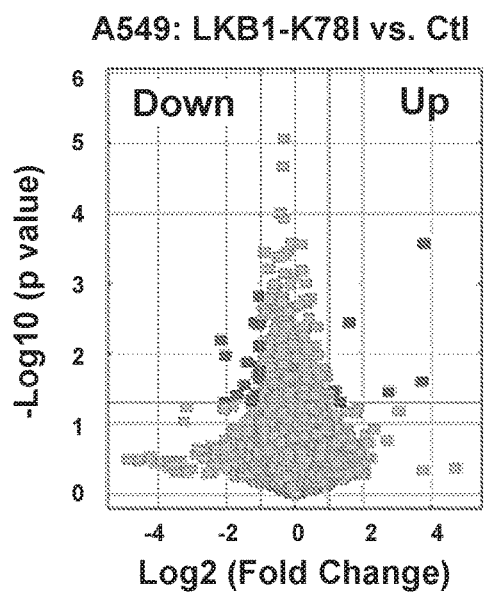
Figure 5D:
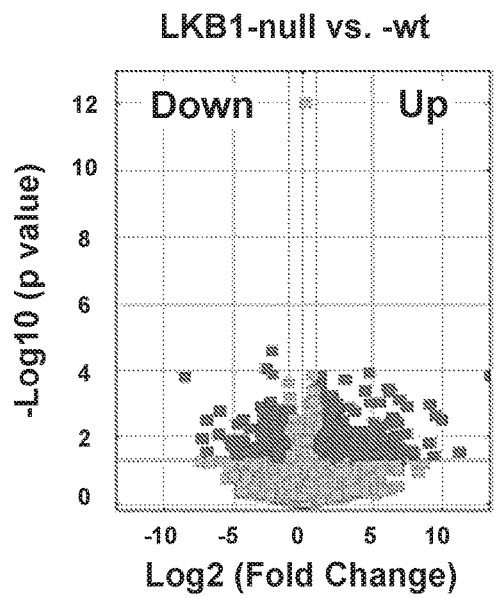

17 up-regulated and 49 down-regulated lncRNAs associated with LKB1-K78I mutant expression compared to control were also observed (FIG. 5C). Comparing expression profiles of LKB1-wt- and K78I-expressing cells, 33 up-regulated and 83 down-regulated lncRNAs were identified, suggesting that their expression is dependent on LKB1 kinase activity. Furthermore, lncRNA expression patterns were profiled and compared between 2 groups of cell lines: LKB1-null (A549, H460) and LKB1-wt (H322, H3123), and 1449 up-regulated and 918 down-regulated lncRNAs were observed in LKB1-null cell lines (FIG. 5D). Finally, by integrating LKB1-regulated lncRNAs and lncRNAs differentially expressed in LKB1-null cell lines (Table 1), a list of LKB1-regulated lncRNAs were identified (10 up-regulated and 1 down-regulated) that are differentially expressed between LKB1-null and -wt lung cancer cells (Table 2).

LKB1-null (A549 and H460) and 2 LKB1-expressing cells (H322 and H3123), while LINC00473 tv2 showed about a 40-fold change.

EXAMPLE 4—ELEVATED LINC00473 EXPRESSION TIGHTLY CORRELATES WITH NSCLC LKB1 INACTIVATION STATUS

To validate LKB1-regulated lncRNAs, a Nanostring-based assay was used that allows direct digital detection of multiple RNA molecules of interest using target-specific, color-coded probe pairs. This platform enables to simultaneously evaluate multiple LKB1-regulated mRNA and lncRNA candidates (especially LINC00473). Hybridizations were performed on RNA samples from a pair of control and LKB1-expressing A549 cells and a panel of NSCLC cell

TABLE 2

A list of lncRNAs showing reduced expression upon LKB1 over-expression in LKB1-null A549 and having significant enhanced expression in 2 LKB1-null NSCLC cell lines (A549 and H460) compared to 2 LKB1-expressing NSCLC cell lines (H322 and H3123).

| Probe Name | Seq. name | Gene Symbol | Fold Change (Mut/Wt) | p value Mut vs Wt | Fold Change (OE/Ctl) | p value OE vs Ctl |
|---|---|---|---|---|---|---|
| ASHGA5P042172 | NR_026860 | LINC00473 | 11299.72 | 0 | −3.24 | 0.000341 |
| ASHGA5P052912 | ENST00000584911 | LINC00473 | 549.47 | 0 | −3.77 | 0.000332 |
| ASHGA5P043735 | ENST00000452986 | AC004878.2 | 111.53 | 0 | −2.33 | 0.011334 |
| ASHGA5P037302 | uc002ywn.1 | AL109792 | 70.10 | 0 | −5.01 | 0.000208 |
| ASHGA5P040455 | uc003jsd.1 | BX641110 | 55.49 | 0 | −2.40 | 0.005932 |
| ASHGA5P042171 | NR_026861 | LINC00473 | 39.08 | 1.60E−05 | −2.93 | 0.021401 |
| ASHGA5P040453 | ENST00000504240 | RP11-479O16.1 | 38.60 | 0.000106 | −3.26 | 0.043839 |
| ASHGA5P034600 | AY665172R | | 19.68 | 5.80E−05 | −3.69 | 0.008063 |
| ASHGA5P026274 | NR_033313 | BDNF-AS | 3.07 | 0.023699 | −5.05 | 0.004087 |
| ASHGA5P047405 | TCONS_00014981 | XLOC_007062 | 2.54 | 0.001468 | −2.23 | 0.003416 |
| ASHGA5P042232 | uc003mwn.1 | AK094934 | 2.51 | 0.012908 | −2.10 | 0.032668 |
| ASHGA5P056937 | TCONS_00010747 | XLOC_004478 | 2.01 | 0.033793 | −2.07 | 0.028576 |
| ASHGA5P029153 | ENST00000554160 | RP11-108M12.3 | −5.21 | 0.007876 | 8.35 | 0.002058 |

Figure 5E:
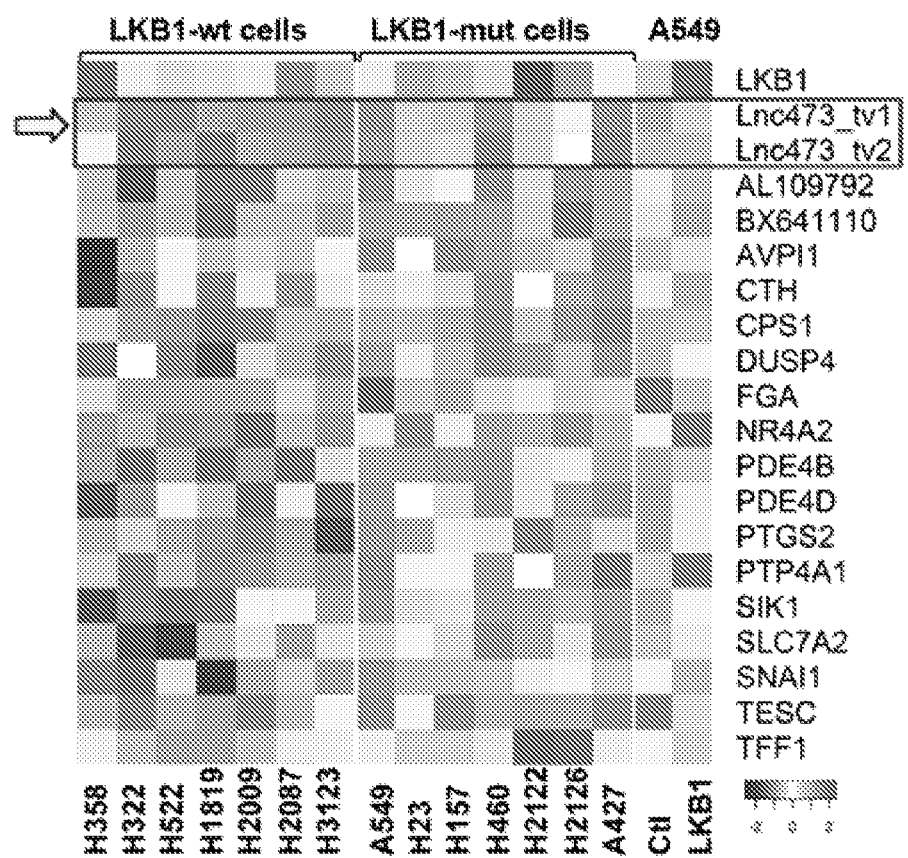

Notably, this list contained 3 transcripts for LINC00473 gene (aka. C6orf176, abbreviated as Lnc473 in the figures), which encodes an intergenic lncRNA from the chromosome 6q27 locus. LINC00473 consists of two exons and has two annotated Refseq transcript isoforms sharing exon 1: transcript variant 1 (tv1; NR_026860, 1822 nt) and tv2 (NR_026861, 1123 nt). 5' and 3' RACE assays identified 3 LINC00473 transcript variants, tv1.1, tv2.1 and tv2.2, but not two annotated transcripts. LINC00473-tv1.1 had a shorter 5' end from the annotated tv1, while tv2.1 and tv2.2 had different 5' and 3' ends from the annotated tv2. Coding potential analysis strongly suggested that LINC00473 is a noncoding RNA. Both tv1 and tv2 transcript variants showed significant activation in LKB1-null NSCLC cells (Table 2). LINC00473 tv1 was the top differentially expressed lncRNA (>10,000-fold change) comparing the 2 lines (7 LKB1-wt and 7 LKB1-mut) using a customized codeset. The codeset included several LKB1-regulated lncRNA candidates, known LKB1-regulated protein-coding genes, as well as three housekeeping genes (GAPDH, GUSB and TUBB). As shown in the heatmap (FIG. 5E, right panel), LKB1 expression in LKB1-null A549 cells caused significant down-regulation of known protein-coding genes (AVPI1, CTH, CPS1, DUSP4, FGA, NR4A2, PDE4B, PDE4D, PTGS2, PTP4A1, SIK1, SLC7A2, SNAI1, TESC and TFF1), as well as three lncRNAs (LINC00473, AL109792, and BX64110). However, when examined across various cell lines with the confirmed status of cellular LKB1 protein expression, LINC00473 expression showed the best correlation with LKB1-inactivated status (FIG. 5E, left and middle panels). Other LKB1-regulated genes, including LncRNAs AL109792 and BX64110, were only partially correlated with the LKB1 status, suggesting cell context-dependent gene regulation.

Figure 5F:
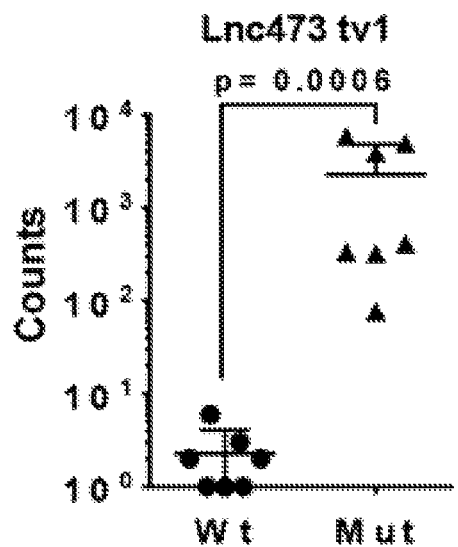
Figure 5G:
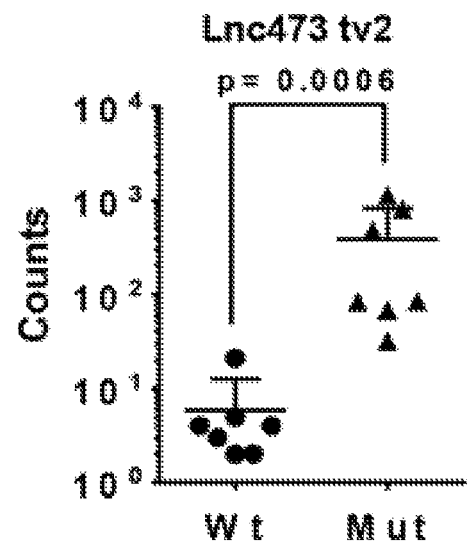
Figure 5H:
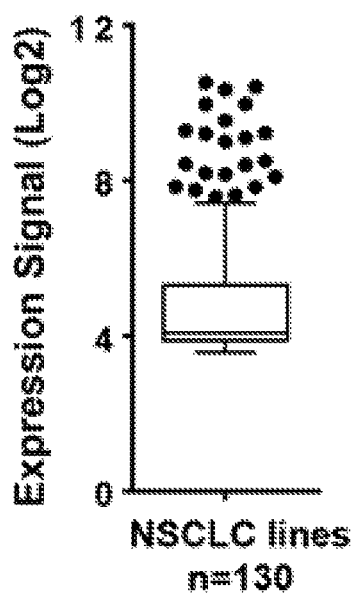
Figure 5I:
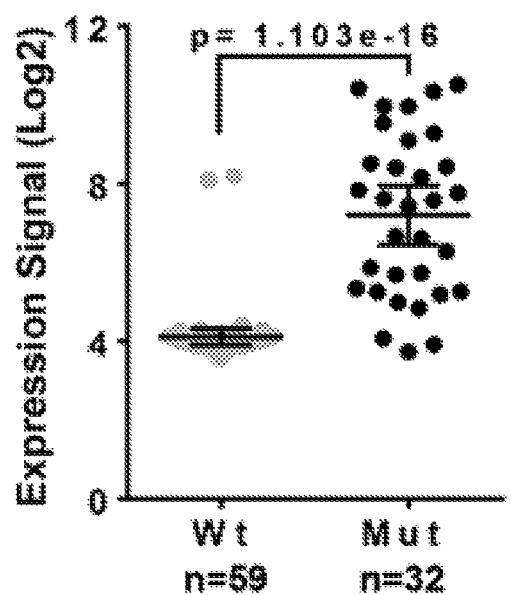

Both LINC00473 tv1 and tv2 isoforms showed low or absent expression in 7 LKB1-wt NSCLC cell lines but significantly enhanced expression in 7 LKB1-mut cell lines (FIG. 5F, G). LINC00473 differential expression in LKB1-wt and LKB1-mut cell lines was further corroborated by qRT-PCR data. Enhanced expression of a known LKB1 target gene SIK1 was also confirmed, but was not consistent across all cell lines tested. Moreover, SIK1 has relatively high basal expression. Additionally, LINC00473 expression was surveyed in 130 NSCLC cell lines using Affymetrix microarray data from the Cancer Cell Line Encyclopedia (CCLE) and these arrays only contained the probes for LINC00473 tv1. A subset of NSCLC cell lines showed an outlier LINC00473 tv1 expression (FIG. 5H, and Table 3). Analysis of cell lines with annotated LKB1 mutation status revealed that LINC00473 expression was significantly enhanced in LKB1-mutant NSCLC cell lines (n=32) in comparison to LKB1-wt lines (n=59) (Table 3, FIG. 5I) and the enhancement was more significant as compared to SIK1 expression. Furthermore, two LKB1-wt cell lines with high LINC00473 expression, H292 and DV90, were predicted to have LKB1 loss based on a 16-gene signature score. H292 is a lung mucoepidermoid carcinoma cell line that contains a t(11;19) translocation that leads to the generation of the CRTC1-MAML2 fusion and subsequent constitutive activation of CREB-mediated transcription, thus mimicking LKB1 loss. Collectively, these data strongly support that LINC00473 is consistently the most elevated gene in LKB1-inactivated NSCLC cell lines regardless of other co-existing gene mutations.

TABLE 3

Lnc473 expression in human NSCLC cell lines from CCLE database and their associated LKB1 mutation status. All samples had primary site of lung and histology of carcinoma.

| Cell line primary name | RMA (Log2) | Gender | Hist Subtype1 | LKB1 status | LKB1 mutation (#) | Predicted by a 16-gene score (##) |
|---|---|---|---|---|---|---|
| NCI-H1944 | 10.5141 | F | non_small_cell_carcinoma | mutant | LKB1 loss, NOS | LKB1 loss |
| ChaGo-K-1 | 10.41772 | M | NS | mutant | p.G56V | LKB1 loss |
| HCC-15 | 10.34715 | M | squamous_cell_carcinoma | mutant | Large deletion, NOS | LKB1 loss |
| LU65 | 9.971215 | M | non_small_cell_carcinoma | mutant | p.G196_L201 deletion | LKB1 loss |
| NCI-H1563 | 9.964172 | M | adenocarcinoma | mutant | p.Y272* | LKB1 loss |
| NCI-H1437 | 9.547726 | M | adenocarcinoma | mutant | E98-G155 del. | LKB1 loss |
| NCI-H460 | 9.288111 | M | large_cell_carcinoma | mutant | p.Q37* | LKB1 loss |
| NCI-H2172 | 9.228016 | F | non_small_cell_carcinoma | Unknown | | LKB1 loss |
| NCI-H2023 | 9.205874 | M | adenocarcinoma | Unknown | | LKB1 loss |
| RERF-LC-MS | 9.093593 | | non_small_cell_carcinoma | mutant | Large deletion, NOS | LKB1 loss |
| NCI-H1915 | 9.004812 | F | large_cell_carcinoma | Unknown | | LKB1 loss |
| NCI-H1623 | 8.511945 | M | adenocarcinoma | mutant | p.L285Q | LKB1 loss |
| NCI-H838 | 8.424098 | M | non_small_cell_carcinoma | mutant | p.T212fs | LKB1 loss |
| NCI-H2122 | 8.404129 | F | adenocarcinoma | mutant | p.P281fs*6 | LKB1 loss |
| DV-90 | 8.195443 | M | adenocarcinoma | wt | WT | LKB1 loss |
| NCI-H1395 | 8.166507 | F | adenocarcinoma | mutant | p.E57fs | LKB1 loss |
| NCI-H292 | 8.095381 | F | mucoepidermoid_carcinoma | wt | | LKB1 loss |
| NCI-H2110 | 7.841765 | | non_small_cell_carcinoma | Unknown | | LKB1 loss |
| NCI-H1355 | 7.839176 | M | adenocarcinoma | mutant | p.K48fs | LKB1 loss |
| A549 | 7.755318 | M | non_small_cell_carcinoma | mutant | p.Q37* | LKB1 loss |
| NCI-H1755 | 7.620098 | F | adenocarcinoma | mutant | p.P281fs*6 | LKB1 loss |
| NCI-H1568 | 7.58 | F | non_small_cell_carcinoma | mutant | LKB1 loss, NOS | LKB1 loss |
| MOR/CPR | 7.421945 | | adenocarcinoma | mutant | | LKB1 loss |
| COR-L105 | 7.362305 | M | adenocarcinoma | Unknown | | LKB1 loss |
| NCI-H23 | 6.667511 | M | non_small_cell_carcinoma | mutant | p.W332* | LKB1 loss |
| NCI-H1666 | 6.613 | F | bronchioloalveolar_adenocarcinoma | mutant | p.V236fs*30 | LKB1 loss |
| NCI-H2126 | 6.287378 | M | adenocarcinoma | mutant | c.465_862del 398 | LKB1 loss |
| NCI-H1385 | 5.867911 | F | squamous_cell_carcinoma | mutant | LKB1 loss, NOS | LKB1 loss |
| DFCI024 | 5.738737 | | adenocarcinoma | Mutant | | |
| HCC-44 | 5.686449 | F | adenocarcinoma | mutant | p.M51I; p.52fs | LKB1 loss |
| LUDLU-1 | 5.432516 | M | squamous_cell_carcinoma | Unknown | | LKB1 loss |
| NCI-H647 | 5.342878 | M | mixed_adenosquamous_carcinoma | mutant | LKB1 loss, NOS | LKB1 loss |
| NCI-H1651 | 5.267038 | M | adenocarcinoma | mutant | p.? | LKB1 loss |
| VMRC-LCD | 5.254231 | M | adenocarcinoma | mutant | p.G155_splice | LKB1 loss |
| NCI-H810 | 5.184853 | M | large_cell_carcinoma | mutant | p.P179S | LKB1 wt |
| NCI-H1734 | 4.985246 | F | adenocarcinoma | mutant | p.M51fs*14; p.E357K; p.M392I | LKB1 loss |
| T3M-10 | 4.954805 | M | large_cell_carcinoma | Unknown | | |
| NCI-H2030 | 4.837931 | M | non_small_cell_carcinoma | mutant | p.E317* | LKB1 loss |
| Hs 229.T | 4.561258 | M | adenocarcinoma | Unknown | | LKB1 wt |

TABLE 3-continued

Lnc473 expression in human NSCLC cell lines from CCLE database and their associated LKB1 mutation status. All samples had primary site of lung and histology of carcinoma.

| Cell line primary name | RMA (Log2) | Gender | Hist Subtype1 | LKB1 status | LKB1 mutation (#) | Predicted by a 16-gene score (##) |
|---|---|---|---|---|---|---|
| Calu-6 | 4.434085 | F | undifferentiated_carcinoma | wt | WT | LKB1 wt |
| HARA | 4.360481 | M | squamous_cell_carcinoma | Unknown | | LKB1 wt |
| KNS-62 | 4.312017 | M | squamous_cell_carcinoma | wt | WT | LKB1 wt |
| NCI-H1838 | 4.282615 | F | non_small_cell_carcinoma | wt | WT | LKB1 wt |
| LC-1/sq-SF | 4.266397 | M | squamous_cell_carcinoma | Unknown | | LKB1 wt |
| HCC-2108 | 4.262532 | M | adenocarcinoma | Unknown | | |
| LXF-289 | 4.26104 | M | adenocarcinoma | wt | WT | LKB1 loss |
| NCI-H322 | 4.254947 | M | adenocarcinoma | wt | WT | LKB1 wt |
| HCC-827-GR5 | 4.251327 | | adenocarcinoma | wt | WT | |
| HCC-1359 | 4.230968 | F | large_cell_carcinoma | wt | WT | |
| RERF-LC-KJ | 4.229279 | M | non_small_cell_carcinoma | Unknown | | LKB1 loss |
| IA-LM | 4.213694 | M | large_cell_carcinoma | wt | WT | LKB1 wt |
| NCI-H520 | 4.154591 | M | squamous_cell_carcinoma | wt | WT | LKB1 wt |
| CAL-12T | 4.130446 | M | non_small_cell_carcinoma | wt | WT | LKB1 loss |
| LC-1F | 4.118675 | M | squamous_cell_carcinoma | wt | WT | LKB1 wt |
| HCC-95 | 4.111587 | M | squamous_cell_carcinoma | wt | WT | LKB1 wt |
| EPLC-272H | 4.111317 | M | squamous_cell_carcinoma | wt | WT | LKB1 wt |
| BEN | 4.109393 | M | NS | wt | WT | LKB1 loss |
| SK-LU-1 | 4.106286 | F | adenocarcinoma | wt | WT | LKB1 wt |
| NCI-H2085 | 4.100357 | M | adenocarcinoma | Unknown | | LKB1 wt |
| HLC-1 | 4.093439 | | adenocarcinoma | Unknown | | LKB1 loss |
| EBC-1 | 4.088854 | M | squamous_cell_carcinoma | Unknown | | LKB1 wt |
| NCI-H2291 | 4.088074 | M | adenocarcinoma | wt | WT | LKB1 wt |
| LK-2 | 4.082802 | M | squamous_cell_carcinoma | wt | WT | LKB1 wt |
| NCI-H1573 | 4.077617 | F | adenocarcinoma | mutant | LKB1 loss, NOS | LKB1 loss |
| NCI-H650 | 4.065019 | M | bronchioloalveolar_adenocarcinoma | wt | WT | LKB1 wt |
| RERF-LC-AI | 4.059075 | M | squamous_cell_carcinoma | Unknown | | LKB1 wt |
| SW 900 | 4.038099 | M | squamous_cell_carcinoma | wt | WT | LKB1 wt |
| NCI-H2087 | 4.033823 | M | adenocarcinoma | wt | WT | LKB1 wt |
| NCI-H2342 | 4.029915 | M | adenocarcinoma | wt | WT | LKB1 wt |
| NCI-H3255 | 4.026813 | F | adenocarcinoma | wt | WT | LKB1 wt |
| NCI-H1373 | 4.024774 | M | adenocarcinoma | Unknown | | LKB1 wt |
| HCC-78 | 4.018615 | M | adenocarcinoma | wt | WT | LKB1 wt |
| HCC-1195 | 4.01556 | M | mixed_adenosquamous_carcinoma | Unknown | | LKB1 loss |
| NCI-H854 | 4.014536 | | adenocarcinoma | Unknown | | LKB1 loss |
| ABC-1 | 3.994741 | M | non_small_cell_carcinoma | wt | WT | LKB1 wt |
| RERF-LC-Ad1 | 3.993486 | M | adenocarcinoma | Unknown | | LKB1 loss |
| NCI-H1299 | 3.992889 | M | non_small_cell_carcinoma | wt | WT | LKB1 wt |
| HCC-1897 | 3.990146 | | squamous_cell_carcinoma | Unknown | | |
| RERF-LC-Sq1 | 3.986817 | F | squamous_cell_carcinoma | Unknown | | LKB1 wt |
| LCLC-97TM1 | 3.986306 | M | large_cell_carcinoma | wt | WT | LKB1 wt |
| RERF-LC-Ad2 | 3.975413 | M | adenocarcinoma | Unknown | | LKB1 wt |
| NCI-H1869 | 3.972442 | M | squamous_cell_carcinoma | Unknown | | LKB1 wt |
| Hs 618.T | 3.970786 | F | adenocarcinoma | Unknown | | LKB1 wt |
| HCC-2814 | 3.970314 | | squamous_cell_carcinoma | Unknown | | |
| NCI-H1793 | 3.95608 | M | non_small_cell_carcinoma | wt | WT | LKB1 wt |
| NCI-H1155 | 3.954891 | M | large_cell_carcinoma | wt | WT | LKB1 loss |
| NCI-H2170 | 3.95321 | M | squamous_cell_carcinoma | wt | WT | LKB1 loss |
| NCI-H1792 | 3.944311 | M | adenocarcinoma | wt | WT | LKB1 wt |
| NCI-H596 | 3.940438 | M | mixed_adenosquamous_carcinoma | wt | WT | LKB1 wt |
| NCI-H441 | 3.93946 | M | adenocarcinoma | wt | WT | LKB1 wt |
| COR-L23 | 3.917462 | M | large_cell_carcinoma | wt | WT | LKB1 wt |
| Sq-1 | 3.915144 | | squamous_cell_carcinoma | Unknown | | LKB1 wt |
| NCI-H226 | 3.913636 | M | squamous_cell_carcinoma | wt | WT | LKB1 wt |
| HCC-366 | 3.911762 | F | mixed_adenosquamous_carcinoma | mutant | Large deletion, NOS | LKB1 wt |
| HCC-1588 | 3.911081 | F | squamous_cell_carcinoma | Unknown | | |
| SW 1573 | 3.90113 | F | squamous_cell_carcinoma | wt | WT | LKB1 wt |
| SK-MES-1 | 3.88507 | M | squamous_cell_carcinoma | wt | WT | LKB1 wt |
| NCI-H1781 | 3.880625 | F | bronchioloalveolar_adenocarcinoma | Unknown | | LKB1 wt |
| NCI-H1975 | 3.878402 | F | non_small_cell_carcinoma | wt | WT | LKB1 wt |
| NCI-H2228 | 3.87466 | F | adenocarcinoma | wt | WT | LKB1 wt |
| NCI-H358 | 3.874099 | M | bronchioloalveolar_adenocarcinoma | wt | WT | LKB1 wt |
| Calu-1 | 3.872414 | M | squamous_cell_carcinoma | wt | WT | LKB1 wt |
| NCI-H1650 | 3.866959 | M | bronchioloalveolar_adenocarcinoma | wt | WT | LKB1 wt |
| NCI-H1703 | 3.859445 | M | adenocarcinoma | wt | WT | LKB1 wt |
| Calu-3 | 3.858251 | M | adenocarcinoma | wt | WT | LKB1 wt |
| HLF-a | 3.857518 | F | squamous_cell_carcinoma | Unknown | | LKB1 wt |
| NCI-H2405 | 3.854325 | M | adenocarcinoma | wt | WT | LKB1 wt |
| NCI-H1581 | 3.852179 | M | large_cell_carcinoma | wt | WT | LKB1 wt |
| HCC-2279 | 3.848194 | F | adenocarcinoma | wt | WT | LKB1 wt |

TABLE 3-continued

Lnc473 expression in human NSCLC cell lines from CCLE database and their associated LKB1 mutation status. All samples had primary site of lung and histology of carcinoma.

| Cell line primary name | RMA (Log2) | Gender | Hist Subtype1 | LKB1 status | LKB1 mutation (#) | Predicted by a 16-gene score (##) |
|---|---|---|---|---|---|---|
| NCI-H2106 | 3.839763 | M | non_small_cell_carcinoma | Unknown | | LKB1 wt |
| HCC827 | 3.835911 | F | adenocarcinoma | Unknown | | LKB1 wt |
| HCC2935 | 3.834708 | M | non_small_cell_carcinoma | wt | WT | LKB1 wt |
| NCI-H2009 | 3.8344 | F | adenocarcinoma | wt | WT | LKB1 wt |
| NCI-H1693 | 3.824201 | F | adenocarcinoma | wt | WT | LKB1 wt |
| NCI-H522 | 3.811081 | M | non_small_cell_carcinoma | wt | WT | LKB1 wt |
| HCC364 | 3.806596 | | adenocarcinoma | Unknown | | |
| LU99 | 3.791267 | M | large_cell_carcinoma | Unknown | | LKB1 wt |
| HCC-1438 | 3.786822 | M | large_cell_carcinoma | Unknown | | |
| LCLC-103H | 3.766306 | M | large_cell_carcinoma | wt | WT | LKB1 wt |
| NCI-H661 | 3.752467 | M | large_cell_carcinoma | wt | WT | LKB1 wt |
| NCI-H1435 | 3.748322 | F | non_small_cell_carcinoma | Unknown | | LKB1 loss |
| NCI-H2347 | 3.745148 | F | adenocarcinoma | wt | WT | LKB1 wt |
| VMRC-LCP | 3.741747 | | squamous_cell_carcinoma | mutant | LKB1 loss, NOS | LKB1 loss |
| LOU-NH91 | 3.734531 | F | squamous_cell_carcinoma | Unknown | | LKB1 wt |
| PC-14 | 3.706141 | | non_small_cell_carcinoma | wt | WT | LKB1 wt |
| HCC4006 | 3.657913 | M | adenocarcinoma | wt | WT | LKB1 wt |
| HCC-1833 | 3.646418 | | adenocarcinoma | Unknown | | |
| NCI-H2444 | 3.609546 | M | non_small_cell_carcinoma | Unknown | | LKB1 wt |
| NCI-H1648 | 3.599074 | M | adenocarcinoma | wt | WT | LKB1 wt |
| HCC-1171 | 3.578131 | M | non_small_cell_carcinoma | wt | WT | LKB1 wt |

(#): References Jemal et al., Janku et al., Koivunen et al., Paez et al., Shackelford et al., Alessi et al. and Hemminki et al.
(##): Reference Hemminki et al.

EXAMPLE 5—LINC00473 EXPRESSION IS ELEVATED IN NSCLC THAT HAVE MUTATIONS IN THE LKB1 GENE CODING REGIONS

Figure 6A:
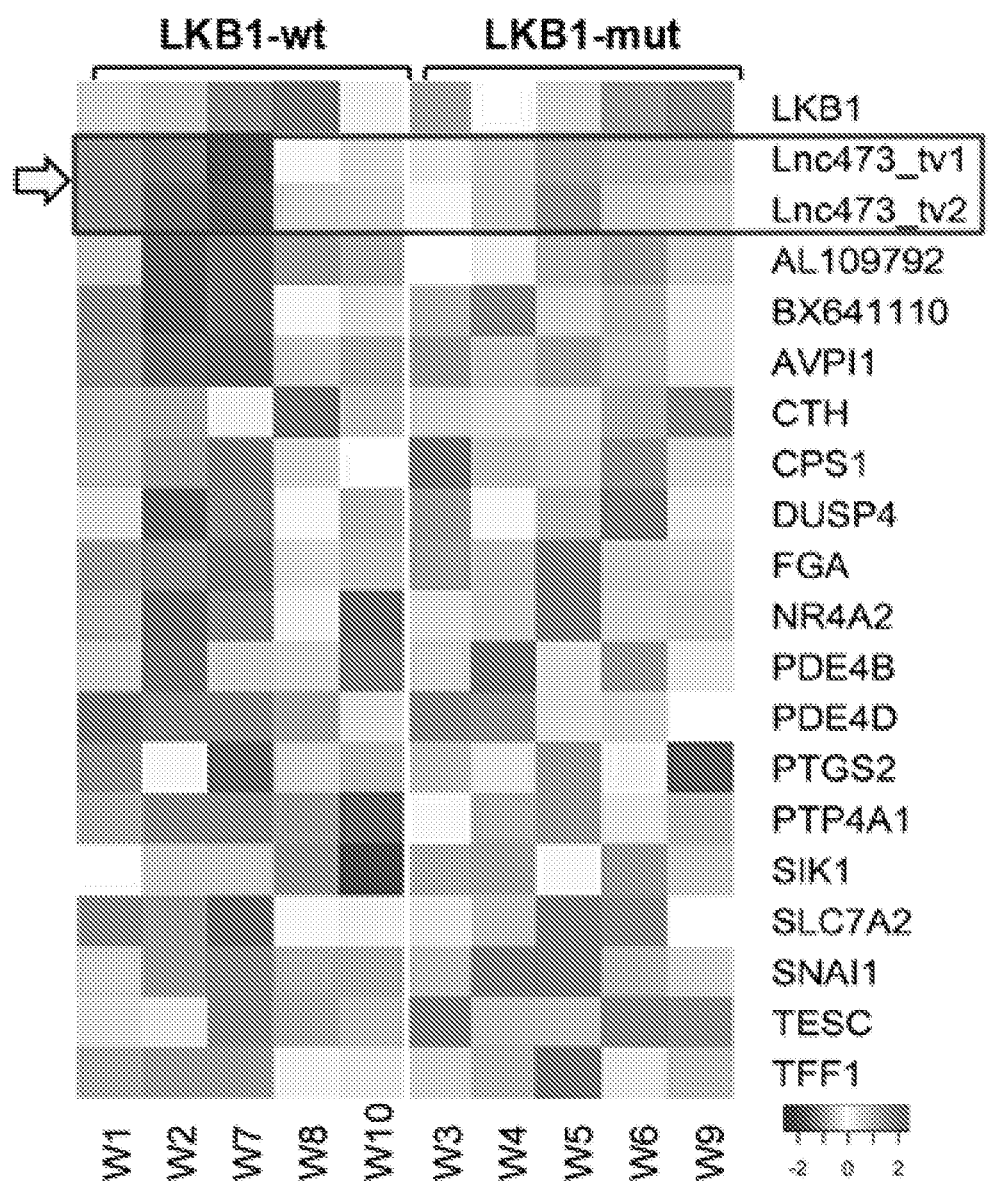
FIGS. 6A-6G. Enhanced LINC00473 expression highly correlates with human lung adenocarcinoma with LKB1 mutational status and is associated with poor survival. (A) A heatmap shows gene expression levels in RNA samples isolated from 5 LKB1-wt and 5 LKB1-mut FFPE LUAD samples in Nanostring assays. (B) Expression of LINC00473 transcript variant (tv1), but not tv2, was significantly different between LKB1-wt and -mut groups. (C,D) Representative images for tumors with LINC00473 positive (C) and negative (D) signals based on RNAscope detection on FFPE LUAD sections. RNA in-situ hybridization (ISH) of the housekeep gene PPIB was performed for sample RNA quality control. (E) Survey of human LUAD arrays indicated that 0% of normal lung tissues (n=38), 10.11% of NSCLC tumors with annotated wild-type LKB1 (n=89), and 55.54% of NSCLC tumors with annotated LKB1 mutations (n=22) were positive for LINC00473 expression. Only those tissues positive for the housekeeping gene PPIB expression were included in this analysis. LINC00473 expression positively correlated with LKB1 mutations based on Fisher Exact Test (p=1.93E-05). (F) TCGA-LUAD dataset showed outlier LINC00473 expression in matched tumor (T) (n=57) compared to adjacent normal tissues (N) (n=57) as well as unpaired tumor (UT) (n=454). (G) Kaplan-Meier survival analysis of high LINC00473 expression (n=48) and low LINC00473 expression (n=421) in lung cancer patients ($p<0.001$). See also FIGS. 12-15.
Figure 6B:
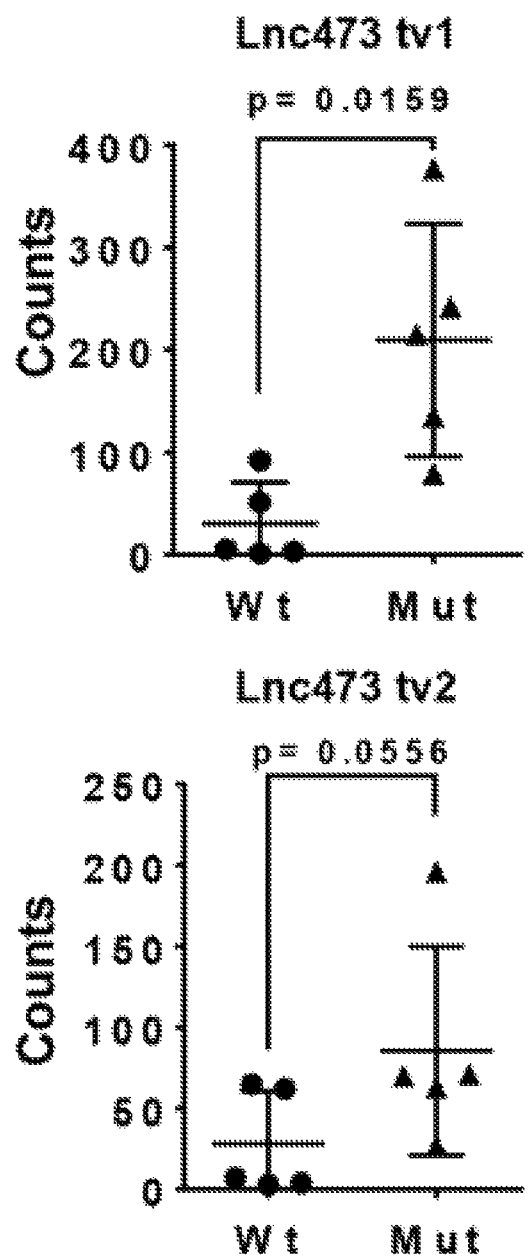

To investigate whether LINC00473 can serve as a potential biomarker for LKB1 status in human NSCLC cancers, expression of LINC00473 and several other LKB1 targets was evaluated in formalin-fixed paraffin-embedded (FFPE) human adenocarcinoma (LUAD) specimens. Target amplification-based strategies such as RT-PCR and microarray analyses for measuring RNA levels from fixed tissue is complicated by the fact that the RNA is highly cross-linked and significantly fragmented. Nanostring-based assays are optimal for gene expression quantification using FFPE tumor-derived RNA samples since the bar-coded fluorescent probes recognize small target regions (~100 bp) allowing direct single-molecule counting without need for target amplification. Therefore, Nanostring assays were performed for FFPE tumor-derived RNAs from 5 LKB1-wt and 5 LKB1-mut human LUAD specimens. The LKB1 gene mutation status was analyzed by exon sequencing. LINC00473 expression was consistently found to best correlate with the tumor LKB1 status among all the genes tested (FIG. 6A). Expression of LINC00473 tv1, but not tv2, was significantly enhanced in LUAD with LKB1 mutations (FIG. 6B). These data suggest that expression of LINC00473 tv1 alone can predict tumor LKB1 status.

Figure 6C:
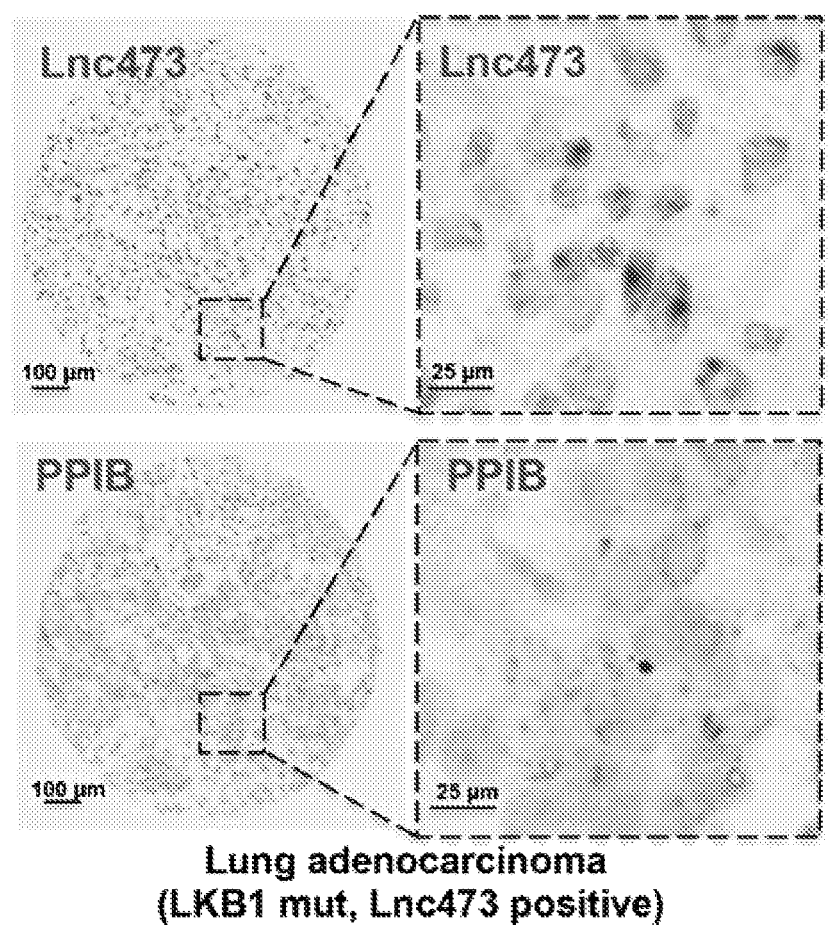
Figure 6D:
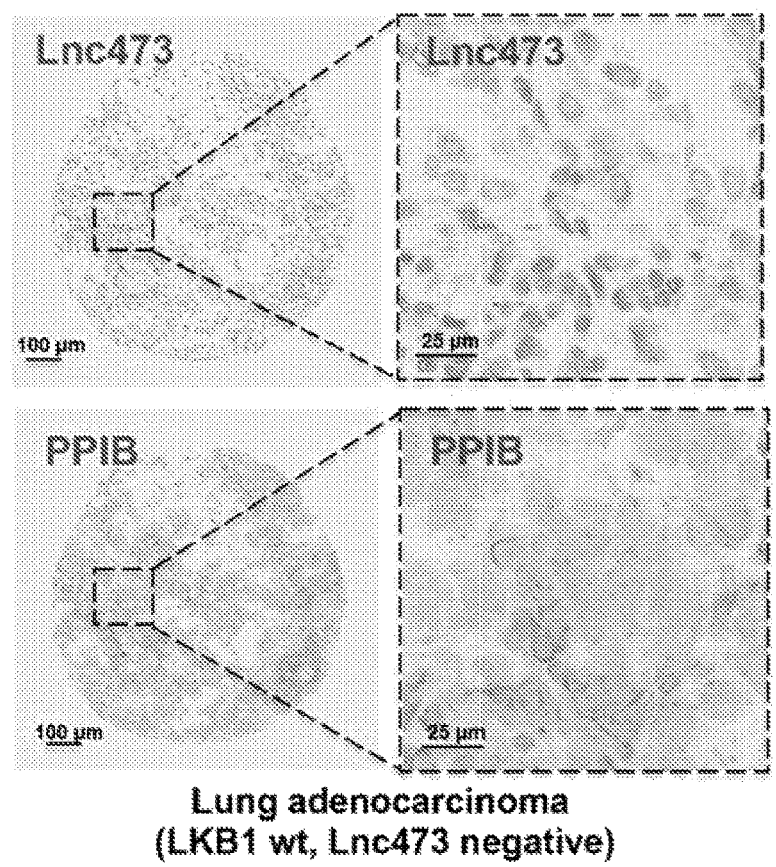
Figure 6E:
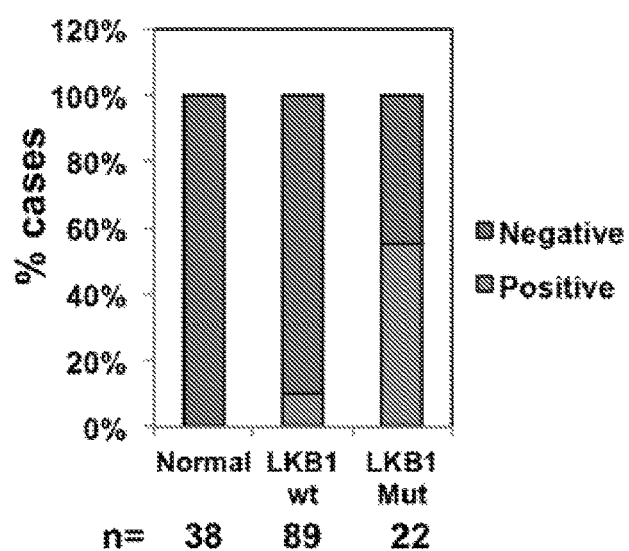

To examine whether LINC00473 expression could be directly visualized at cellular levels in human FFPE tumors, RNA in situ hybridizations (RNA ISH) was performed for detection of LINC00473 transcripts using customized LINC00473 probes (RNAscope). The specificity of LINC00473 probes was first validated by positive LINC00473 signals in LKB1-null A549 xenograft tumors and negative signals in LKB1-wt H522 xenograft tumors. LINC00473 transcripts were detected as easily distinguishable nuclear "dots" in A549 xenograft tumors. RNA ISH was the performed on FFPE human LUAD tissue array. This array also included FFPE cell pellets from LKB1-null A549 and LKB1-positive H322 as controls, which showed respective positive and negative LINC00473 signals. Only those tumors were analyzed that were positive for a housekeeping gene PPIB (peptidylprolyl isomerase), indicative of tumors with good RNA quality. Representative positive and negative LINC00473 staining results were shown (FIGS. 6C, D). All normal human lung tissues (n=38) were negative for LINC00473 staining while exhibiting positive staining for PPIB staining (FIG. 6E), indicating absent or low basal LINC00473 expression in normal lung tissues. 9 out of 89 NSCLC specimens (10.11%) with annotated LKB1 wt and 12 out of 22 lung tumors (54.54%) with annotated LKB1 mutations were positive for LINC00473 staining (FIG. 6E). LINC00473 expression showed significant positive correlation with LKB1 mutations based on Fisher Exact Test (p=1.93E-05). It is likely that those tumors carrying the LKB1 wt gene yet showing elevated LINC00473 expression have LKB1 functional inactivation due to other mechanisms besides LKB1 mutations such as epigenetic silencing, or post-translational modifications, or alteration in LKB1 signaling components. On the other hand, not all mutations found in LKB1 are inactivating. Tumors carrying the LKB1 gene mutations yet not showing LINC00473 induction could have intact LKB1 function if the mutations do not impair LKB1 function. For example, one of the tumors with LKB1 F354L mutation, which was predicted not to have damaging effects on LKB1 function based on PolyPhen-2 prediction, showed undetectable LINC00473 expression. In addition, negative LINC00473 staining was found in several other cancer types and tissues including prostate cancer, IDC breast, large cell Lymphoma, hepatocellular carcinoma, colon adenocarcinoma and osteosarcoma as well as placenta, tonsil, and normal spleen (n=1; data not shown). These data strongly indicate that LINC00473 is low or undetectable in normal lung tissues but exhibits elevated expression in the subset of lung NSCLC specifically with functional LKB1 inactivation, indicating that LINC00473 is a potential robust surrogate biomarker for LKB1 functional status in lung cancer.

EXAMPLE 6—ELEVATED LINC00473 EXPRESSION IS ASSOCIATED WITH TUMOR LKB1 MUTATIONS AND CORRELATES WITH POOR PROGNOSIS IN TCGA LUNG ADENOCARCINOMAS

Figure 6F:
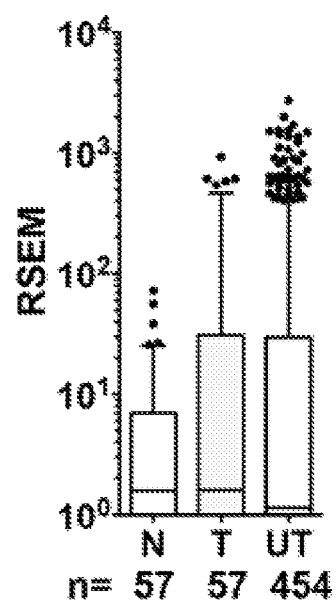
Figures 12A, 12B, 12C:
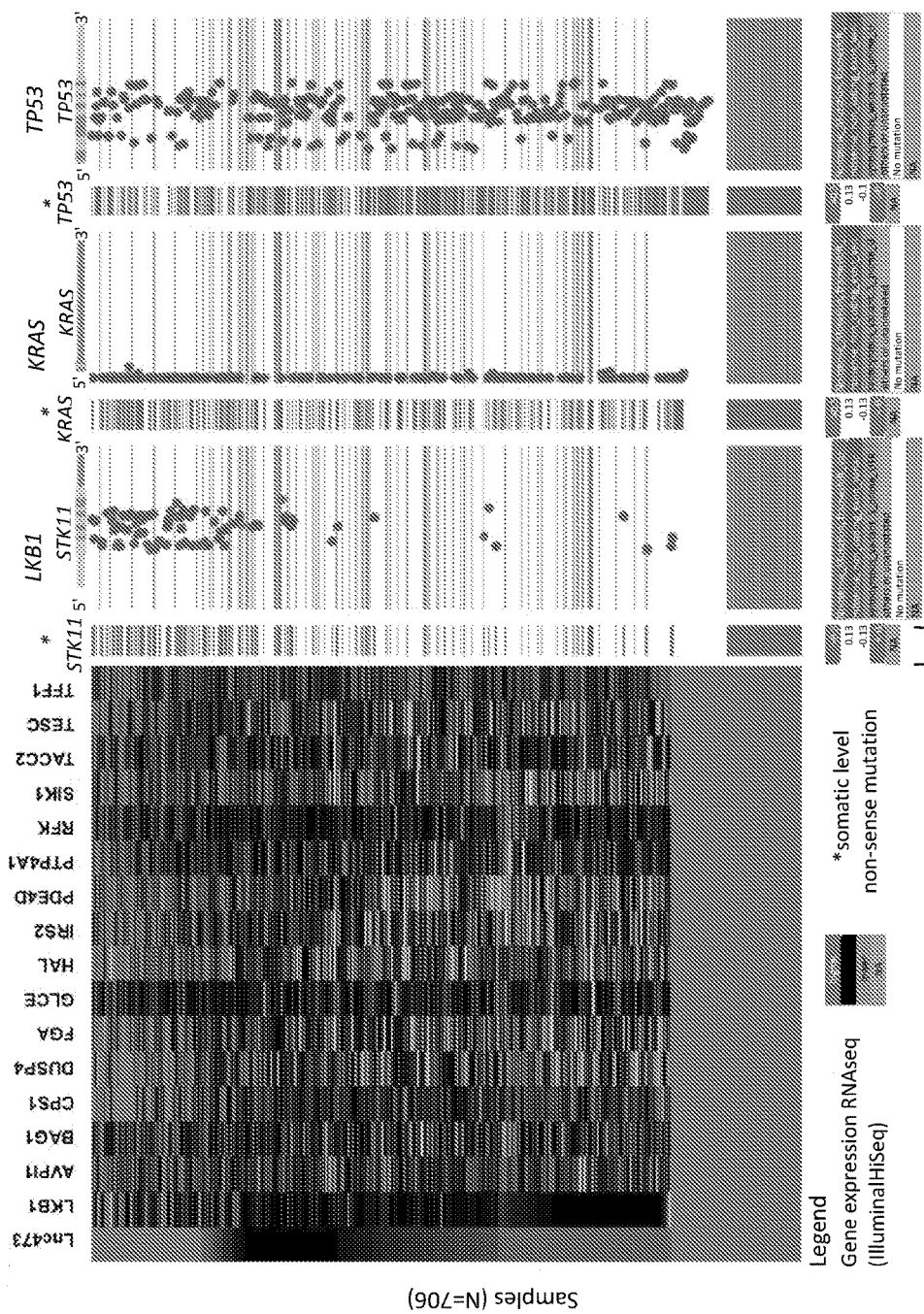
FIGS. 12A-12C. Human lung adenocarcinomas with high LINC00473 expression were enriched with mutations in the LKB1 gene coding region. (A) Expression patterns of LINC00473 and other genes in TCGA LUAD samples. Data was sorted by normalized expression value. Samples with high expression are red, samples with low expression are green, and samples with no expression data are grey. (B) LKB1 gene-level non-silent mutations in LUAD samples. Red means that a non-silent mutation was found in the gene. White means that no such mutation was found. Gray means that the sample has no data. (C) Somatic mutation SNPs and small INDELs in LKB1, KRAS and TP53 genes in LUAD samples. Each colored dot shows a mutation along the transcript with each line being its own sample. Red indicates that the mutation is likely to prevent a functional protein from being made (nonsense mutations, frame shift, etc.). Blue indicates that the protein is likely to be made, but may have an altered function (missense mutation, etc.). Green indicates that the protein is unlikely to be affected (such as synonymous).
Figure 13C:
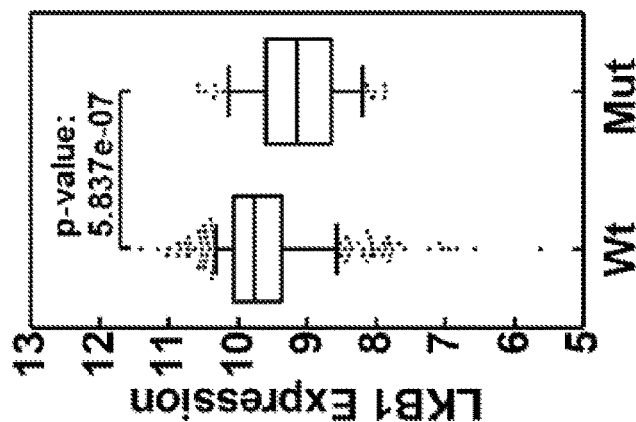
FIGS. 13A-13C. Box plots show expression levels of LINC00473 (A), SIK1 (B), and LKB1 (C) genes in LKB1 mutant (Mut) and wildtype (Wt) human lung adenocarcinomas. The LUAD level 3 RNAseqv2 normalized data were downloaded from TCGA along with the Meta-Data for each patient. The RNA-seq gene expression data were combined with DNA-sequencing data to compare gene expression to LKB1 mutational status. There were 479 patients with DNA sequencing information: 402 were WT and the other 77 were LKB1 mutant. The p-value was generated by a two tailed, independent t-test. The data indicate that LINC00473 expression is a more significantly variant between LKB1 WT and Mutant than SIK1 or LKB1.
Figure 13B:
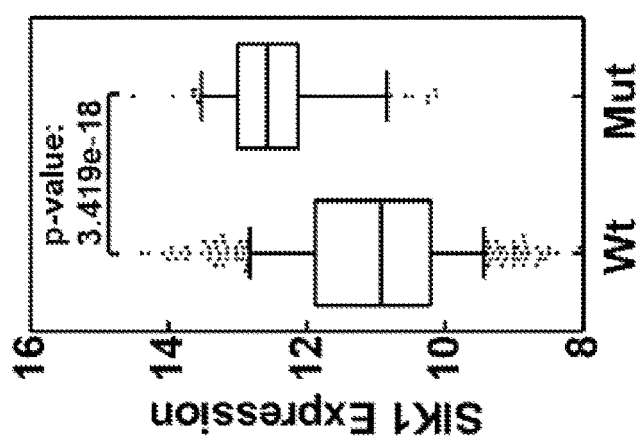
Figure 13A:
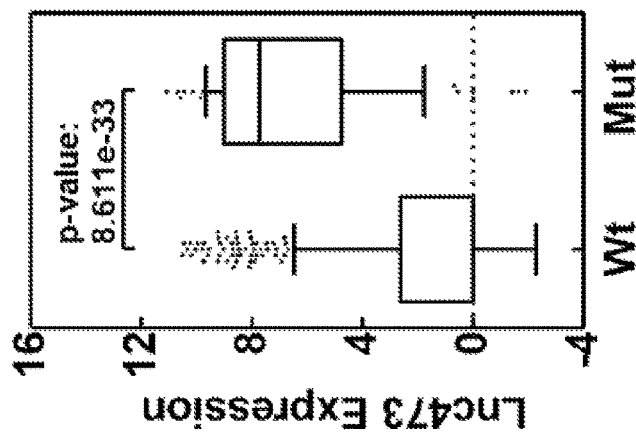
Figure 14A:
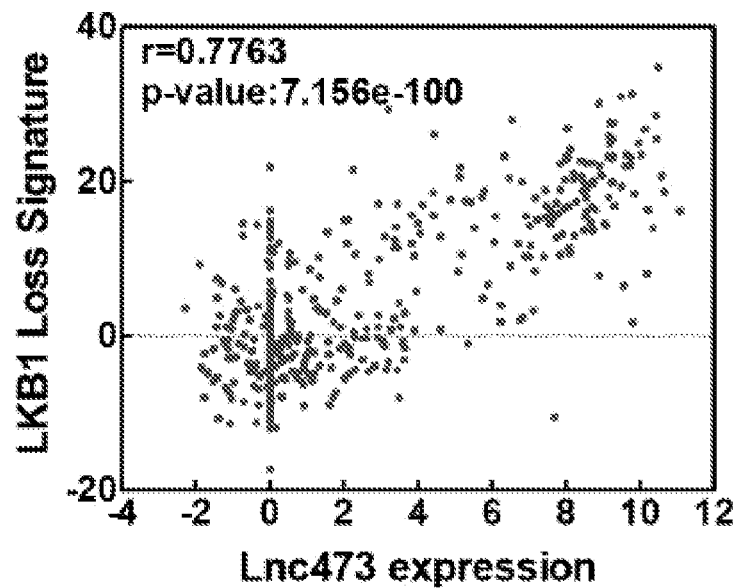
FIGS. 14A-14E. Analysis of the correlation between LINC00473 Expression, the LKB1-Loss Signature, LKB1 Expression, and SIK1 Expression. (A) Correlation of LINC00473 Gene Expression to LKB1-Loss Signature; (B) Correlation of LINC00473 Gene Expression to LKB1 Gene Expression; (C) Correlation of SIK1 Gene Expression to LKB1-Loss Signature; (D) Correlation of LKB1 Gene Expression to SIK1 expression; (E) Correlation of LKB1 Gene Expression to LKB1 Loss Signature. The data indicate that LINC00473 expression is more positively correlated with the LKB1-loss signature than SIK1 expression. The data also show that LKB1 expression is more significantly inversely correlated with LINC00473 expression than that of SIK1 expression and LKB1 expression is significantly inversely correlated with the LKB1 loss signature.
Figure 14B:
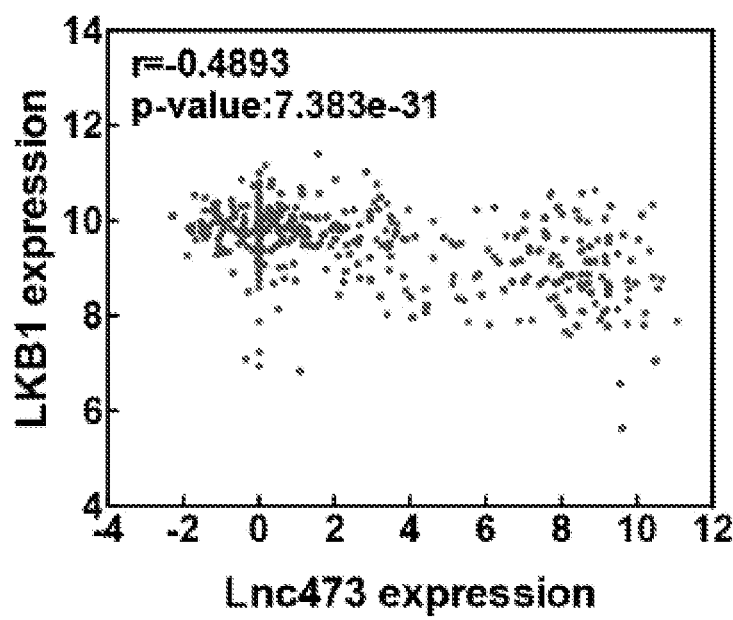
Figure 14C:
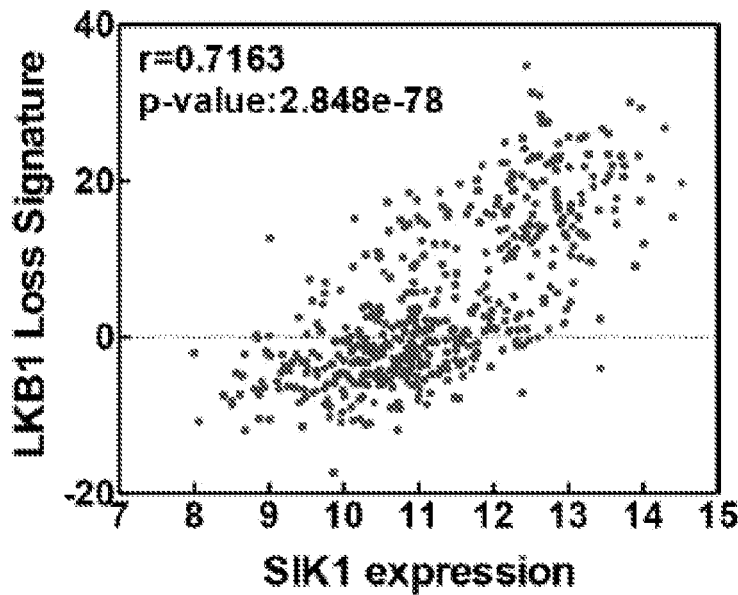
Figure 14D:
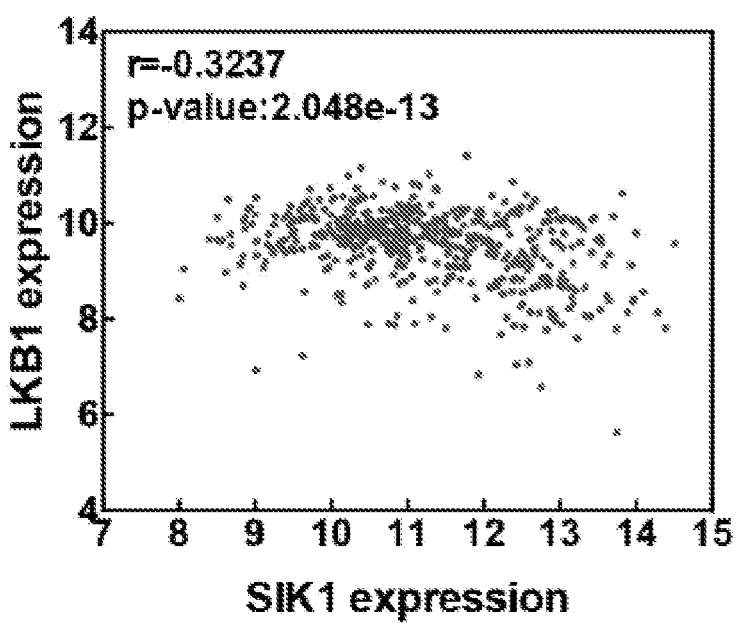
Figure 14E:
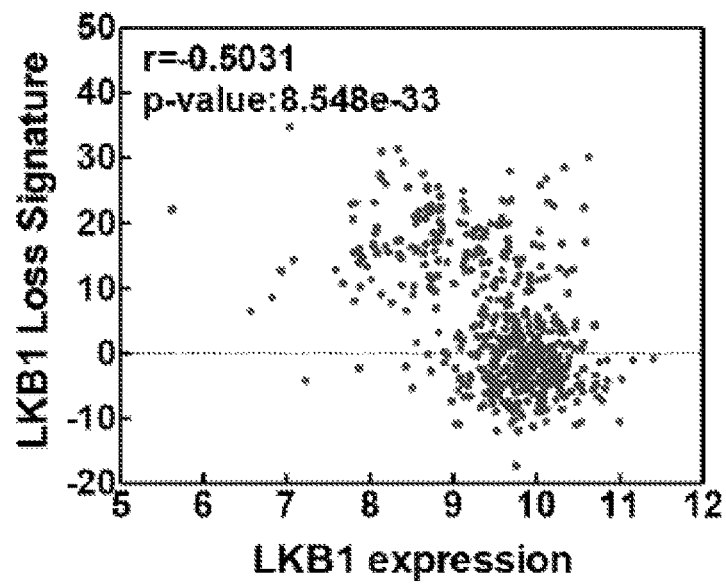

To investigate any potential association between LINC00473 expression, LKB1 mutation status, and clinical data of lung cancers, a lung adenocarcinoma (LUAD) RNAseq dataset from The Cancer Genome Atlas (TCGA) was analyzed. A subset of lung cancers with outlier LINC00473 expression (90 percentile rank) and a significant difference in LINC00473 expression between tumors (either paired n=57 or unpaired n=454) and normal tissues (n=57) (FIG. 6F) was observed. LUAD samples with high LINC00473 expression were enriched with LKB1 gene-level nonsynonymous somatic mutations including small INDELs within the LKB1 gene coding regions (FIG. 12). LINC00473 expression was not associated with KRAS and TP53 gene mutations (FIG. 12), which are two well-known somatic mutations that can occur concurrently with LKB1 loss. Moreover, the difference in LINC00473 expression between LKB1 wt and LKB1 mutant populations was more significant compared to SIK1 or LKB1 expression (FIG. 13). LINC00473 expression was positively correlated with LKB1-loss gene signature and inversely correlated with LKB1 expression, and such correlations were more significant in comparison to SIK1 expression and LKB1 expression (FIG. 14). These data support a strong association of LINC00473 expression with the LKB1 inactivation in LUAD samples.

Figure 6G:
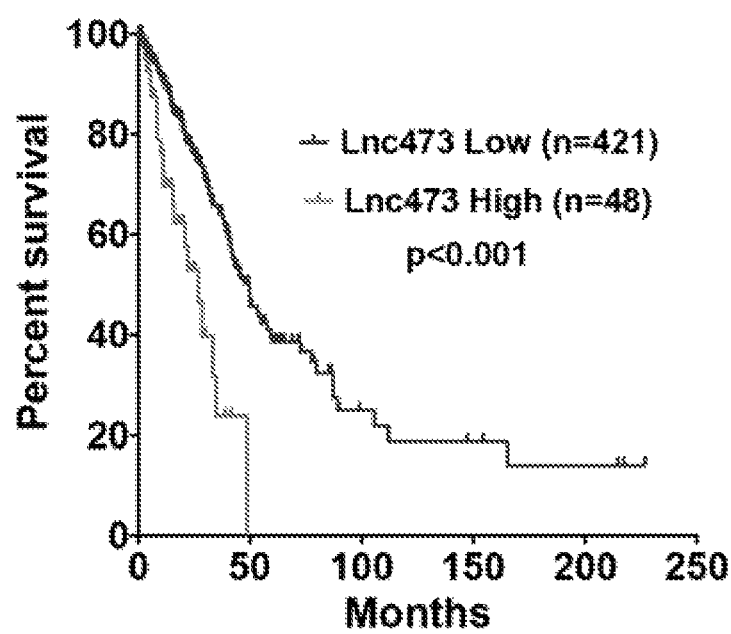
Figure 15A:
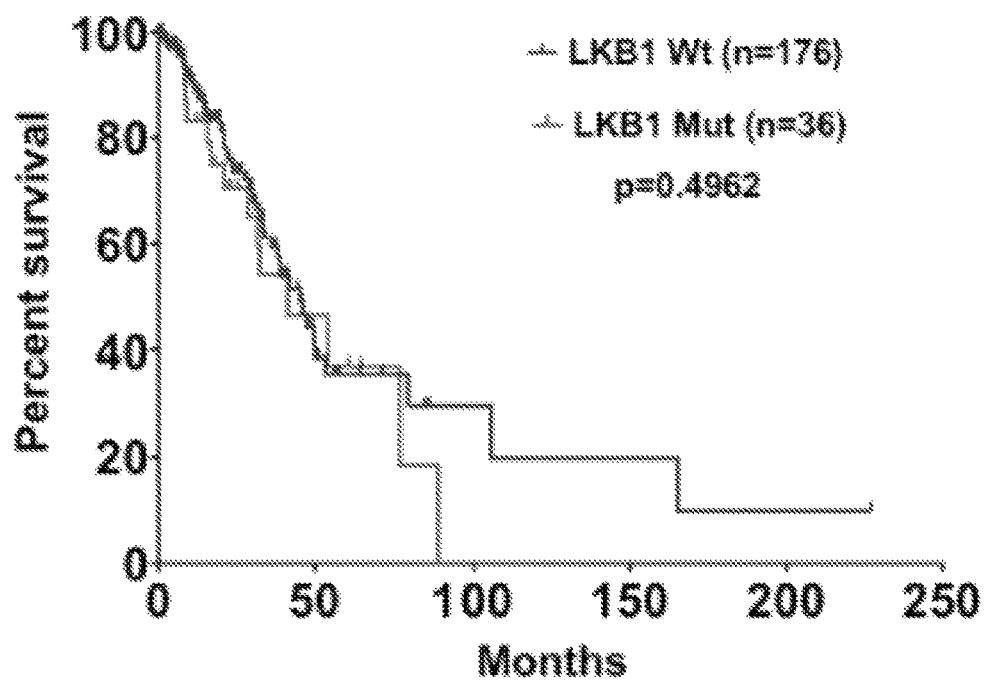
FIGS. 15A-15C. Kaplan-Meier survival analyses showed that high LINC00473 expression, but not LKB1 mutations in the coding regions, was associated with poor prognosis. (A) LKB1 mutation status was not significantly associated with survival. The tumors in TCGA-LUAD dataset with the available data on LKB1 mutations and clinical information were analyzed. (B, C) High LINC00473 expression was associated with a poor survival in both LKB1 wt and mutant groups. The tumors in TCGA-LUAD dataset with the available data on LINC00473 expression, LKB1 mutations, and clinical information were analyzed.
Figure 15B:
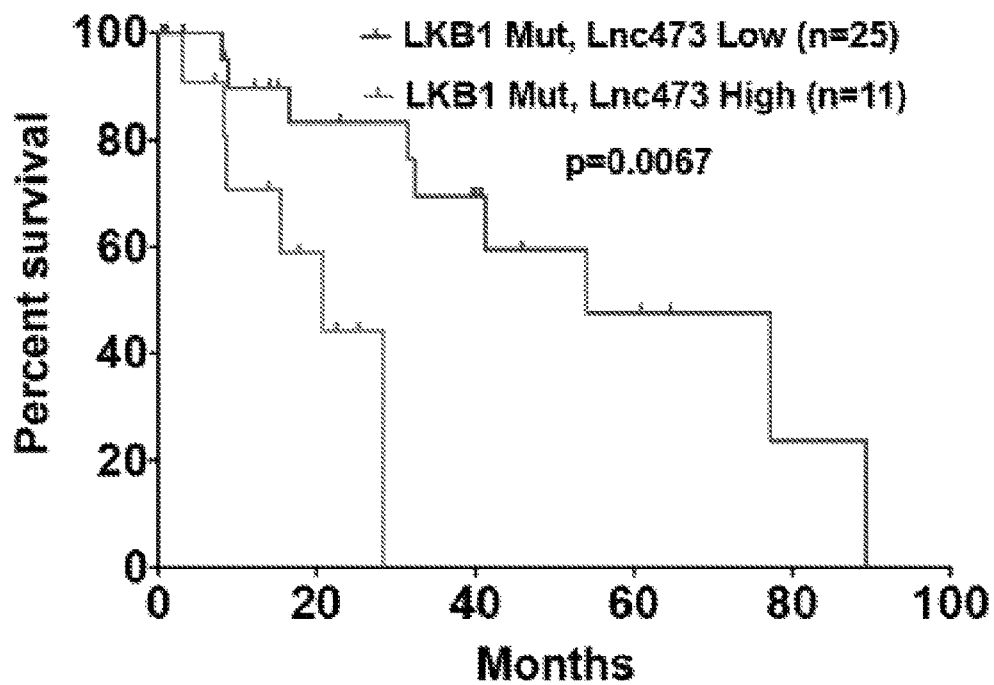
Figure 15C:
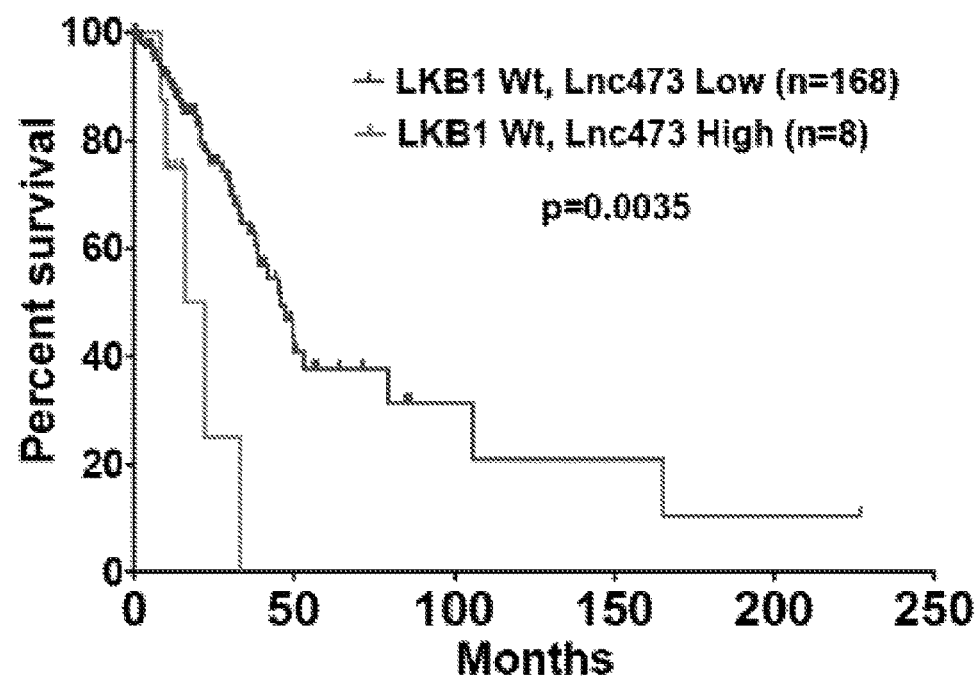

Kaplan-Meier survival analysis showed highly significant difference in overall survival between high expression (n=48) and low expression (n=421) groups (p<0.001, FIG. 6G). The elevated LINC00473 expression significantly correlated with a shorter survival time in LUAD patients (<50 months). When analyzing those tumors with the available data on LINC00473 expression, LKB1 mutations, and clinical information, LKB1 mutation status was not significantly associated with survival, but high LINC00473 expression was associated with a poor survival within both LKB1-wt and mutant groups (FIG. 15). These data indicate that LINC00473 has a prognostic value and may play an important role in cancer progression.

EXAMPLE 7—LINC00473 EXPRESSION IS PROMOTED BY LKB1-LOSS-INDUCED CRTC/CREB ACTIVATION

Figure 7A:
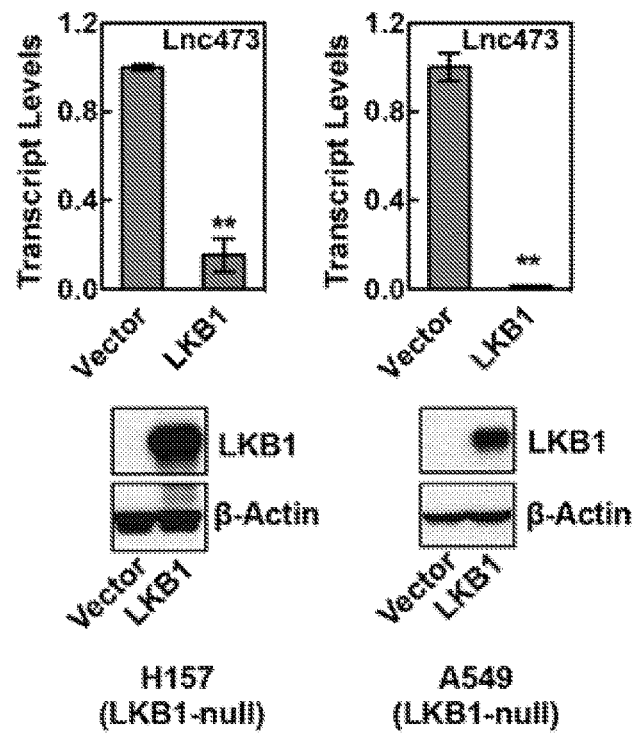
FIGS. 7A-7H. LINC00473 expression is regulated by LKB1-CRTC1-CREB signaling axis. (A) qRT-PCR analysis showed that LINC00473 expression was significantly reduced in two LKB1-null NSCLC cell lines (H157 and A549) after the transduction with LKB1 retroviruses (LKB1) for 96 hours, with cells transduced with vector retroviruses (Ctl) as controls. Western blotting confirmed LKB1 expression (n=3, **$p<0.001$). (B) LINC00473 expression was enhanced upon LKB1 shRNA lentiviral infection in two LKB1-wt NSCLC cell lines (H3123 and H322) (n=3, *$p<0.05$ and ***$p<0.0001$). (C) LINC00473 expression was significantly reduced in A549 cells after the transduction with 2 independent CREB shRNAs (n=3, *$p<0.05$). (D) A schematic representation of the LINC00473 promoter reporter is shown. (E) Expression of LKB1, but not the kinase-dead K78I mutant in LKB1-null A549 cells, caused significant repression in LINC00473 promoter reporter activity (n=3, *$p<0.05$). (F) Expression of A-CREB in A549 cells significantly inhibited the LINC00473 promoter activity (n=3, *$p<0.05$). (G) Expression of wt or constitutively activated S151A CRTC1 increased the LINC00473 promoter activity in LKB1-expressing H322 cells (n=3, $p<0.001$ and *$p<0.0001$). (H) ChIP analysis indicated that CREB and CRTC1 were significantly enriched on the LINC00473 promoter encompassing the CRE half sites in A549 cells (n=3, *$p<0.05$ and ***$p<0.0001$).
Figure 7B:
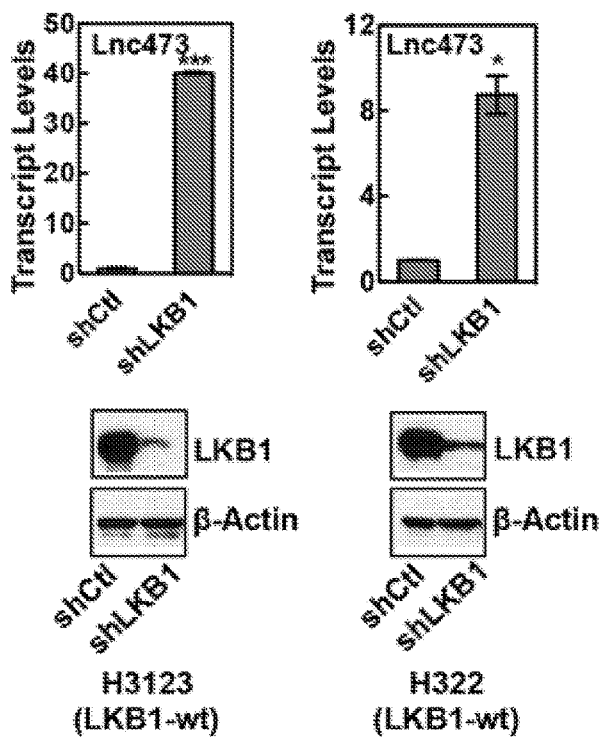

High LINC00473 expression has a positive correlation with LKB1 functional inactivation in NSCLC cell lines and human primary tumors, suggesting that LKB1 inactivation leads to increased expression of LINC00473. To further examine LKB1 regulation of LINC00473 expression, whether cellular LKB1 levels directly impacted LINC00473 expression was tested. Introduction of exogenous LKB1 in LKB1-null cancer cell lines (H157, A549) resulted in a significant decrease in LINC00473 transcript level (FIG. 7A), whereas shRNA-mediated depletion of endogenous LKB1 expression in LKB1-positive cells (H3123, H322) led to an increase in LINC00473 level (FIG. 7B). Therefore, modulating cellular LKB1 protein expression affects LINC00473 expression in NSCLC cells.

Figure 7C:
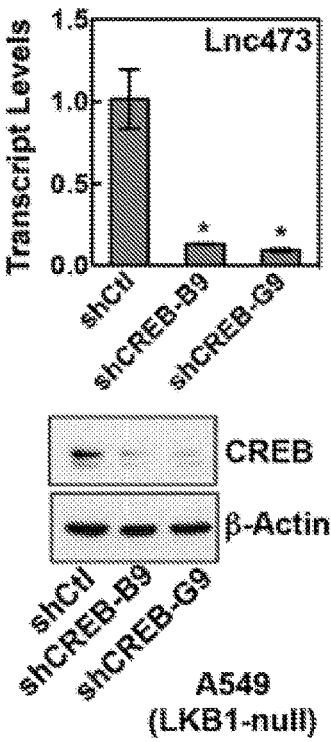
Figure 7D:
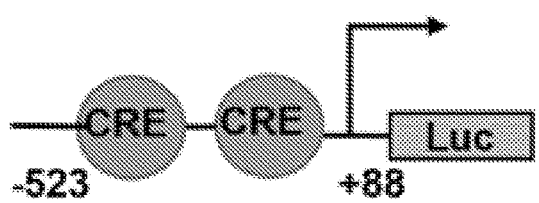
Figure 7E:
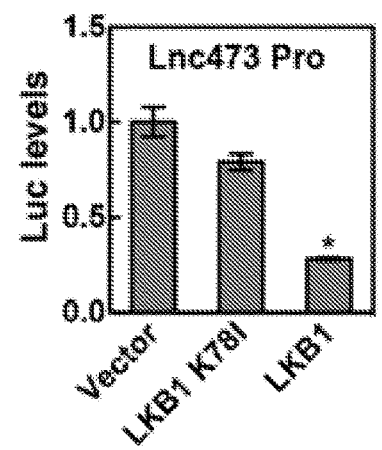
Figure 7F:
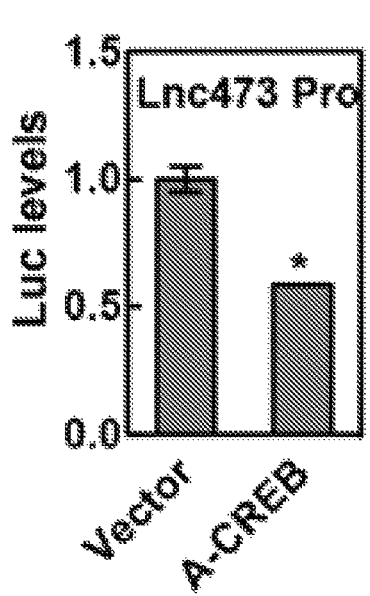
Figure 7G:
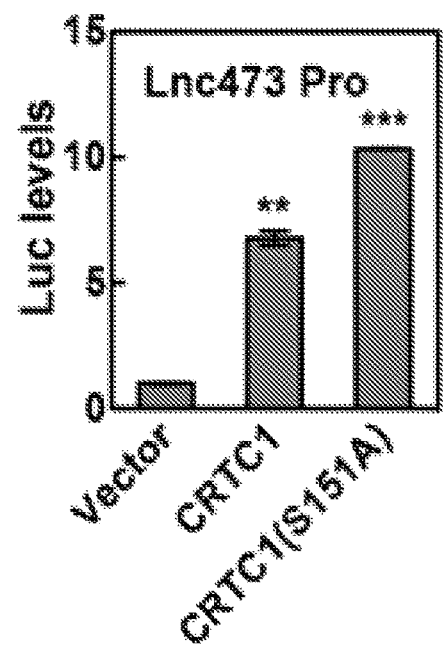
Figure 7H:
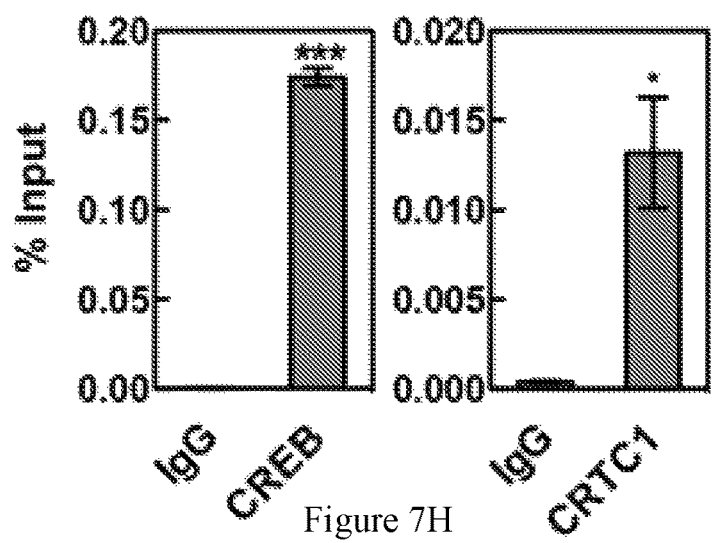

LKB1 regulates multiple downstream AMPK family members, influencing multiple signaling pathways. The loss of LKB1 expression resulted in dephosphorylation and nuclear entry of CRTC transcriptional co-activators and subsequent CREB-mediated transcriptional activation in both lung and esophageal cancer cells. LINC00473 was transiently up-regulated in response to cAMP signaling in human ocular ciliary smooth muscle cells. The LINC00473 gene contains 2 CRE (cAMP-responsive element) half sites within the proximal promoter region. To test whether the loss of LKB1 induces CRTC-CREB activation and promotes LINC00473 expression, CREB was depleted using lentiviral-mediated shRNAs or expression of a dominant negative form of CRTC (dnCRTC) that interferes with CRTC-CREB interaction. A reduction in LINC00473 transcript level was observed in CREB-depleted or dnCRTC-expressing A549 cells (FIG. 7C). LKB1 over-expression further blocked LINC00473 expression. These data demonstrate that LINC00473 is regulated by LKB1 loss and CRTC/CREB activation. Next, the proximal LINC00473 promoter sequence (−523 to +88) encompassing 2 CRE sites was cloned into the upstream region of a luciferase reporter (pGL3 basic) (FIG. 7D) and LINC00473 promoter activity was determined by modulating LKB1-CRTC-CREB signaling. The LINC00473 promoter reporter was significantly repressed by over-expression of LKB1, but not LKB1 kinase-dead mutant K78I when transfected in LKB1-deficient A549 cells (FIG. 7E). Moreover, promoter activity was significantly inhibited by expression of A-CREB (FIG. 7F), a dominant-negative mutant that specifically blocked CREB binding to DNA. Also, the LINC00473 promoter reporter was activated by over-expression of CRTC1 and to a larger extent, by constitutively activated form of CRTC1 (S151A) (FIG. 7G). Finally, chromatin immunoprecipitation (ChIP) assays demonstrated that CRTC1 and CREB were enriched in the LINC00473 promoter region spanning the CRE sites (FIG. 7H). These data suggest that LINC00473 transcription is directly induced by CRTC-CREB activation in LKB1-inactivated NSCLC cells.

EXAMPLE 8—IN VITRO AND IN VIVO APPROACHES REVEALED CRITICAL FUNCTIONS OF LINC00473 IN THE GROWTH OF LKB1-NULL LUNG CANCER CELLS

Figure 8A:
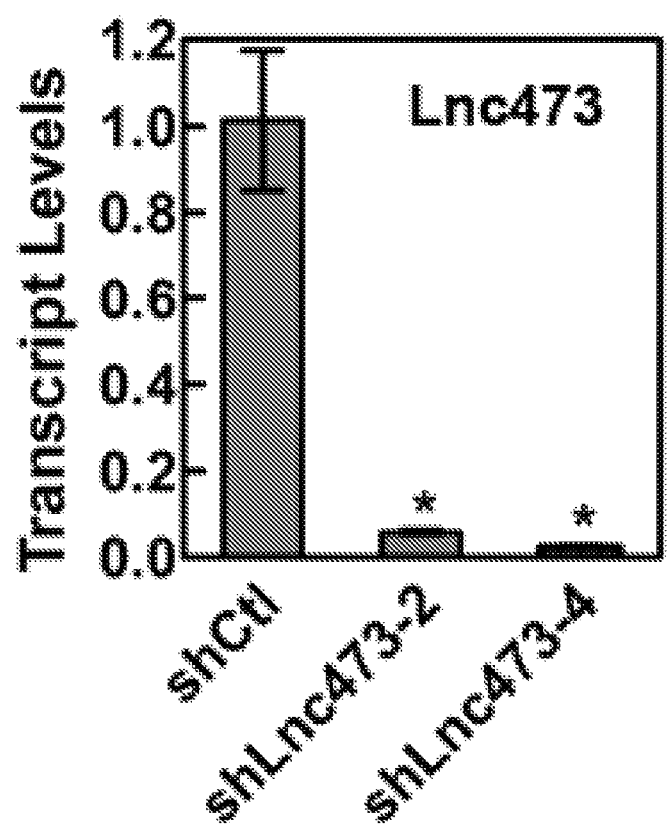
FIGS. 8A-8E. Depletion of LINC00473 expression in LKB1-null NSCLC cells causes reduced cell growth and survival in vitro and in vivo. (A) Luciferase-expressing A549 cells were infected with two independent lentiviral-based LINC00473 shRNAs and the scrambled shRNA control (shCtl), respectively. Transduced cells were harvested 96 hours later, and LINC00473 expression was quantified by qRT-PCR (n=3, *$p<0.05$). (B, C) Transduced cells at 96 hours post-transduction were cultured at $2\times10^5$ per well in 6-well plates for another 96 hours and viable cell number was measured using Trypan blue assay (B) and apoptotic cells were detected by Annexin V/PI staining (C) (n=3, *$p<0.05$ and **$p<0.001$). (D) A total of $1\times10^6$ A549-luc cells after transduction with shLINC00473 or shCtl for 72 hours were injected subcutaneously to the dorsal flanks of NOD-SCID mice. The weights of excised tumors at the end points are shown. (E) Immunohistochemical staining of A549-control and A549-shLINC00473 xenograft tumor sections with Ki-67 antibody. See also FIGS. 16-17.
Figure 8B:
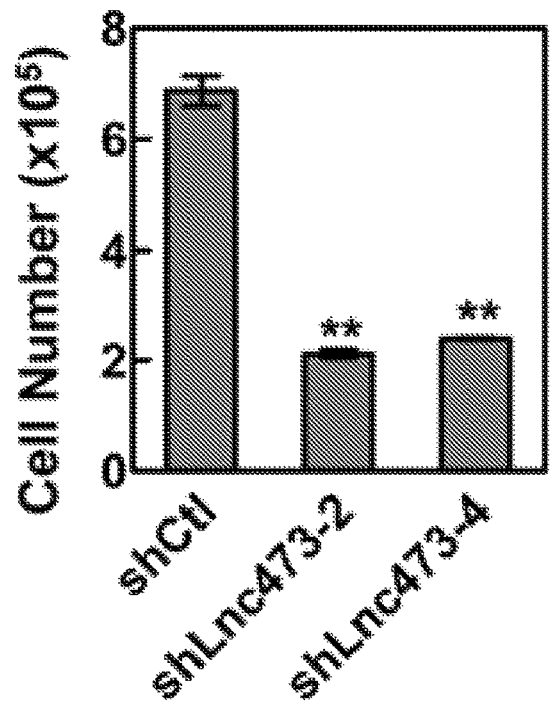
Figure 8C:
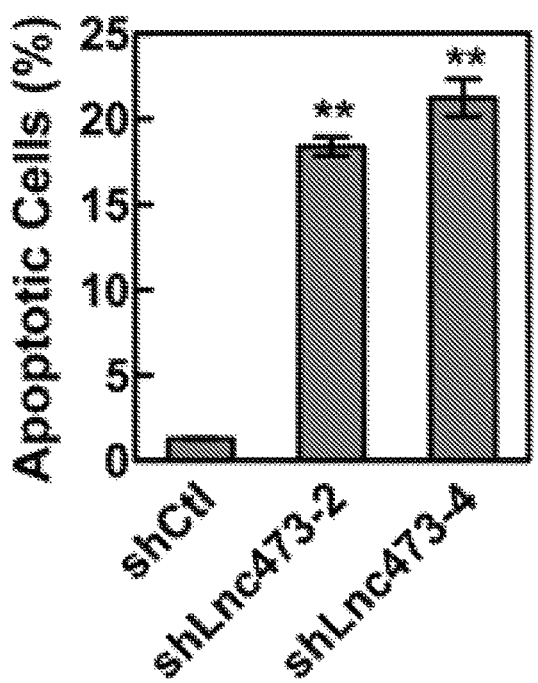
Figure 8D:
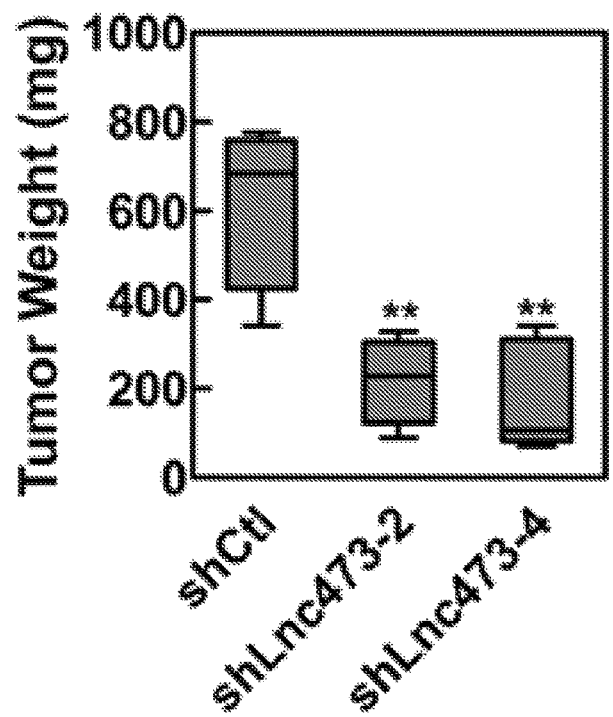
Figure 16A:
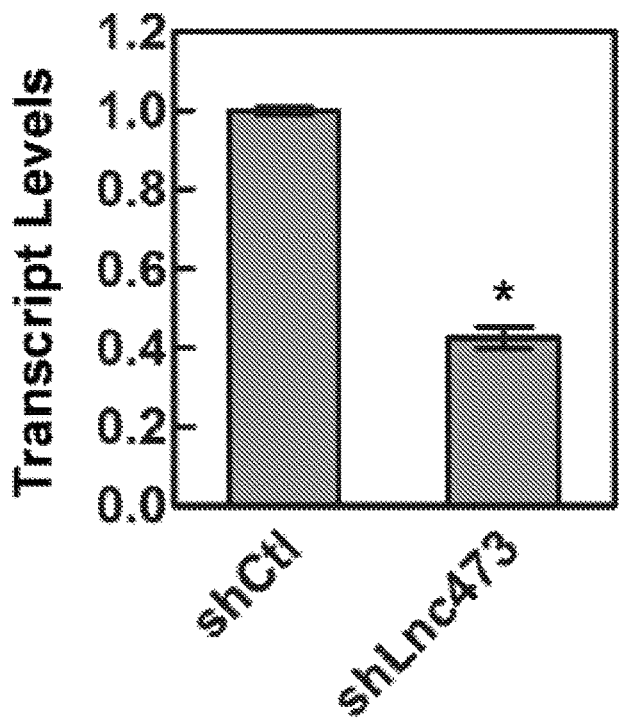
FIGS. 16A-16F. Knockdown of LINC00473 expression in LKB1-null human NSCLC H157 resulted in reduced cell growth and survival in vitro and in vivo. (A) LKB1-null human NSCLC H157 cells were infected with lentiviral-based LINC00473 shRNAs and the scrambled shRNA control (shCtl), respectively. Transduced cells were harvested 96 hours later, and LINC00473 expression was quantified by qRT-PCR (n=3, *p<0.05). (B, C) Transduced cells at 96 hours post-transduction were cultured at $5 \times 10^5$ per well in 6-well plates for another 96 hours and viable cell number was measured using Trypan blue assay (B) and apoptotic cells were detected by Annexin V/PI staining (C) (n=3, *p<0.05). (D, E, F) A total of $1 \times 10^6$ H157 cells after transduction with shLINC00473 or shRNA control for 72 hours were injected subcutaneously to the dorsal flanks of NOD-SCID mice (control shCtl n=5 and shLINC00473 n=6). The excised tumor (D) and the tumor weights (E) were shown at the end points were shown. Tumor growth was measured at different days after tumor cell injection (F) (**p<0.001).
Figure 16B:
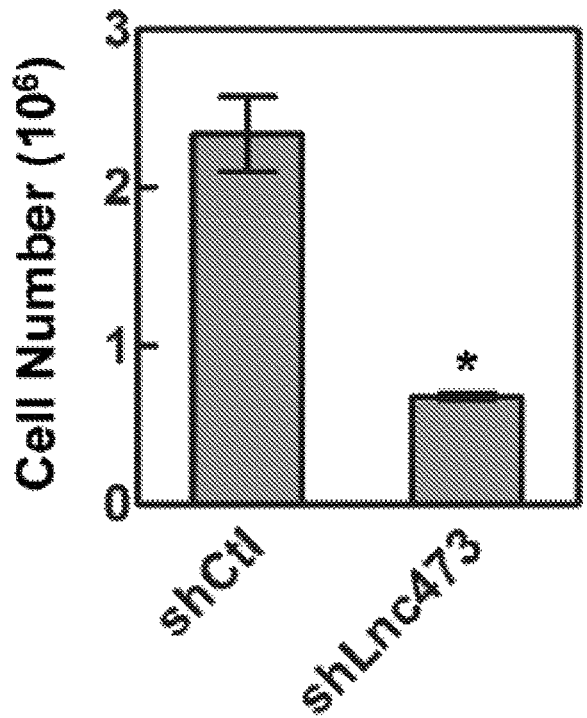
Figure 16C:
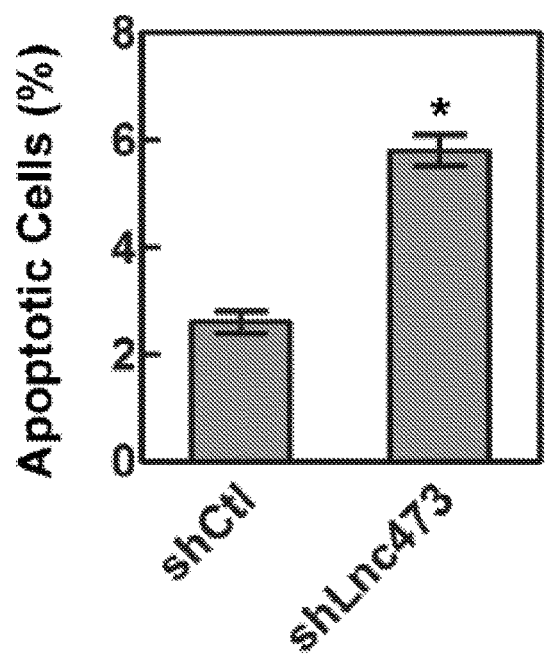
Figure 16D:
Figure 16E:
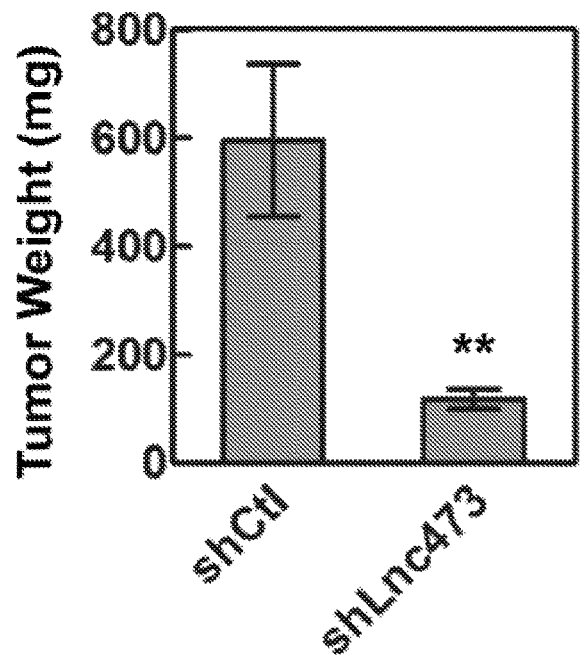
Figure 16F:
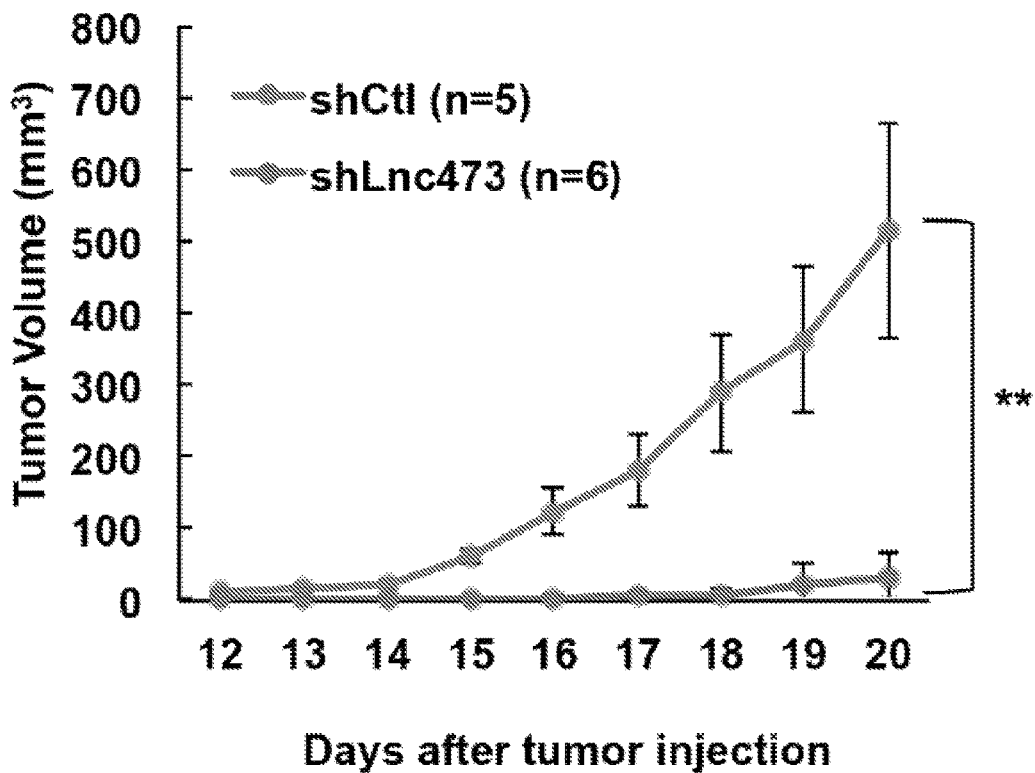
Figure 17A:
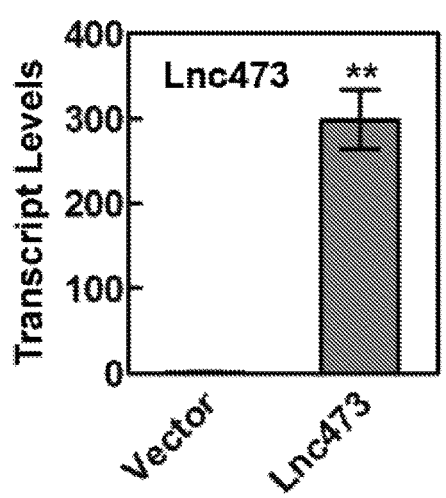
FIGS. 17A-17C. Overexpression of LINC00473 in LKB1-wt lung human NSCLC cells increased cell proliferation and expression of several CREB target genes. (A) LKB1-wt human lung NSCLC cells (H522) were transduced with pLNCX empty vector or LINC00473 retroviruses and LINC00473 expression was confirmed by qRT-PCR (n=3, **p<0.001). (B) LINC00473 expression resulted in a moderate yet significant increase cell proliferation (n=3, *p<0.05). (C) qRT-PCR analysis showed that LINC00473 expression enhanced expression of several CREB target genes. (n=3, *p<0.05 and **p<0.001.)
Figure 17B:
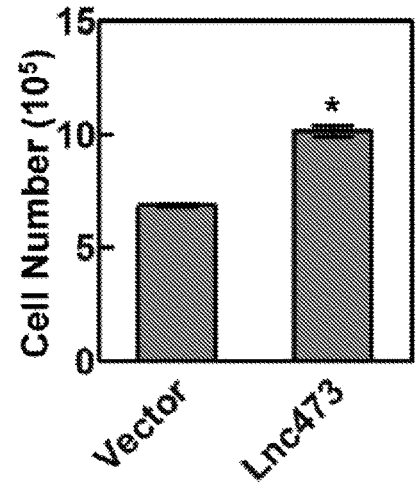

High LINC00473 expression correlated with poor survival of lung cancer patients (FIG. 6G), indicating a role of LINC00473 in cancer progression. Therefore, functional significance of sustained LINC00473 expression in LKB1-inactivated NSCLC cells was investigated. The functional impact of LINC00473 depletion on cell growth and survival was determined using 2 independent lentiviral pLKO.1-based shRNAs targeting exon 2 of LINC00473tv1 (shLnc473-2 and -4). Two shLnc473 caused approximately 90% reduction in LINC00473 transcript levels in A549 cells at 96 hours after lentiviral infection (FIG. 8A). The shLnc473-expressing as well as scrambled shRNA control (shCtl)-expressing cells were subsequently assayed for cell growth and survival. LINC00473 knockdown reduced cell proliferation and enhanced apoptosis in LKB1-null A549 cells (FIG. 8B-8C). Similar effects of LINC00473 depletion on LKB1-null NSCLC cell line H157 were also observed (FIG. 16). Conversely, exogenous LINC00473 over-expression via retroviral transduction in LKB1-wt H522 lung cancer cells resulted in a moderate, yet significant increase in cell proliferation (FIGS. 17A-17B). These data demonstrate that LINC00473 is essential for maintaining LKB1-inactivated lung cancer cell growth and survival.

Figure 8E:
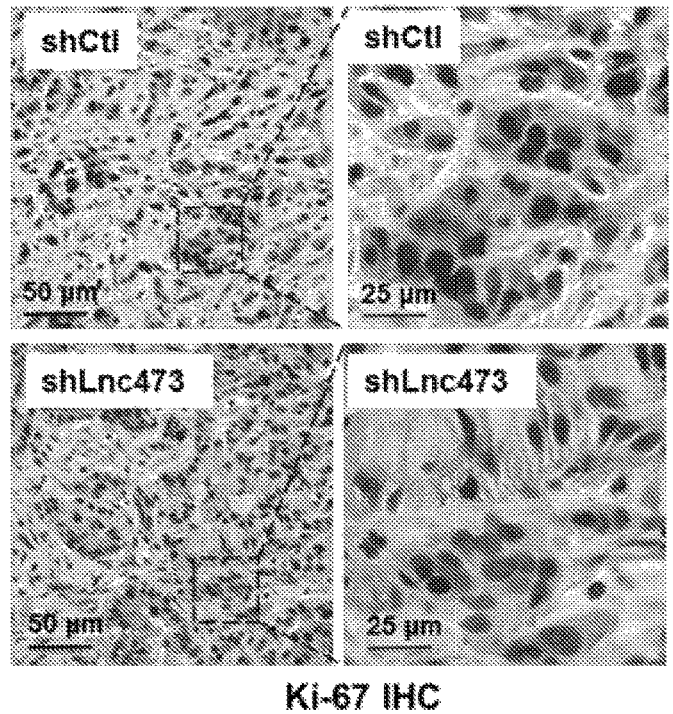

The effect of LINC00473 depletion on the growth of NSCLC xenografts was determined. The luciferase-expressing A549 (A549-luc) cells were transduced with lentiviral-based shLnc473 or scrambled shRNA control for 72 hours and then equal numbers of LINC00473-depleted and control cells were implanted to NOD.SCID mice by subcutaneous injection. LINC00473 depletion significantly reduced the tumor size and weight and blocked the growth of A549-luc xenografts over time (FIGS. 8D and 4D-4F). IHC analysis showed that LINC00473-depleted xenograft tumors contained a reduced number of cells that were positive for the cell proliferation marker Ki-67 (FIG. 8E). Similarly, deletion of LINC0473 expression decreased the growth of H157 xenografts in NOD.SCID mice (FIGS. 16D-16F). Therefore, both in vitro and in vivo evidence supports critical functions of LINC00473 in regulating lung cancer growth and survival.

EXAMPLE 9—LINC00473 IS A NUCLEAR LNCRNA AND FUNCTIONS AS A REGULATOR OF GENE EXPRESSION IN PART THROUGH INTERACTING WITH NONO AND MODULATING CRTC/CREB TRANSCRIPTION

Figure 9A:
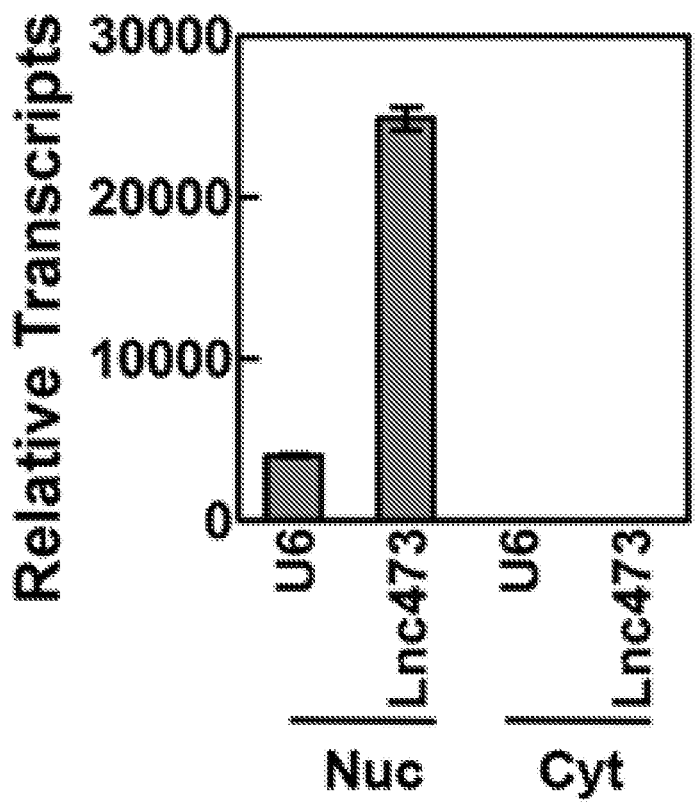
FIGS. 9A-9C. LINC00473 shows predominantly nuclear localization with distinct nuclear structures. (A) The transcript levels of LINC00473 and U6 (a nuclear marker) in the nuclear (Nuc) and cytoplasmic (Cyt) fractions obtained from A549 cells were quantified by qRT-PCR assays. (B) LINC00473 transcripts were enriched in nuclear compartment when compared with nuclear marker U6 and cytoplasmic marker tRNA by Northern blotting analysis in three separate nuclear (N) and cytoplasmic (C) fractions obtained from A549 cells. (C) Nuclear localization of LINC00473 was detected by RNA-FISH in A549 cells. LINC00473 RNA-FISH probe sets were labeled with Quasar 570 dyes (red) and nuclei were labeled with the DNA dye DAPI (blue).
Figure 9B:
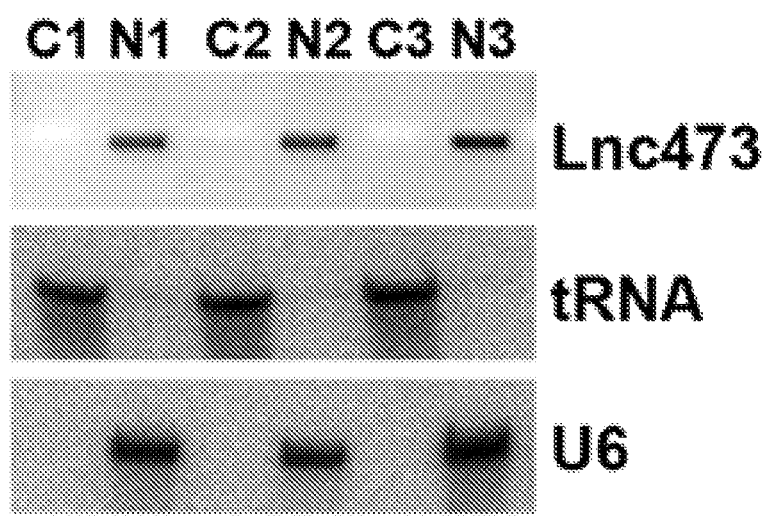
Figure 9C:
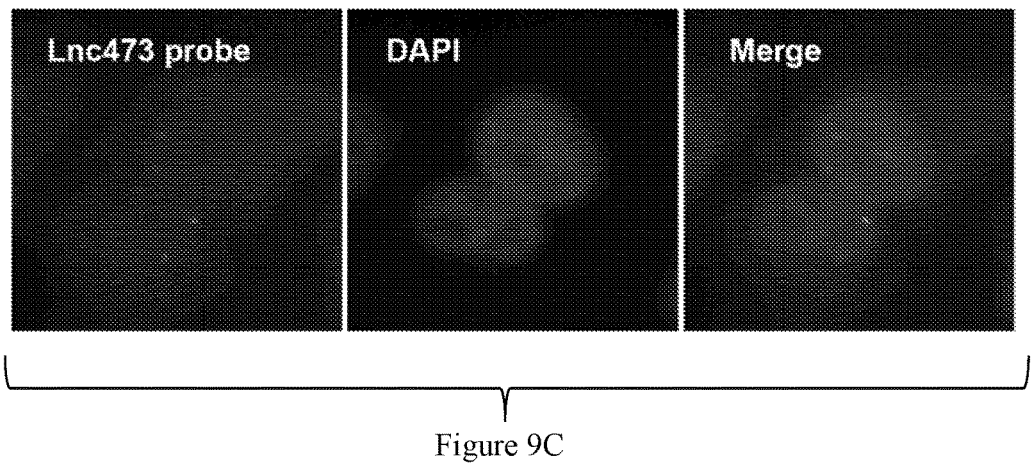

The molecular mechanisms underlying LINC00473 functions are unknown. lncRNAs may be involved in various processes, including transcription, splicing, post-transcriptional regulation, organization of protein complexes, cell-cell signaling, and allosteric regulation of proteins. Knowledge of subcellular localization for lncRNAs can provide a clue for lncRNA functions. Nuclear localization of LINC00473 transcripts in FFPE human lung cancer specimens using customized LINC00473 probes in RNAscope RNA-ISH assays (FIG. 6C). To validate LINC00473 as a nuclear lncRNA, subcellular fractionation assay and RNA fluorescence in situ hybridization (RNA-FISH) were performed. For fractionation assay, cytoplasmic and nuclear fractions were prepared and LINC00473 transcript levels were determined in both fractions. By comparing with the respective cytoplasmic (tRNA) and nuclear (U6) controls, LINC00473 was found to be enriched in the nuclear fraction (FIGS. 9A-9B). For RNA-FISH, fixed cells were hybridized with a mixture of 27 oligonucleotide probes (20-mer) targeting LINC00473, with each probe linked with a single Quasar 570 fluorophore. Positive nuclear signals were observed with 1-2 distinctive dot-like structures as well as less intense, diffuse signals outside the dots (FIG. 9C). LINC00473 signals were undetectable when hybridizations were performed in the presence of RNase, indicating that the signal detection was RNA-dependent. Moreover, exogenous LINC00473 showed similar nuclear localization when over-expressed in LKB1-wt H522 cells. These data strongly support that LINC00473 has distinct nuclear localization and participates in nuclear functions.

Figure 10A:
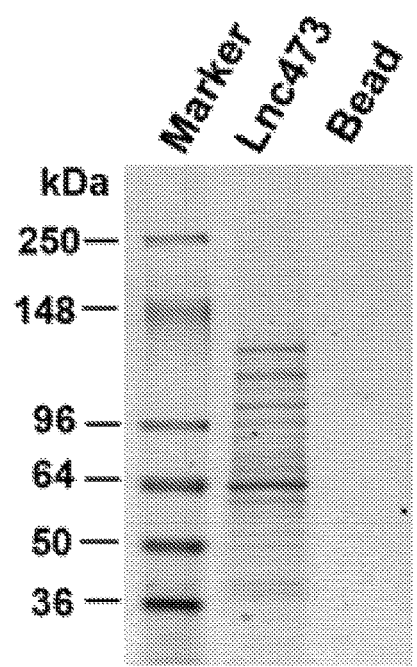
FIGS. 10A-10G. LINC00473 is associated with NONO protein and stimulates CRTC-NONO interaction. (A) Coomassie blue staining of the LINC00473-associated proteins by RNA pull-down in A549 cells. (B) Specific association of LINC00473 RNA with NONO protein was validated through RNA pull-down followed by Western blotting analysis. LINC00473 antisense and MEG RNA were used as controls. (C) Immunoprecipitation of endogenous NONO protein was validated via Western blotting (HC, heavy chain). (D) LINC00473 was significantly enriched in NONO immune-precipitates relative to the IgG control by qRT-PCR assay. ASNS was used as a negative control. (n=3, ***$p<0.0001$). (E) Depletion of LINC00473 caused reduced CRTC1-NONO interaction. A549 cells, after the transduction with LINC00473 shRNA (shLINC00473-2 and 4) or the scramble shRNA lentiviruses (Ctl) for 72 hours, were co-transfected with Gal4-NONO, pSG5-luc (a firefly luciferase reporter containing GAL4-binding sites), pEF-RL (Renilla luciferase) as well as vector control or CRTC1. The luciferase activity was measured 24 hours after transfection (n=3, *p<0.05). (F) Overexpression of LINC00473 enhanced CRTC1-NONO interaction. HEK293T cells were transfected with GAL4-NONO, CRTC1, pSG5-luc, pEF-RL in the presence of vector or LINC00473 construct. The luciferase activity was determined at 24 hours after transfection. (n=3, ***p<0.0001). (G) Relative expression levels of LKB1-regulated genes in shLINC00473-vs. shCtl-A549 cells and in LKB1 vs vector control (Ctl) A549 cells showed that LINC00473 depletion attenuated some common target gene expression induced by LKB1 loss.
Figure 10B:
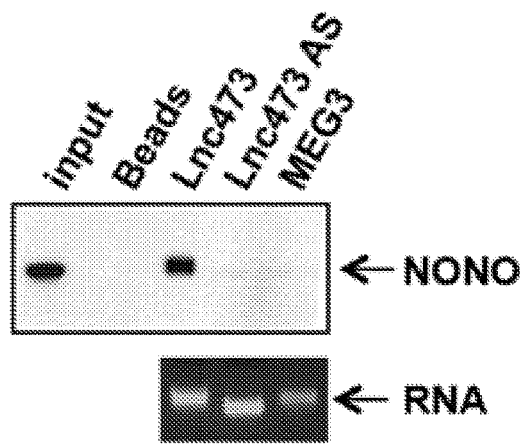
Figure 10C:
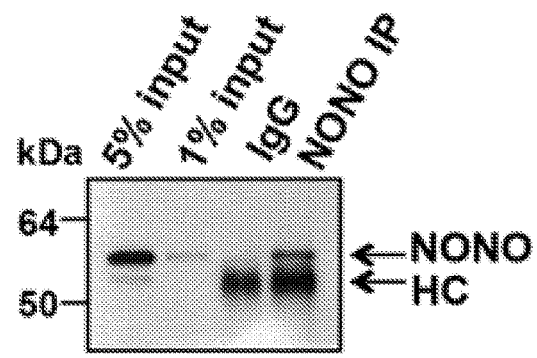
Figure 10D:
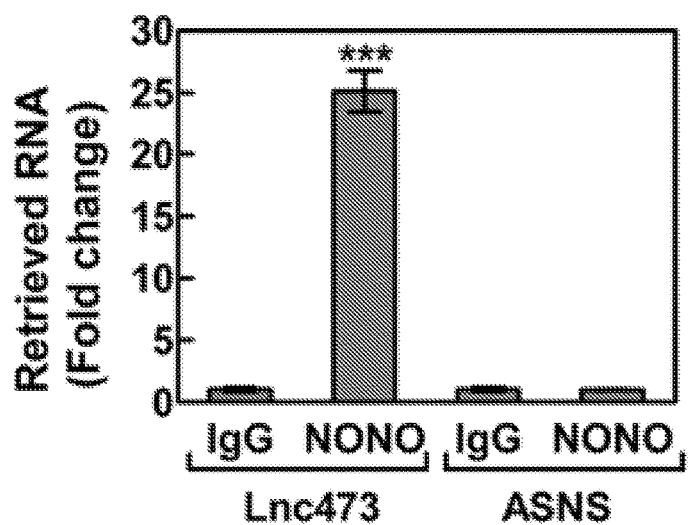

To investigate LINC00473-interacting proteins, RNA pull-down assay was performed followed by a proteomic analysis of the LINC00473-associated protein complex in A549 cells. The in vitro transcribed LINC00473 bound to beads were incubated with A549 nuclear extracts to purify LINC00473 RNA-protein complex. The LINC00473-associated protein complex components were separated by SDS-PAGE (FIG. 10A) and the protein identity was revealed by mass spectrometry (MS). A notable protein was a known CRTC interacting protein, NONO, with 115 peptides detected in this MS analysis (Table 4). To validate the physical interaction between LINC00473 and NONO, RNA pull-down was performed followed by Western blotting with NONO antibodies. NONO was readily detected in LINC00473 RNA pull-down complex but not in the control samples including LINC00473 antisense RNA (AS), LncRNA MEG3 and beads only (FIG. 10B). An RNA immune-precipitation (RNA-IP) was also performed for the RNA-NONO complex using NONO antibodies and measured the amount of LINC00473 associated with NONO immune-precipitates. The immune-precipitated NONO protein levels were confirmed by Western blotting (FIG. 10C). The qRT-PCR results showed significant enrichment of LINC00473, but not the negative control ASNS in NONO immune-precipitates (FIG. 10D). These data indicate that NONO is an LINC00473-associated protein.

Figure 10E:
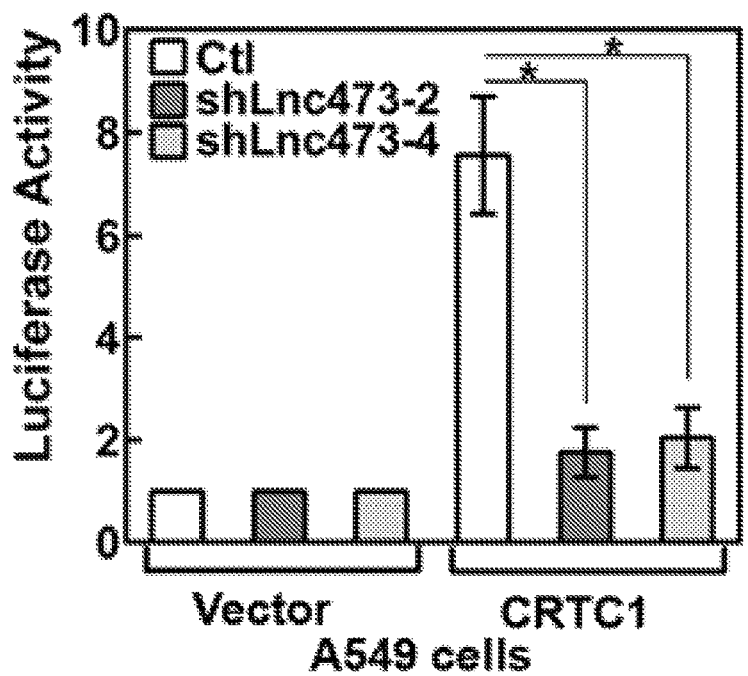
Figure 10F:
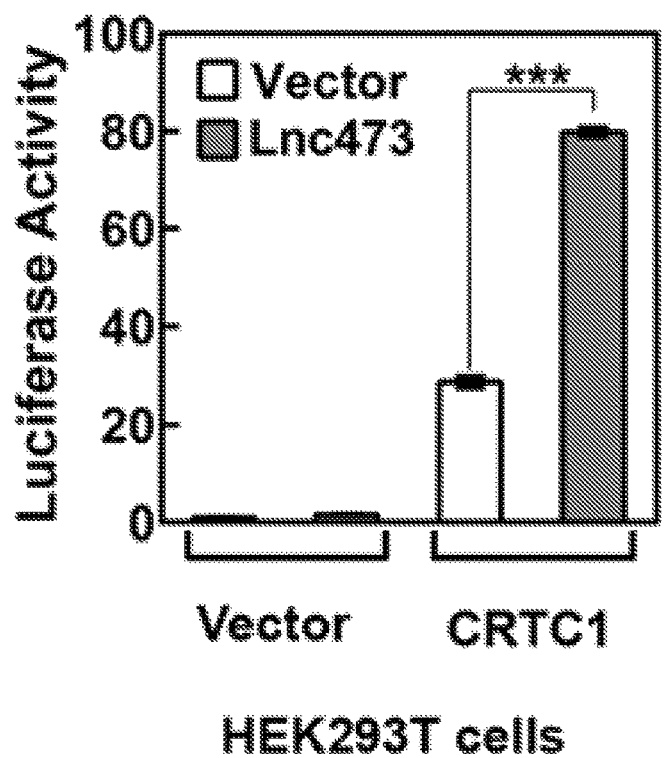
Figure 10G:
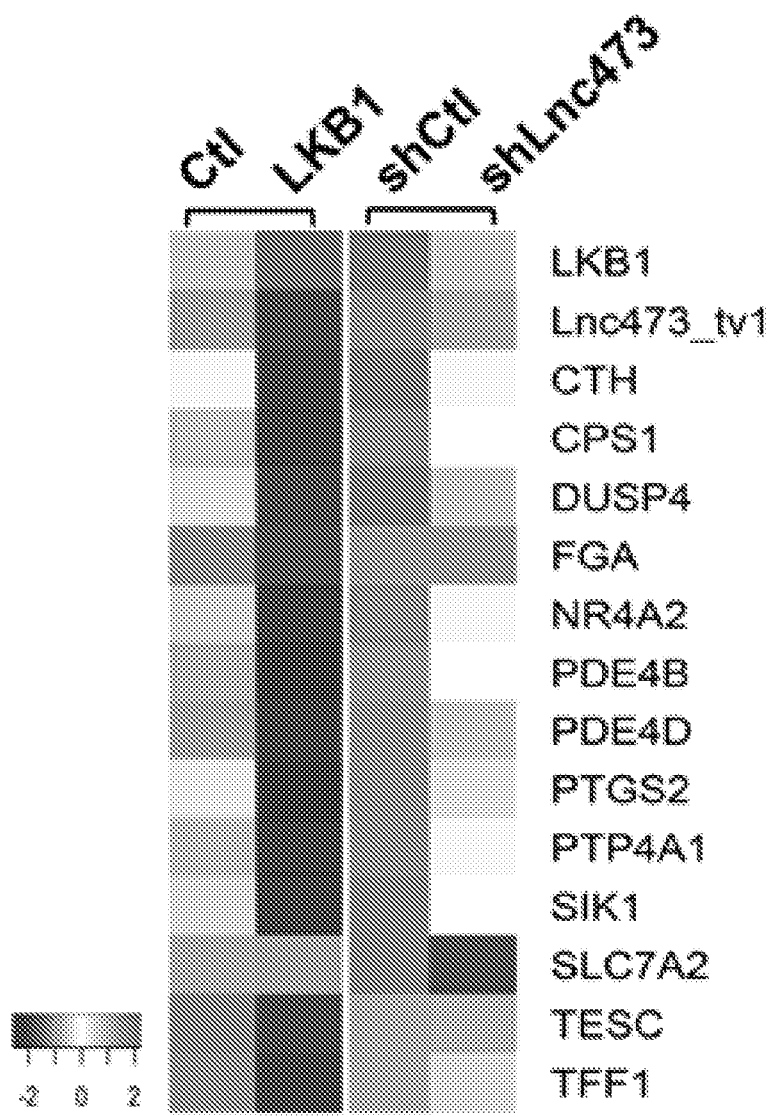
Figure 11:
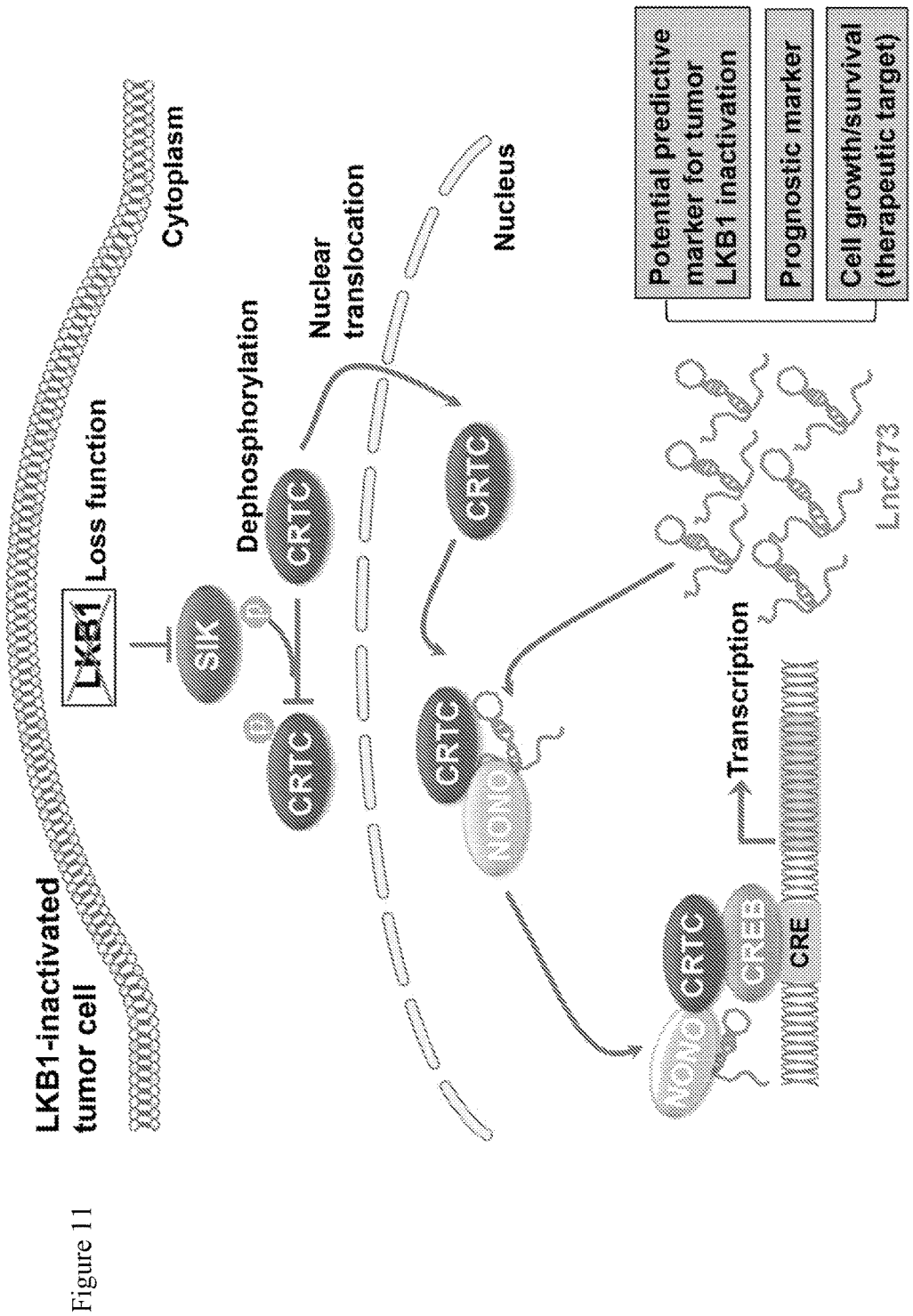
FIG. 11. A model for the molecular basis of LINC00473 induction and the role of sustained LINC00473 expression as a potential biomarker and prognostic marker, therapeutic target, and gene regulator for LKB1-inactivated NSCLC.
Figure 17C:
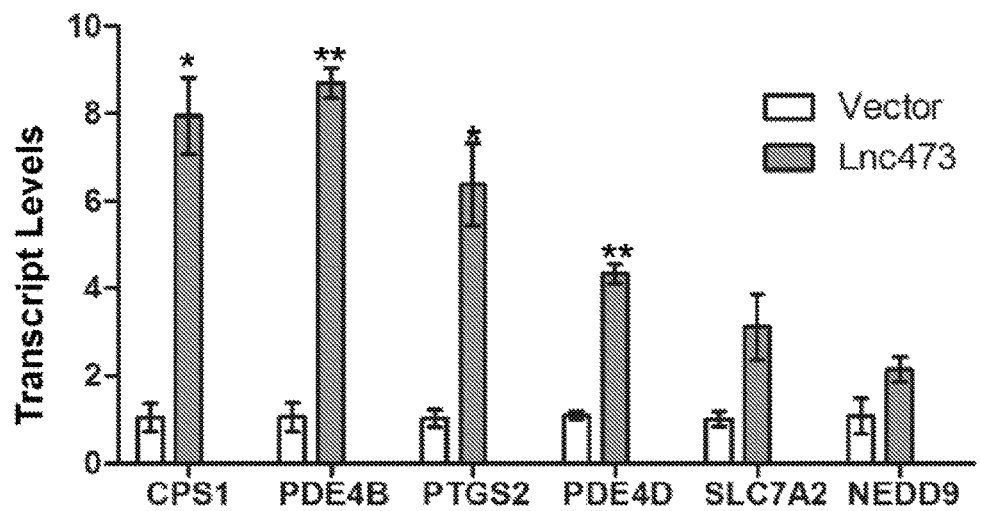

NONO interacts with CRTC co-activators upon cAMP stimulation, which is essential for CREB-mediated transcription. Since LINC00473 physically interacted with NONO, LINC00473 appears to regulate NONO recruitment to CRTCs and promotes subsequent activation of CREB target gene transcription. The interaction of NONO and CRTC was tested when LINC00473 was either depleted or over-expressed using mammalian two-hybrid assays. Depletion of LINC00473 caused a reduced interaction of gal4-NONO and CRTC1, which was indicated by reduced activation of a Gal4 promoter reporter (FIG. 10E). Conversely, enhanced LINC00473 expression promoted NONO-CRTC1 interaction (FIG. 10F). These data suggest that LINC00473 facilitates the recruitment of NONO to CRTC and subsequently promotes CREB-mediated transcription. To further examine whether LINC00473 regulates endogenous CRTC/CREB target genes, gene expression analysis was performed in lentiviral-based scrambled shRNA control and LINC00473-depleted A549 cells as well as in retroviral-based vector control and LKB1-expressing A549 cells in Nanostring assays. LINC00473 depletion impaired expression of several known and potential CRTC/CREB targets including CTH, CPS1, DUSP4, FGA, NR4A2, PDE4B, PDE4D, PTGS2, PTP4A1, SIK1, SLC7A2, TESC and TFF1, whose expression were induced by LKB1 loss (FIG. 10G). Moreover, NEDD9, a CRTC-CREB target gene implicated in regulating cell proliferation and metastasis, was down-regulated in LINC00473-depleted A549 cells, although its expression was not significantly different between LKB1-mut and -wt cell lines. Furthermore, quantitative RT-PCR analysis showed that expression of exogenous LINC00473 in LKB1-wt H522 significantly promoted transcription of several CREB target genes such as CPS1, PDE4B, PTGS2 and PDE4D (FIG. 17C). These data support a model where LINC00473 acts as a co-activator with CRTC/CREB in a positive feedback mechanism to maintain high steady-state levels and induce expression of other LKB1-regulated targets (FIG. 11).

TABLE 4

A list of top potential LINC00473-interacting protein candidates in A549 cells based on proteomic analysis.

| Gene Symbol | Gene ID | Description | Unique peptides | Total peptides |
|---|---|---|---|---|
| DHX9 | 1660 | DEAH (Asp-Glu-Ala-His) box helicase 9 | 59 | 251 |
| HNRNPL | 3191 | heterogeneous nuclear ribonucleoprotein L | 37 | 173 |
| SFPQ | 6421 | splicing factor proline/glutamine-rich | 34 | 166 |
| ILF3 | 3609 | interleukin enhancer binding factor 3, 90 kDa | 47 | 127 |
| PTBP1 | 5725 | polypyrimidine tract binding protein 1 | 26 | 118 |
| NONO | 4841 | non-POU domain containing, octamer-binding | 33 | 115 |
| MATR3 | 9782 | matrin 3 | 39 | 109 |
| HNRNPM | 4670 | heterogeneous nuclear ribonucleoprotein M | 41 | 101 |
| YLPM1 | 56252 | YLP motif containing 1 | 56 | 98 |
| ASPH | 444 | aspartate beta-hydroxylase | 35 | 87 |
| ILF2 | 3608 | interleukin enhancer binding factor 2 | 24 | 87 |
| NCL | 4691 | nucleolin | 31 | 76 |
| HNRNPA2B1 | 3181 | heterogeneous nuclear ribonucleoprotein A2/B1 | 24 | 74 |
| RRBP1 | 6238 | ribosome binding protein 1 | 46 | 72 |
| HNRNPH1 | 3187 | heterogeneous nuclear ribonucleoprotein H1 (H) | 15 | 69 |
| MYBBP1A | 10514 | MYB binding protein (P160) 1a | 40 | 68 |
| MYH9 | 4627 | myosin, heavy chain 9, non-muscle | 56 | 66 |
| PRPF8 | 10594 | pre-mRNA processing factor 8 | 59 | 65 |
| RANBP2 | 5903 | RAN binding protein 2 | 54 | 64 |
| SYNCRIP | 10492 | synaptotagmin binding, cytoplasmic RNA interacting protein | 30 | 63 |
| SNRNP200 | 23020 | small nuclear ribonucleoprotein 200 kDa (U5) | 54 | 56 |
| HNRNPR | 10236 | heterogeneous nuclear ribonucleoprotein R | 27 | 54 |
| HDLBP | 3069 | high density lipoprotein binding protein | 44 | 52 |
| HNRNPU | 3192 | heterogeneous nuclear ribonucleoprotein U | 27 | 52 |
| DDX21 | 9188 | DEAD (Asp-Glu-Ala-Asp) box helicase 21 | 31 | 51 |
| HNRNPF | 3185 | heterogeneous nuclear ribonucleoprotein F | 12 | 50 |
| RBMX | 27316 | RNA binding motif protein, X-linked | 18 | 50 |
| LRPPRC | 10128 | leucine-rich pentatricopeptide repeat containing | 47 | 49 |
| CLTC | 1213 | clathrin, heavy chain (Hc) | 42 | 47 |
| IQGAP1 | 8826 | IQ motif containing GTPase activating protein 1 | 44 | 47 |
| DDX54 | 79039 | DEAD (Asp-Glu-Ala-Asp) box polypeptide 54 | 32 | 46 |
| THRAP3 | 9967 | thyroid hormone receptor associated protein 3 | 23 | 46 |
| U2AF2 | 11338 | U2 small nuclear RNA auxiliary factor 2 | 20 | 46 |
| WDR33 | 55339 | WD repeat domain 33 | 34 | 46 |
| HNRNPK | 3190 | heterogeneous nuclear ribonucleoprotein K | 21 | 45 |
| SF3B1 | 23451 | splicing factor 3b, subunit 1, 155 kDa | 36 | 45 |
| CPSF1 | 29894 | cleavage and polyadenylation specific factor 1, 160 kDa | 34 | 44 |
| DDX5 | 1655 | DEAD (Asp-Glu-Ala-Asp) box helicase 5 | 20 | 44 |
| ELAVL1 | 1994 | ELAV like RNA binding protein 1 | 20 | 43 |
| HNRNPA1L2 | 144983 | heterogeneous nuclear ribonucleoprotein A1-like 2 | 9 | 43 |
| DDX3X | 1654 | DEAD (Asp-Glu-Ala-Asp) box helicase 3, X-linked | 23 | 42 |
| SF3B2 | 10992 | splicing factor 3b, subunit 2, 145 kDa | 30 | 42 |
| DDX17 | 10521 | DEAD (Asp-Glu-Ala-Asp) box helicase 17 | 26 | 41 |
| DHX36 | 170506 | DEAH (Asp-Glu-Ala-His) box polypeptide 36 | 26 | 41 |
| SND1 | 27044 | staphylococcal nuclease and tudor domain containing 1 | 34 | 41 |
| SF3B3 | 23450 | splicing factor 3b, subunit 3, 130 kDa | 34 | 40 |
| XRN2 | 22803 | 5'-3' exoribonuclease 2 | 30 | 40 |
| EPRS | 2058 | glutamyl-prolyl-tRNA synthetase | 37 | 39 |
| HNRNPLL | 92906 | heterogeneous nuclear ribonucleoprotein L-like | 22 | 39 |
| DHX37 | 57647 | DEAH (Asp-Glu-Ala-His) box polypeptide 37 | 32 | 38 |

EXAMPLE 10—LINC00473 AS A CANCER BIOMARKER

Lung cancer is the leading cause of cancer death. Progress in lung cancer treatment improvements will require improved predictive biomarkers so that cancer patients can be provided with the most effective treatments available as well as a larger repertoire of therapeutic targets. A novel lncRNA, namely, LINC00473, is provided whose elevated expression is highly associated with the loss of the tumor suppressor LKB1 gene function, which is one of the most common mutational events in lung cancer. The gene expression and functional data provided herein support the potential utility of LINC00473 as a biomarker and as a therapeutic target for lung cancers with impaired LKB1 signaling. Moreover, mechanistic insights into LINC00473 as a critical nuclear regulator of gene expression in lung cancer are provided.

Recent studies reveal that specific lncRNA expression is associated with disease state, strongly supporting the utility of lncRNAs in clinical diagnosis and prognosis. Loss of LKB1 function in NSCLC cells caused differential responses to therapeutic agents in vitro and in animal studies. LKB1 inactivation sensitized NSCLC cells to the metabolism drug phenformin and a COX2 inhibitor while conferred resistance to PI3K/Akt and MEK inhibitors. However, specific effective treatments are currently not available for patients with LKB1-deficient lung cancer. A big barrier is the lack of reliable assessment for tumor LKB1 inactivation that can be used in clinical trials for patient selection and treatment evaluation. Current clinical LKB1 analysis includes evaluation of LKB1 mutations through sequencing 9 coding exons and flanking region of the LKB1 gene as well as immunohistochemistry (IHC) assay of LKB1 protein expression. However, LKB1 functional inactivation could result from mutations across the entire LKB1 gene, epigenetic silencing, or post-translational inactivation, posing a great challenge to detect LKB1 functional loss through direct genomic sequencing. Also, not all LKB1 mutations impair LKB1 function. LKB1 IHC assay was shown for specific detection of LKB1 protein loss; however, those LKB1 antibodies used were not highly specific. Recently, a 16-gene signature was reported to be capable of predicting tumor cells with LKB1 inactivation, yet the expression of those individual genes is not completely correlated with the tumor LKB1 status and combined scoring of multiple genes for individual tumors require complicated analysis.

The invention provides that LINC00473 gene is induced in LKB1-inactivated primary NSCLC samples and derived cell lines, supporting the concept that that LINC00473 expression could be used for predicting LKB1 functional status in clinically relevant FFPE tumor specimens. There are advantages of using LINC00473 as a surrogate marker for tumor LKB1 functional inactivation. First, LINC00473 expression is a functional readout for LKB1 inactivation; thus LINC00473-based detection will be advantageous over direct sequencing of the entire LKB1 gene or IHC analysis of LKB1 protein detection. A subset of human lung tumors without detectable mutations in the coding region of the LKB1 gene showed positive staining for LINC00473. These tumors likely reflect scenarios where functional LKB1 inactivation is caused by epigenetic affects such as promoter hypermethylation or functional suppression by other mechanisms, including alterations in other components of the LKB1 pathway. For example, BRAF activating mutations were shown to suppress LKB1 kinase activity and thus inactivated LKB1 signaling. On the other hand, a subset of tumors with LKB1 mutations had non-detectable LINC00473 expression. These tumors may have LKB1 mutations that have no significant impact on LKB1 functions. Also, tumor cells having the mutation(s) on one allele of the LKB1 gene may express sufficient level of functional LKB1 proteins. Second, a significant number of LKB1-wt stromal cells within tumors can obscure detection of LKB1-null tumor cells in LKB1 IHC studies. Since LINC00473 normally expresses at a low or undetectable level but at a significantly high level in LKB1-inactivated cells, detection of up-regulated LINC00473 expression will not be affected by the presence of stromal cells. Third, LINC00473 has sufficiently high expression in LKB1-inactivated lung cancer and can be detected in biopsy specimens in the clinic.

Patients with high LINC00473-expressing lung cancers had worse survival, suggesting that LINC00473 likely confers lung cancer cells with aggressive behaviors. Interestingly, a significant number of lncRNAs in human genome seem to have arisen within the primate lineage based on sequence conservation and LINC00473 belongs to this group. It is unclear whether LINC00473 may contribute to any unique features associated with human cancers. LINC00473 plays a role in maintaining human NSCLC cell growth and survival. LINC00473 has low or undetectable expression in normal tissues; therefore, targeting LINC00473 expression is an attractive approach of specifically blocking lung cancer without significantly affecting normal tissues. Currently, anticancer drugs mainly target DNA or proteins in tumor cells. Therapeutic development for RNA-based targeting is in the infancy but various new approaches are being explored such as antisense oligonucleotides and RNA interference (RNAi). Progress has been made to improve delivery and specificity. For example, RNAi therapeutics based on RNAi and lipid nanoparticles (LNP) has been tested in humans supporting further development of RNA targeting drugs in treating cancers. Therefore, targeting LINC00473 expression for blocking NSCLC provides a novel approach for treating NSCLC.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Ulitsky, I. & Bartel, D. P. lincRNAs: genomics, evolution, and mechanisms. *Cell* 154, 26-46 (2013).
2. Li, C. H. & Chen, Y. Targeting long non-coding RNAs in cancers: progress and prospects. *Int J Biochem* Cell Blot 45, 1895-910 (2013).
3. Geisler, S. & Coller, J. RNA in unexpected places: long non-coding RNA functions in diverse cellular contexts. *Nat Rev Mol Cell Biol* (2013).
4. Moran, V. A., Perera, R. J. & Khalil, A. M. Emerging functional and mechanistic paradigms of mammalian long non-coding RNAs. *Nucleic Acids Res* 40, 6391-400 (2012).
5. Wapinski, O. & Chang, H. Y. Long noncoding RNAs and human disease. *Trends Cell Biol* 21, 354-61 (2011).
6. Jemal, A., Bray, F., Center, M. M., Ferlay, J., Ward, E. & Forman, D. Global cancer statistics. *CA Cancer J Clin* 61, 69-90 (2011).
7. Villaflor, V. M. & Salgia, R. Targeted agents in non-small cell lung cancer therapy: What is there on the horizon? *J Carcinog* 12, 7 (2013).
8. Savas, P., Hughes, B. & Solomon, B. Targeted therapy in lung cancer: IPASS and beyond, keeping abreast of the explosion of targeted therapies for lung cancer. *J Thorac Dis* 5, S579-S592 (2013).
9. Minuti, G., D'Incecco, A. & Cappuzzo, F. Targeted therapy for NSCLC with driver mutations. *Expert Opin Biol Ther* 13, 1401-12 (2013).
10. Vaahtomeri, K. & Makela, T. P. Molecular mechanisms of tumor suppression by LKB1. *FEBS Lett* 585, 944-51 (2011).
11. Sanchez-Cespedes, M. The role of LKB1 in lung cancer. *Fam Cancer* 10, 447-53 (2011).
12. Shackelford, D. B. & Shaw, R. J. The LKB1-AMPK pathway: metabolism and growth control in tumour suppression. *Nat Rev Cancer* 9, 563-75 (2009).
13. Ji, H., Ramsey, M. R., Hayes, D. N., Fan, C., McNamara, K., Kozlowski, P., Torrice, C., Wu, M. C., Shimamura, T., Perera, S. A., Liang, M. C., Cai, D., Naumov, G. N., Bao, L., Contreras, C. M., Li, D., Chen, L., Krishnamurthy, J., Koivunen, J., Chirieac, L. R., Padera, R. F., Bronson, R. T., Lindeman, N. I., Christiani, D. C., Lin, X., Shapiro, G. I., Janne, P. A., Johnson, B. E., Meyerson, M., Kwiatkowski, D. J., Castrillon, D. H., Bardeesy, N., Sharpless, N. E. & Wong, K. K. LKB1 modulates lung cancer differentiation and metastasis. *Nature* 448, 807-10 (2007).
14. Chen, Z., Cheng, K., Walton, Z., Wang, Y., Ebi, H., Shimamura, T., Liu, Y., Tupper, T., Ouyang, J., Li, J., Gao, P., Woo, M. S., Xu, C., Yanagita, M., Altabef, A., Wang, S., Lee, C., Nakada, Y., Pena, C. G., Sun, Y., Franchetti, Y., Yao, C., Saur, A., Cameron, M. D., Nishino, M., Hayes, D. N., Wilkerson, M. D., Roberts, P. J., Lee, C. B., Bardeesy, N., Butaney, M., Chirieac, L. R., Costa, D. B., Jackman, D., Sharpless, N. E., Castrillon, D. H., Demetri, G. D., Janne, P. A., Pandolfi, P. P., Cantley, L. C., Kung, A. L., Engelman, J. A. & Wong, K. K. A murine lung cancer co-clinical trial identifies genetic modifiers of therapeutic response. *Nature* 483, 613-7 (2012).
15. Liu, Y., Marks, K., Cowley, G. S., Carretero, J., Liu, Q., Nieland, T. J., Xu, C., Cohoon, T. J., Gao, P., Zhang, Y., Chen, Z., Altabef, A. B., Tchaicha, J. H., Wang, X., Choe, S., Driggers, E. M., Zhang, J., Bailey, S. T., Sharpless, N. E., Hayes, D. N., Patel, N. M., Janne, P. A., Bardeesy, N., Engelman, J. A., Manning, B. D., Shaw, R. J., Asara, J. M., Scully, R., Kimmelman, A., Byers, L. A., Gibbons, D. L., Wistuba, II, Heymach, J. V., Kwiatkowski, D. J., Kim, W. Y., Kung, A. L., Gray, N. S., Root, D. E., Cantley, L. C. & Wong, K. K. Metabolic and functional genomic studies identify deoxythymidylate kinase as a target in LKB1-mutant lung cancer. *Cancer Discov* 3, 870-9 (2013).
16. Shackelford, D. B., Abt, E., Gerken, L., Vasquez, D. S., Seki, A., Leblanc, M., Wei, L., Fishbein, M. C., Czernin, J., Mischel, P. S. & Shaw, R. J. LKB1 inactivation dictates therapeutic response of non-small cell lung cancer to the metabolism drug phenformin. *Cancer Cell* 23, 143-58 (2013).
17. Reitmair, A., Sachs, G., Im, W. B. & Wheeler, L. C6orf176: a novel possible regulator of cAMP-mediated gene expression. *Physiol Genomics* 44, 152-61 (2012).
18. Chen, Z., Chen, J., Gu, Y., Hu, C., Li, J. L., Lin, S., Shen, H., Cao, C., Gao, R., Li, J., Ha, P. K., Kaye, F. J., Griffin, J. D. & Wu, L. Aberrantly activated AREG-EGFR signaling is required for the growth and survival of CRTC1-MAML2 fusion-positive mucoepidermoid carcinoma cells. *Oncogene* (2013).
19. Wu, L., Liu, J., Gao, P., Nakamura, M., Cao, Y., Shen, H. & Griffin, J. D. Transforming activity of MECT1-MAML2 fusion oncoprotein is mediated by constitutive CREB activation. *Embo J* 24, 2391-402 (2005).
20. Gu, Y., Lin, S., Li, J. L., Nakagawa, H., Chen, Z., Jin, B., Tian, L., Ucar, D. A., Shen, H., Lu, J., Hochwald, S. N., Kaye, F. J. & Wu, L. Altered LKB1/CREB-regulated transcription co-activator (CRTC) signaling axis promotes esophageal cancer cell migration and invasion. *Oncogene* 31, 469-79 (2012).
21. Komiya, T., Coxon, A., Park, Y., Chen, W. D., Zajac-Kaye, M., Meltzer, P., Karpova, T. & Kaye, F. J. Enhanced activity of the CREB co-activator Crtc1 in LKB1 null lung cancer. *Oncogene* (2009).
22. Northcott, P. A., Shih, D. J., Remke, M., Cho, Y. J., Kool, M., Hawkins, C., Eberhart, C. G., Dubuc, A., Guettouche, T., Cardentey, Y., Bouffet, E., Pomeroy, S. L., Marra, M., Malkin, D., Rutka, J. T., Korshunov, A., Pfister, S. & Taylor, M. D. Rapid, reliable, and reproducible molecular sub-grouping of clinical medulloblastoma samples. *Acta Neuropathol* 123, 615-26 (2012).
23. Beard, R. E., Abate-Daga, D., Rosati, S. F., Zheng, Z., Wunderlich, J. R., Rosenberg, S. A. & Morgan, R. A. Gene Expression Profiling using Nanostring Digital RNA Counting to Identify Potential Target Antigens for Melanoma Immunotherapy. *Clin Cancer Res* 19, 4941-50 (2013).
24. Geiss, G. K., Bumgarner, R. E., Birditt, B., Dahl, T., Dowidar, N., Dunaway, D. L., Fell, H. P., Ferree, S., George, R. D., Grogan, T., James, J. J., Maysuria, M., Mitton, J. D., Oliveri, P., Osborn, J. L., Peng, T., Ratcliffe, A. L., Webster, P. J., Davidson, E. H., Hood, L. & Dimitrov, K. Direct multiplexed measurement of gene expression with color-coded probe pairs. *Nat Biotechnol* 26, 317-25 (2008).
25. Malkov, V. A., Serikawa, K. A., Balantac, N., Watters, J., Geiss, G., Mashadi-Hossein, A. & Fare, T. Multiplexed measurements of gene signatures in different analytes using the Nanostring nCounter Assay System. *BMC Res Notes* 2, 80 (2009).
26. Sestak, I., Dowsett, M., Zabaglo, L., Lopez-Knowles, E., Ferree, S., Cowens, J. W. & Cuzick, J. Factors predicting late recurrence for estrogen receptor-positive breast cancer. *J Natl Cancer Inst* 105, 1504-11 (2013).
27. Filipits, M., Nielsen, T. O., Rudas, M., Greil, R., Stoger, H., Jakesz, R., Bago-Horvath, Z., Dietze, O., Regitnig, P., Gruber-Rossipal, C., Muller-Holzner, E., Singer, C. F., Mlineritsch, B., Dubsky, P., Bauernhofer, T., Hubalek, M., Knauer, M., Trapl, H., Fesl, C., Schaper, C., Ferree, S., Liu, S., Cowens, J. W., Gnant, M., Austrian, B. & Colorectal Cancer Study, G. The PAM50 risk-of-recurrence score predicts risk for late distant recurrence after endocrine therapy in postmenopausal women with endocrine-responsive early breast cancer. *Clin Cancer Res* 20, 1298-305 (2014).
28. Gittelman, M. C., Hertzman, B., Bailen, J., Williams, T., Koziol, I., Henderson, R. J., Efros, M., Bidair, M. & Ward, J. F. PCA3 molecular urine test as a predictor of repeat prostate biopsy outcome in men with previous negative biopsies: a prospective multicenter clinical study. *J Urol* 190, 64-9 (2013).
29. Esteller, M., Avizienyte, E., Corn, P. G., Lothe, R. A., Baylin, S. B., Aaltonen, L. A. & Herman, J. G. Epigenetic inactivation of LKB1 in primary tumors associated with the Peutz-Jeghers syndrome. *Oncogene* 19, 164-8 (2000).
30. Zheng, B., Jeong, J. H., Asara, J. M., Yuan, Y. Y., Granter, S. R., Chin, L. & Cantley, L. C. Oncogenic BRAF negatively regulates the tumor suppressor LKB1 to promote melanoma cell proliferation. *Mol Cell* 33, 237-47 (2009).
31. Nakada, Y., Stewart, T. G., Pena, C. G., Zhang, S., Zhao, N., Bardeesy, N., Sharpless, N. E., Wong, K. K., Hayes, D. N. & Castrillon, D. H. The LKB1 tumor suppressor as a biomarker in mouse and human tissues. *PLoS One* 8, e73449 (2013).
32. Tonon, G., Modi, S., Wu, L., Kubo, A., Coxon, A. B., Komiya, T., O'Neil, K., Stover, K., El-Naggar, A., Griffin, J. D., Kirsch, I. R. & Kaye, F. J. t(11;19)(q21;p13) translocation in mucoepidermoid carcinoma creates a novel fusion product that disrupts a Notch signaling pathway. *Nat Genet* 33, 208-13 (2003).
33. Barretina, J., Caponigro, G., Stransky, N., Venkatesan, K., Margolin, A. A., Kim, S., Wilson, C. J., Lehar, J., Kryukov, G. V., Sonkin, D., Reddy, A., Liu, M., Murray, L., Berger, M. F., Monahan, J. E., Morais, P., Meltzer, J., Korejwa, A., Jane-Valbuena, J., Mapa, F. A., Thibault, J., Bric-Furlong, E., Raman, P., Shipway, A., Engels, I. H., Cheng, J., Yu, G. K., Yu, J., Aspesi, P., Jr., de Silva, M., Jagtap, K., Jones, M. D., Wang, L., Hatton, C., Palescandolo, E., Gupta, S., Mahan, S., Sougnez, C., Onofrio, R. C., Liefeld, T., MacConaill, L., Winckler, W., Reich, M., Li, N., Mesirov, J. P., Gabriel, S. B., Getz, G., Ardlie, K., Chan, V., Myer, V. E., Weber, B. L., Porter, J., Warmuth, M., Finan, P., Harris, J. L., Meyerson, M., Golub, T. R., Morrissey, M. P., Sellers, W. R., Schlegel, R. & Garraway, L. A. The Cancer Cell Line Encyclopedia enables predictive modelling of anticancer drug sensitivity. *Nature* 483, 603-7 (2012).

34. Pfister, T. D., Reinhold, W. C., Agama, K., Gupta, S., Khin, S. A., Kinders, R. J., Parchment, R. E., Tomaszewski, J. E., Doroshow, J. H. & Pommier, Y. Topoisomerase I levels in the NCI-60 cancer cell line panel determined by validated ELISA and microarray analysis and correlation with indenoisoquinoline sensitivity. *Mol Cancer Ther* 8, 1878-84 (2009).

35. Bittinger, M. A., McWhinnie, E., Meltzer, J., Iourgenko, V., Latario, B., Liu, X., Chen, C. H., Song, C., Garza, D. & Labow, M. Activation of cAMP response element-mediated gene expression by regulated nuclear transport of TORC proteins. *Curr Biol* 14, 2156-61 (2004).

36. Ahn, S., Olive, M., Aggarwal, S., Krylov, D., Ginty, D. D. & Vinson, C. A dominant-negative inhibitor of CREB reveals that it is a general mediator of stimulus-dependent transcription of c-fos. *Mol Cell Biol* 18, 967-77 (1998).

37. Kaufman, J. M., Amann, J. M., Park, K., Arasada, R. R., Li, H., Shyr, Y. & Carbone, D. P. LKB1 Loss induces characteristic patterns of gene expression in human tumors associated with NRF2 activation and attenuation of PI3K-AKT. *J Thorac Oncol* 9, 794-804 (2014).

38. Ito, I., Ji, L., Tanaka, F., Saito, Y., Gopalan, B., Branch, C. D., Xu, K., Atkinson, E. N., Bekele, B. N., Stephens, L. C., Minna, J. D., Roth, J. A. & Ramesh, R. Liposomal vector mediated delivery of the 3p FUS1 gene demonstrates potent antitumor activity against human lung cancer in vivo. *Cancer Gene Ther* 11, 733-9 (2004).

39. Gutschner, T., Hammerle, M., Eissmann, M., Hsu, J., Kim, Y., Hung, G., Revenko, A., Arun, G., Stentrup, M., Gross, M., Zornig, M., MacLeod, A. R., Spector, D. L. & Diederichs, S. The noncoding RNA MALAT1 is a critical regulator of the metastasis phenotype of lung cancer cells. *Cancer Res* 73, 1180-9 (2013).

40. Groskopf, J., Aubin, S. M., Deras, I. L., Blase, A., Bodrug, S., Clark, C., Brentano, S., Mathis, J., Pham, J., Meyer, T., Cass, M., Hodge, P., Macairan, M. L., Marks, L. S. & Rittenhouse, H. APTIMA PCA3 molecular urine test: development of a method to aid in the diagnosis of prostate cancer. *Clin Chem* 52, 1089-95 (2006).

41. Lin, S., Tian, L., Shen, H., Gu, Y., Li, J. L., Chen, Z., Sun, X., James You, M. & Wu, L. DDX5 is a positive regulator of oncogenic NOTCH1 signaling in T cell acute lymphoblastic leukemia. *Oncogene* 32, 4845-53 (2013).

42. Yang, F., Huo, X. S., Yuan, S. X., Zhang, L., Zhou, W. P., Wang, F. & Sun, S. H. Repression of the long noncoding RNA-LET by histone deacetylase 3 contributes to hypoxia-mediated metastasis. *Mol Cell* 49, 1083-96 (2013).

43. Rinn, J. L., Kertesz, M., Wang, J. K., Squazzo, S. L., Xu, X., Brugmann, S. A., Goodnough, L. H., Helms, J. A., Farnham, P. J., Segal, E. & Chang, H. Y. Functional demarcation of active and silent chromatin domains in human HOX loci by noncoding RNAs. *Cell* 129, 1311-23 (2007).

44. Batista, P. J. & Chang, H. Y. Long noncoding RNAs: cellular address codes in development and disease. *Cell* 152, 1298-307 (2013).

45. Lin, S., Shen, H., Li, J. L., Tang, S., Gu, Y., Chen, Z., Hu, C., Rice, J. C., Lu, J. & Wu, L. Proteomic and functional analyses reveal the role of chromatin reader SFMBT1 in regulating epigenetic silencing and the myogenic gene program. *J Biol Chem* 288, 6238-47 (2013).

46. Subramanian, A., Tamayo, P., Mootha, V. K., Mukherjee, S., Ebert, B. L., Gillette, M. A., Paulovich, A., Pomeroy, S. L., Golub, T. R., Lander, E. S. & Mesirov, J. P. Gene set enrichment analysis: a knowledge based approach for interpreting genome-wide expression profiles. *Proc Natl Acad Sci USA* 102, 15545-50 (2005).

47. Tang, M., Shen, H., Jin, Y., Lin, T., Cai, Q., Pinard, M. A., Biswas, S., Tran, Q., Li, G., Shenoy, A. K., Tongdee, E., Lin, S., Gu, Y., Law, B. K., Zhou, L., McKenna, R., Wu, L. & Lu, J. The Malignant Brain Tumor (MBT) Domain Protein SFMBT1 Is an Integral Histone Reader Subunit of the LSD1 Demethylase Complex for Chromatin Association and Epithelial-to-mesenchymal Transition. *J Biol Chem* 288, 27680-91 (2013).

48. Hoheisel, Microarray technology: beyond transcript profiling and genotype analysis, *Nature Reviews Genetics* 7, 200-210 (2006).

49. Reinhard Waehler, Stephen J. Russell & David T. Curiel, Engineering targeted viral vectors for gene therapy, *Nature Reviews Genetics* 8, 573-587 (2007).

50. Hao Yin, Rosemary L. Kanasty, Ahmed A. Eltoukhy, Arturo J. Vegas, J. Robert Dorkin & Daniel G. Anderson, Non-viral vectors for gene-based therapy, *Nature Reviews Genetics* 15, 541-555 (2014).

51. Erkki Ruoslahti, Sangeeta N. Bhatia and Michael J. Sailor, Targeting of drugs and nanoparticles to tumors, *Journal of Cell Biology*, 188(6): 759-768.

52. Amer, Gene therapy for cancer: present status and future perspective, *Molecular and Cellular Therapies*, 2:27 (2014).

53. Ling, H., Fabbri, M. and Calin, G. A., MicroRNAs and other non-coding RNAs as targets for anticancer drug development, *Nature Reviews Drug Discovery*, Vol. 12, 847-865 (2013).

54. Naito, Y. and Ui-Tei, K., siRNA Design Software for a Target Gene-Specific RNA Interference, *Frontiers in Genetics,* 3:102 (2012).

55. Yin, H., Kanasty, R. L., Eltoukhy, A. A., Vegas, A. J., Dorkin, J. R. & Anderson, D. G., Non-viral vectors for gene-based therapy, Nature Reviews Genetics 15, 541-555 (2014).

56. Janku, F., Stewart, D. J., Kurzrock, R. Targeted therapy in non-small-cell lung cancer—is it becoming a reality? Nat Rev Clin Oncol. 2010; 7:401-414.

57. Koivunen, J. P., et al. EML4-ALK fusion gene and efficacy of an ALK kinase inhibitor in lung cancer. Clin Cancer Res. 2008; 14:4275-4283.

58. Paez, J. G., et al. EGFR mutations in lung cancer: correlation with clinical response to gefitinib therapy. Science. 2004; 304:1497-1500.

59. Alessi, D. R., Sakamoto, K., Bayascas, J. R. LKB1-dependent signaling pathways. Annu Rev Biochem. 2006; 75:137-163.

60. Hemminki, A., et al. A serine/threonine kinase gene defective in Peutz-Jeghers syndrome. Nature. 1998; 391:184-187.

We claim:

1. A method of treating a subject having a non-small lung cancer involving loss or reduction in LKB1 function, the method comprising:
   a) determining a level of LINC00473 in a test sample obtained from the subject;
   b) identifying the subject as having the cancer involving loss or reduction in LKB1 function based on the level of LINC00473 in the test sample; and
   c) administering an effective amount of a LINC00473 inhibitor to the subject to treat the cancer, wherein the LINC00473 inhibitor is a small-inhibitory RNA (siRNA), short hairpin RNA (shRNA), or antisense oligonucleotide.

2. The method of claim 1, wherein the determining step further comprises obtaining a control sample, wherein the level of LINC00473 in the test sample relative to the control sample indicates the presence of the cancer involving loss or reduction in LKB1 function in the subject; and wherein the control sample is obtained from an individual belonging to the same species as the subject and known to have a cancer involving loss or reduction in LKB1 function and the method comprises identifying the subject as having the cancer involving loss or reduction in LKB1 based on the level of LINC00473 in the test sample compared to that of the control sample.

3. The method of claim 1, further comprising obtaining a reference value corresponding to a level LINC00473, and wherein
   the method comprises identifying the subject as having the cancer involving loss or reduction in LKB1 based on a level of LINC00473 in the test sample as compared to the reference value.

4. The method of claim 1, wherein the LINC00473 inhibitor is administered to the subject via gene therapy.

5. The method of claim 1, wherein a cancer therapy in addition to the LINC00473 inhibitor is administered to the subject identified as having the cancer involving loss or reduction in LKB1.

6. The method of claim 1, wherein the step of determining the level of LINC00473 is performed by Northern blot analysis, quantitative or semi-quantitative reverse transcription-polymerase chain reaction (RT-PCR), ligase chain reaction (LCR), transcription-mediated amplification (TMA), strand displacement amplification (SDA) and nucleic acid sequence based amplification (NASBA).

7. The method of claim 1, wherein the subject is a mammal.

8. The method of claim 7, wherein the mammal is a human, ape, canine, pig, bovine, rodent, or feline.

9. The method of claim 2, wherein the control sample and the test sample are obtained from the same type of an organ or tissue.

10. The method of claim 9, wherein the organ or tissue is lung.

11. The method of claim 1, wherein the levels of LINC00473 are determined my measuring levels of SEQ ID NO: 1, SEQ ID NO: 2 or both SEQ ID NO: 1 and SEQ ID NO: 2 in the test sample.

12. A method of treating a subject having a non-small lung cancer involving loss or reduction in LKB1 function, the method comprising administering an effective amount of a LINC00473 inhibitor to the subject to treat the cancer, wherein the LINC00473 inhibitor is a small-inhibitory RNA (siRNA), short hairpin RNA (shRNA), bifunctional RNA, antisense oligonucleotide, ribozyme, deoxyribozyme, or aptamer.

13. The method of claim 12, wherein the LINC00473 inhibitor is administered to the subject via gene therapy.

14. The method of claim 5, wherein the cancer therapy in addition to the LINC00473 inhibitor is radiotherapy.

15. The method of claim 5, wherein the cancer therapy in addition to the LINC00473 inhibitor is chemotherapy.

16. The method of claim 5, wherein the cancer therapy in addition to the LINC00473 inhibitor is surgery.

17. The method of claim 5, wherein the cancer therapy in addition to the LINC00473 inhibitor is immunotherapy.

18. The method of claim 5, wherein the cancer therapy in addition to the LINC00473 inhibitor is kinase inhibition.

19. The method of claim 5, wherein the cancer therapy in addition to the LINC00473 inhibitor is monoclonal antibody therapy.

* * * * *